(12) United States Patent
Kwong et al.

(10) Patent No.: US 7,709,100 B2
(45) Date of Patent: May 4, 2010

(54) ELECTROLUMINESCENT EFFICIENCY

(75) Inventors: Raymond Kwong, Plainsboro, NJ (US); David Knowles, Apollo, PA (US); Bin Ma, Monroeville, PA (US); Xiao-Chang Li, Yardley, PA (US); William Ceyrolles, Coraopolis, PA (US)

(73) Assignee: Universal Display Corporation, Ewing, NJ (US)

( * ) Notice: Subject to any disclaimer, the term of this patent is extended or adjusted under 35 U.S.C. 154(b) by 552 days.

(21) Appl. No.: 11/018,453

(22) Filed: Dec. 21, 2004

(65) Prior Publication Data

US 2006/0008673 A1   Jan. 12, 2006

Related U.S. Application Data

(63) Continuation-in-part of application No. 10/886,367, filed on Jul. 7, 2004, now abandoned.

(51) Int. Cl.
*H01L 51/54* (2006.01)
*C09K 11/06* (2006.01)

(52) U.S. Cl. ............... 428/690; 428/917; 313/504; 313/506; 257/E51.044; 546/4; 546/10

(58) Field of Classification Search ............... None
See application file for complete search history.

(56) References Cited

U.S. PATENT DOCUMENTS

| | | | |
|---|---|---|---|
| 3,876,675 A * | 4/1975 | Trofimenko | ............... 556/41 |
| 4,769,292 A | 9/1988 | Tang et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,310,360 B1 | 10/2001 | Forrest et al. | |
| 6,337,102 B1 | 1/2002 | Forrest et al. | |
| 6,468,819 B1 | 10/2002 | Kim et al. | |
| 6,548,956 B2 | 4/2003 | Forrest et al. | |
| 6,576,134 B1 | 6/2003 | Agner | |
| 6,602,540 B2 | 8/2003 | Gu et al. | |
| 6,815,091 B2 | 11/2004 | Takiguchi et al. | |
| 6,830,828 B2 | 12/2004 | Thompson et al. | |
| 6,835,469 B2 | 12/2004 | Kwong et al. | |
| 7,332,232 B2 * | 2/2008 | Ma et al. | ............... 428/690 |
| 2002/0024293 A1 | 2/2002 | Igarashi et al. | |
| 2002/0071963 A1 | 6/2002 | Fujii | |
| 2002/0182441 A1 | 12/2002 | Lamansky et al. | |
| 2003/0059646 A1 * | 3/2003 | Kamatani et al. | ........... 428/690 |
| 2003/0068526 A1 * | 4/2003 | Kamatani et al. | ........... 428/690 |
| 2003/0068535 A1 | 4/2003 | Takiguchi et al. | |
| 2003/0068536 A1 * | 4/2003 | Tsuboyama et al. | ......... 428/704 |
| 2003/0073665 A1 | 4/2003 | Thompson et al. | |
| 2003/0109758 A1 | 6/2003 | Gobbel et al. | |
| 2003/0235712 A1 * | 12/2003 | Takiguchi et al. | ........... 428/690 |
| 2004/0086743 A1 | 5/2004 | Brown et al. | |
| 2004/0174116 A1 | 9/2004 | Lu et al. | |
| 2004/0241495 A1 | 12/2004 | Kwong et al. | |
| 2005/0025993 A1 | 2/2005 | Thompson et al. | |
| 2005/0170207 A1 * | 8/2005 | Ma et al. | ................... 428/690 |

FOREIGN PATENT DOCUMENTS

| | | |
|---|---|---|
| DE | 674400 | 4/1939 |
| EP | 1191613 | 3/2002 |
| EP | 1239526 | 9/2002 |
| EP | 1348711 | 10/2003 |
| WO | WO 03/000661 A1 * | 1/2003 |
| WO | WO 2003000959 | 1/2003 |
| WO | WO 03/040257 | 5/2003 |
| WO | WO 03/069961 | 8/2003 |

OTHER PUBLICATIONS

Kwong et al., "High Operational Stability of Electrophosphorescent Devices," Appl. Phys. Lett., vol. 81, pp. 162 (2002).

Baldo et al., "Highly Efficient Phosphorescent Emission from Organic Electroluminescent Devices," Nature, vol. 395, pp. 151-154 (1998).

(Continued)

*Primary Examiner*—Marie R. Yamnitzky
(74) *Attorney, Agent, or Firm*—Kenyon & Kenyon LLP

(57) ABSTRACT

An organic light emitting device is provided. The device has an anode, a cathode, and an emissive layer disposed between the anode and the cathode. The emissive layer further includes a molecule of Formula I (shown below) wherein an alkyl substituent at position $R'_5$, which is an alkyl substituent, results in high efficiency and operational stability in the organic light emitting device.

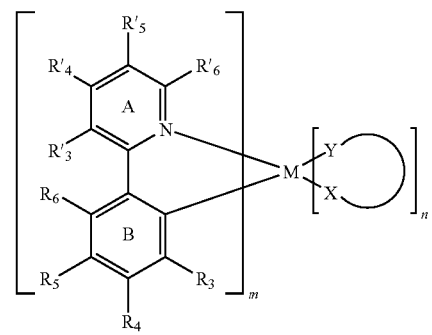

12 Claims, 38 Drawing Sheets

OTHER PUBLICATIONS

Baldo et al., "Very High-Efficiency Green Organic Light-Emitting Devices Based on Electrophosphorescence," Appl. Phys. Lett., vol. 75, No. 1 pp. 4-6 (1999).

Adachi et al., "Nearly.100% Internal Phosphorescence Efficiency in an Organic Light Emitting Device." J. Appl. Phys., vol. 90 pp. 5048 (2001).

Ikai et al, "Highly Efficient Phosphorescence from Organic Light-Emitting Devices with an Exciton-Block Layer," Appl. Phys. Lett., vol. 79, pp. 156 (2001).

Parish et al., "Mercury (II) and Gold (III) Derivatives of 2-Phenyl Pyridines and 2-Phenyl-4-(methylcarbonxylato)quinoline," Journal of Organometallic Chemistry (2000), 596 (1-2) pp. 165-176.

Muerner et al., "Strong enhancement of the lanthanide-centered luminescence in complexes with 4-alkylated 2,2':6',2''-terpyridines," J. Chem. Soc., Dalton Trans., pp. 2809-2816 (2000).

U.S. Appl. No. 10/233,470 to Shtein et al., "Process and Apparatus for Organic Vapor Jet Deposition," filed Sep. 4, 2002, (not published).

U.S. Appl. No. 10/765,295 to Kwon et al., "Improved Electroluminescent Stability," filed Jan. 26, 2004, (2005/0164030).

Thomas S. W. et al., "Towards chemosensing phosphorescent conjugated polymers: cyclometalated platinum(II) poly(phenylene)s " Journal of Materials Chemistry, vol. 15, No. 27/28, pp. 2829-2835 (2005).

Slinker J. D. et al., "Green electroluminescence from an ionic iridium complex", Applied Physics Letters, vol. 86, No. 17, pp. 173506-1 (2005).

Goldsmith J. I. et al., "Discovery and high-throughput screening of heteroleptic iridium complexes for photoinduced hydrogen production", Journal of the American Chemical Society, vol. 127, No. 20, pp. 7502-7510 (2005).

Jung S et al., "Effect of substitution of methyl groups on the luminescence performance of $Ir^{III}$ complexes: Preparation, structures, electrochemistry, photophysical properties and their applications in organic light-emitting diodes (OLEDs)", European Journal of Inorganic Chemistry, No. 17, pp. 3415-2323 (2004).

Lowry M. S. et al., "Accelerated luminophore discovery through combinatorial synthesis", Journal of the American Chemical Society, vol. 126, No. 43, pp. 14129-14135 (2004).

Brooks J. et el., "Synthesis and characterization of phosphorescent cyclometalated platium complexes", Inorganic Chemistry, vol. 41, No. 12, pp. 3055-3066 (2001).

Kobayashi K. et al., "New synthesis of isoquinoline derivateives by reactions of 2-(2-methoxyethenyl) benzonitriles with organolithiums and lithium dialkylamides", Chemistry Letters, vol. 33, No. 3, pp. 236-237 (2004).

Abramovitch R. A. et al., "Orientation in the reaction of phenyllithium with 3-substituted pyridines", Tetrahedron Letters. vol. 1. No. 8, pp. 1-3 (1959).

International Search Report for PCT/US2005/024295.

* cited by examiner

*Devices annealed

*Devices annealed

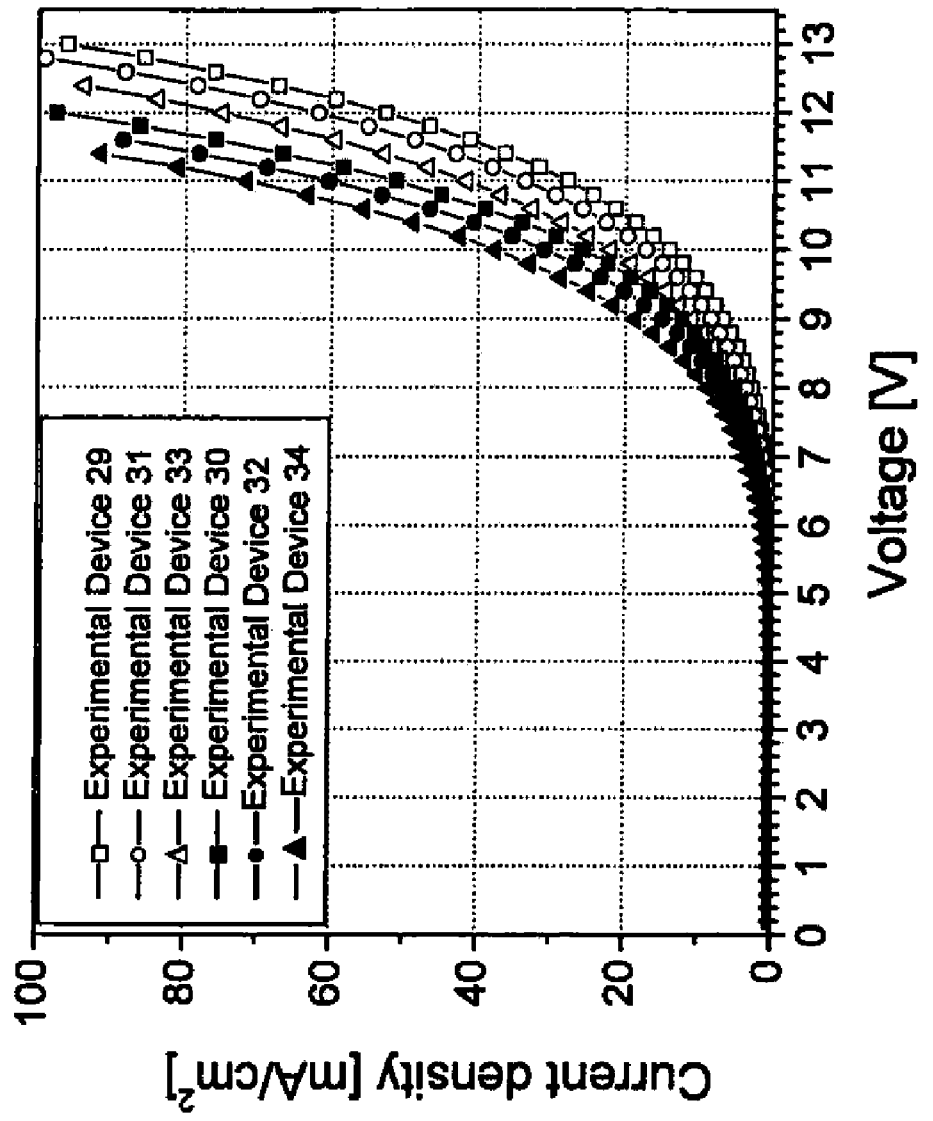
Figure 31. Current Density vs. Voltage

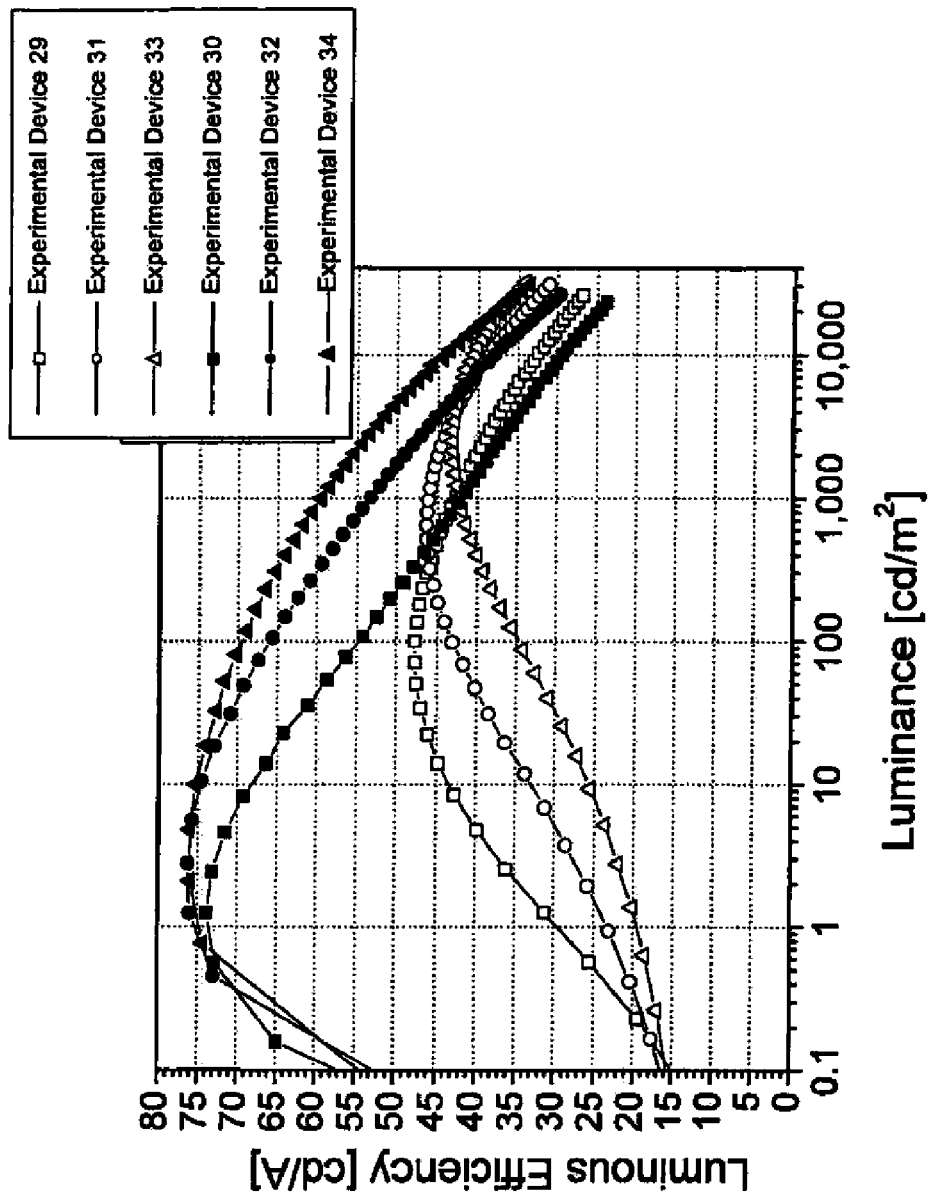
Figure 32. Luminous efficiency vs. luminance

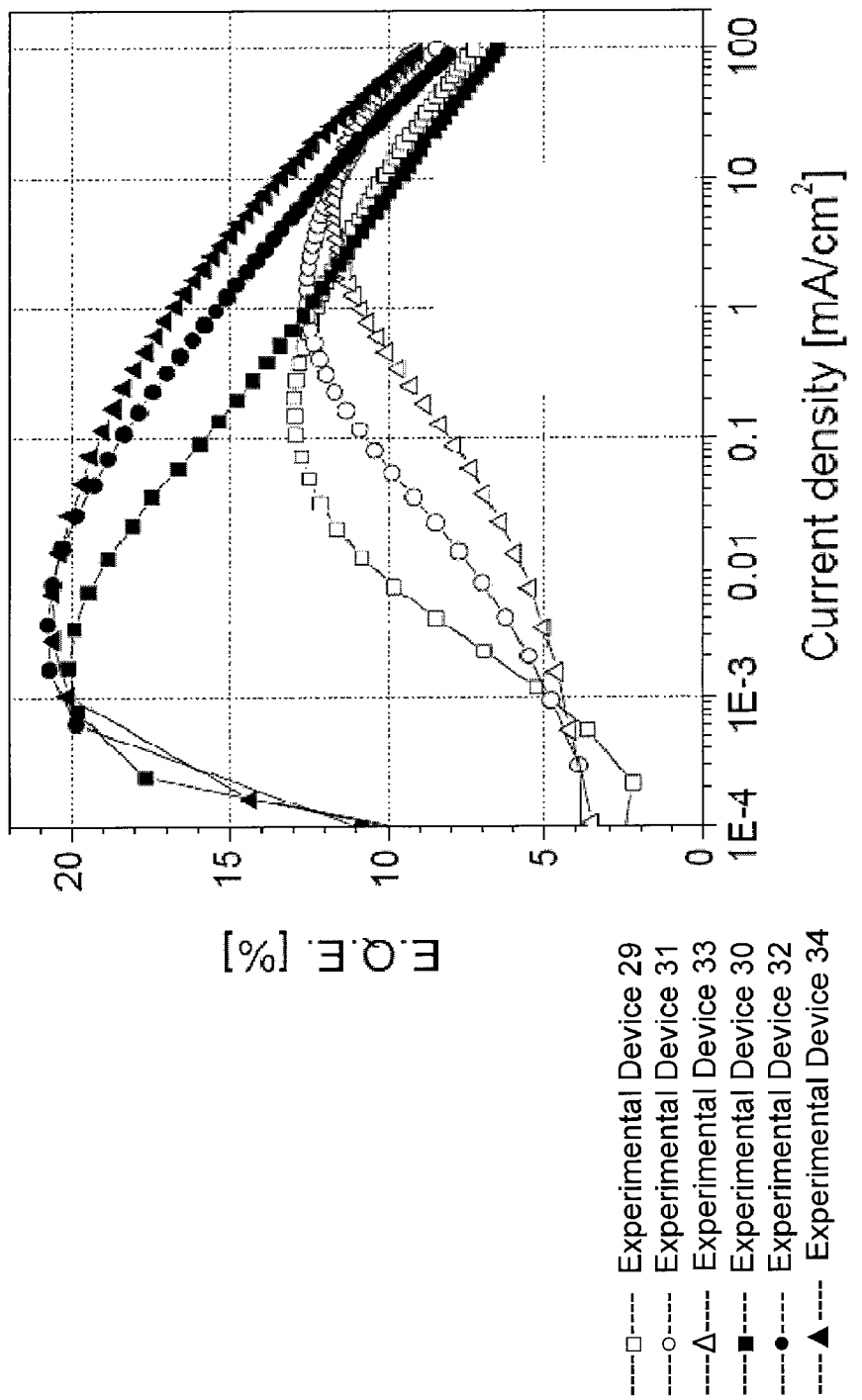
Figure 33. External quantum efficiency vs. current density

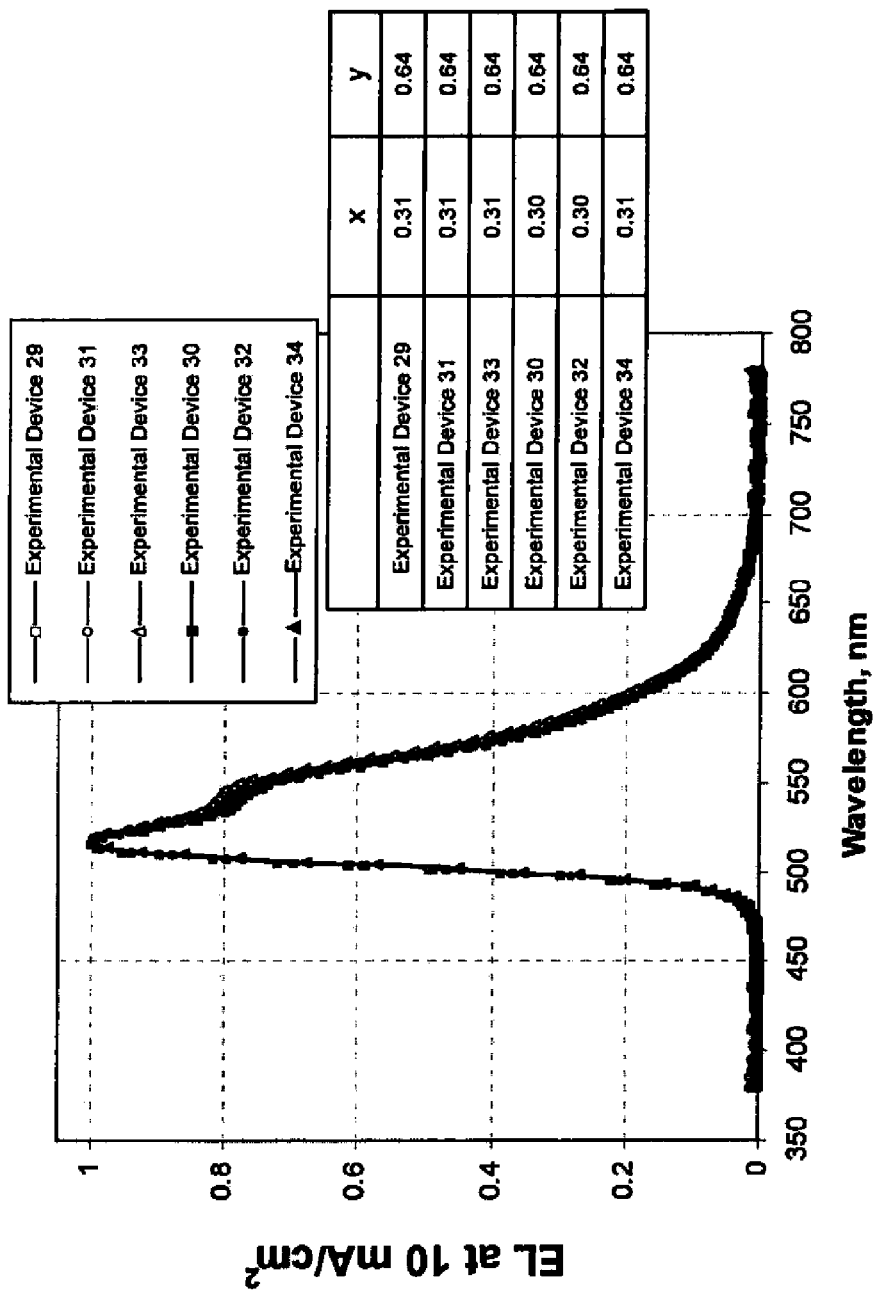
Figure 34. Electroluminescence spectra and CIE coordinates at 10 mA/cm²

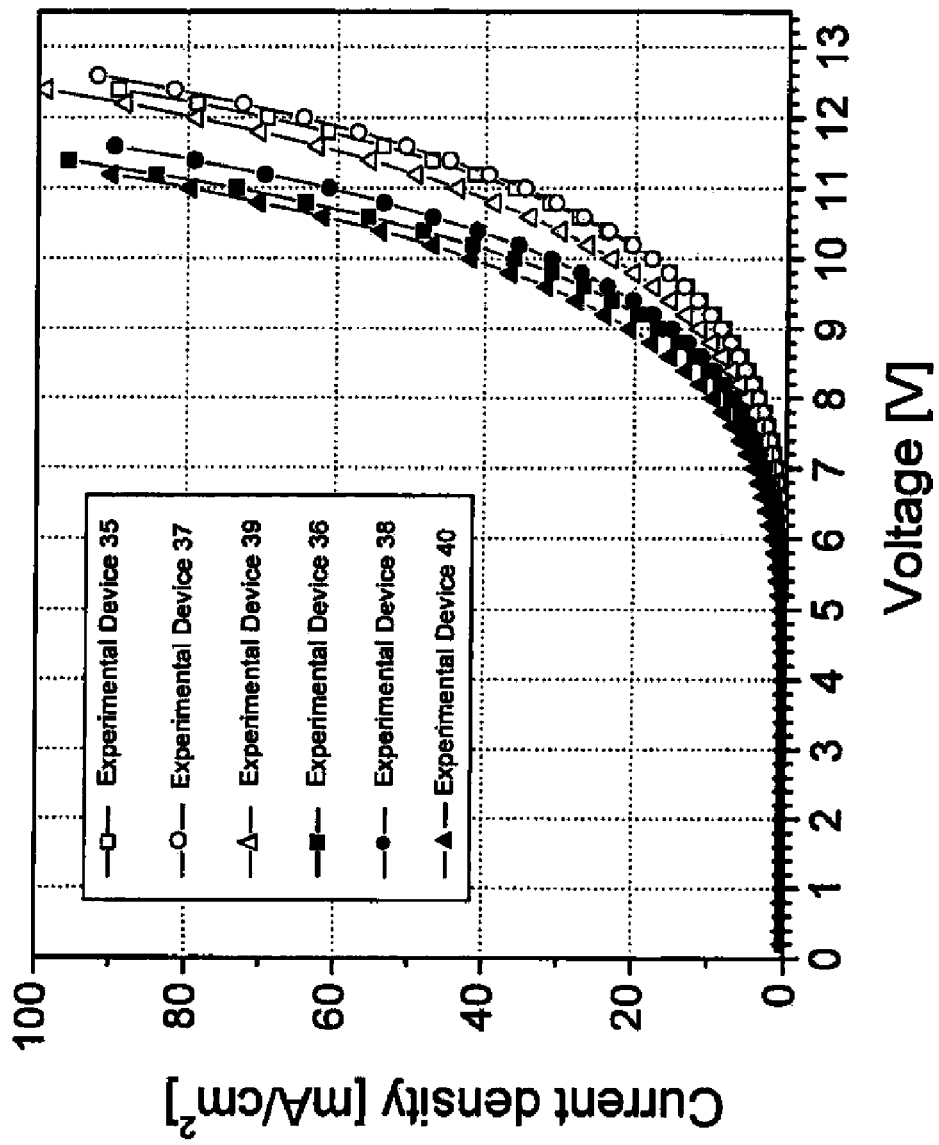
Figure 35. Current Density vs. Voltage

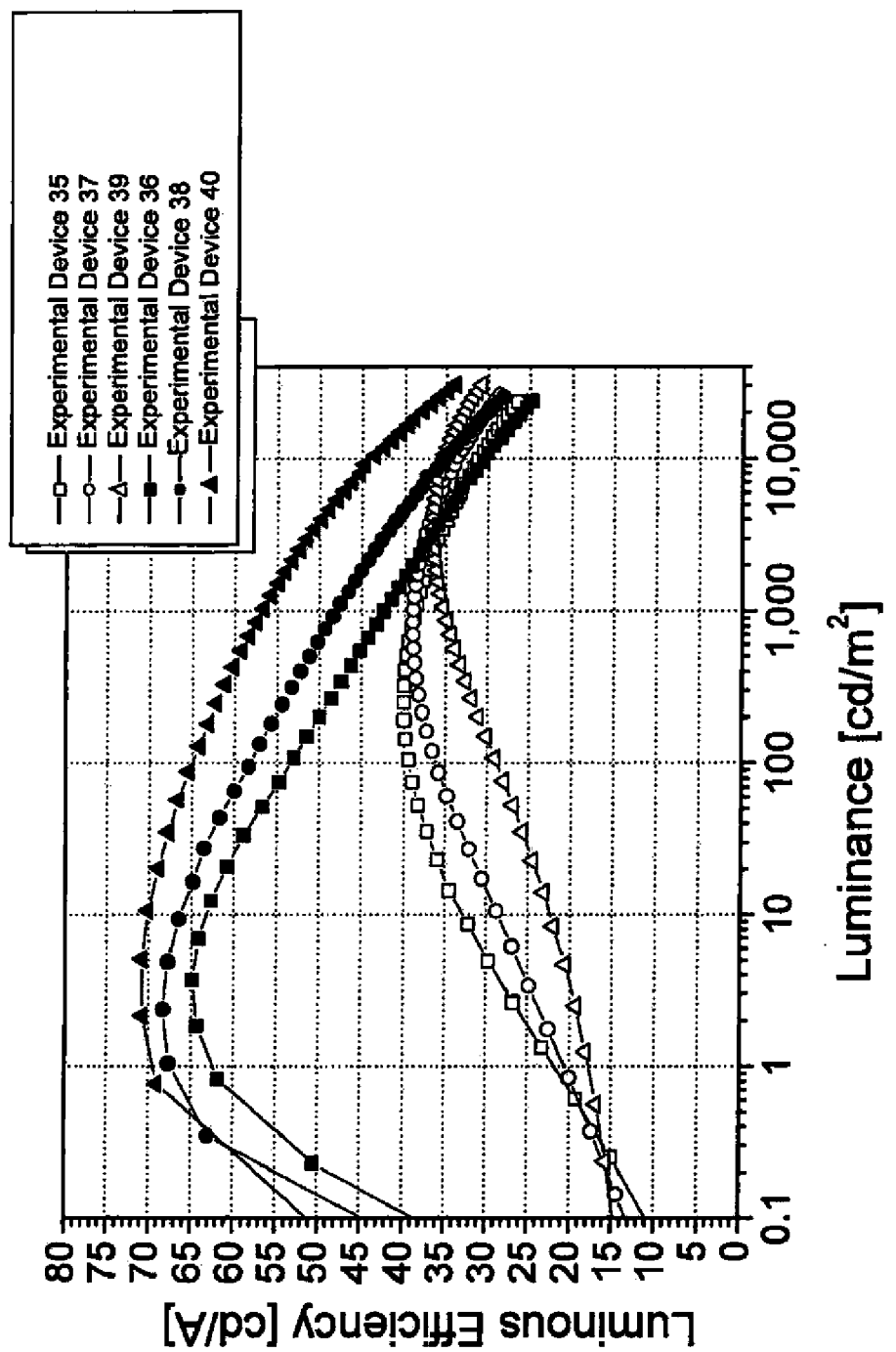
Figure 36. Luminous efficiency vs. luminance

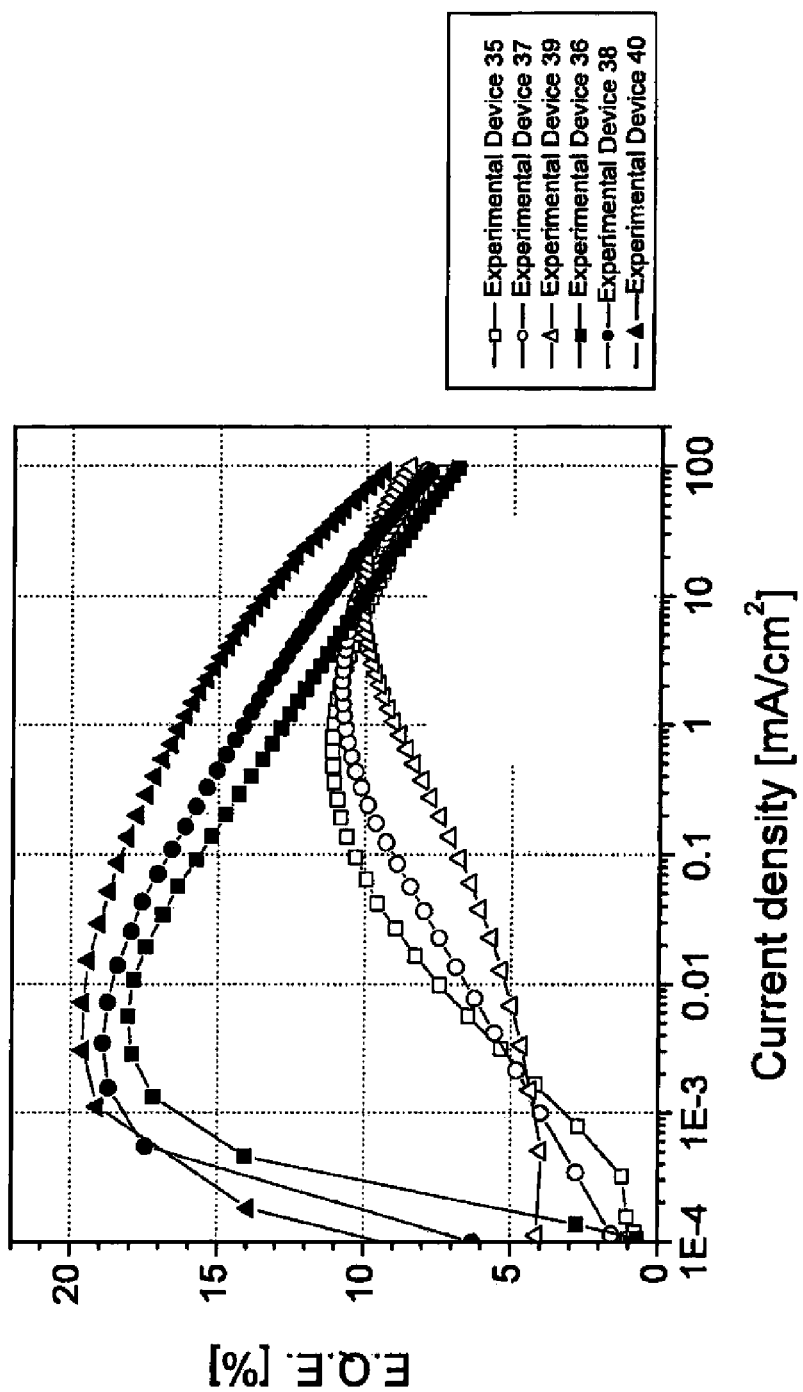
Figure 37. External quantum efficiency vs. current density

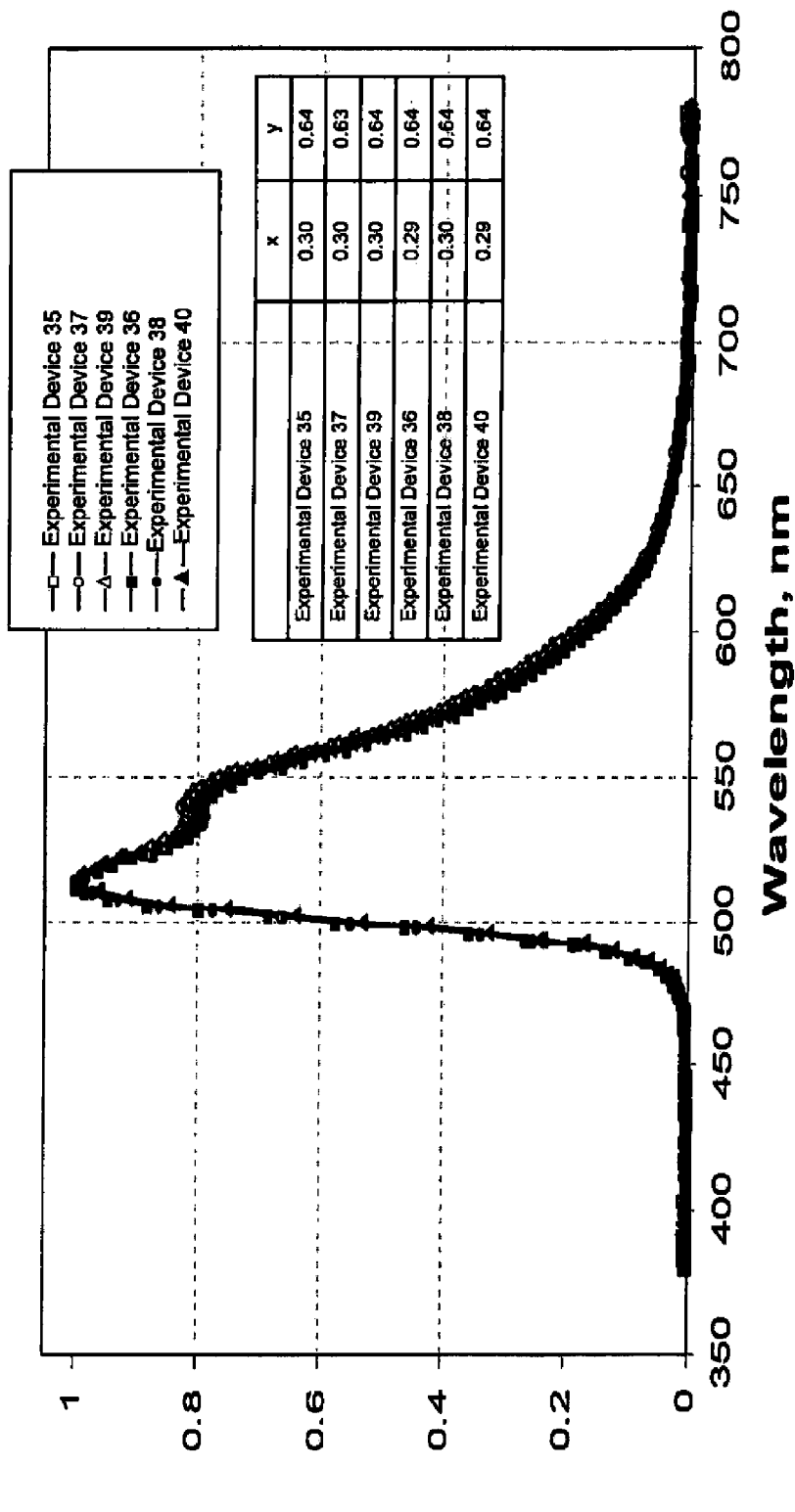
Figure 38. Electroluminescence spectra and CIE coordinates at 10 mA/cm²

ELECTROLUMINESCENT EFFICIENCY

REFERENCE TO RELATED APPLICATION

This application is a continuation-in-part of U.S. patent application Ser. No. 10/886,367 filed Jul. 7, 2004, now abandoned, which is incorporated by reference in its entirety herein.

FIELD OF THE INVENTION

The present invention relates to organic light emitting devices (OLEDs), and more specifically to phosphorescent organic materials used in such devices. More specifically, the present invention relates to phosphorescent emitting materials with improved electroluminescent efficiency when incorporated into an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic device. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As use herein, a first "Highest Occupied Molecular Orbital" (HOMO) or "Lowest Unoccupied Molecular Orbital" (LUMO) energy level is "greater than" a second HOMO or LUMO energy level if the first energy level is closer to the vacuum energy level. Since ionization potentials (IP) are measured as a negative energy relative to a vacuum level, a greater HOMO corresponds to an IP having a smaller absolute value (an IP that is less negative). Similarly, a greater LUMO corresponds to an electron affinity (EA) having a smaller absolute value (an EA that is less negative). On a conventional energy level diagram, with the vacuum level at the top, the LUMO of a material is higher than the HOMO of the same material. A "greater" HOMO or LUMO appears closer to the top of such a diagram than a "lesser" HOMO or LUMO.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

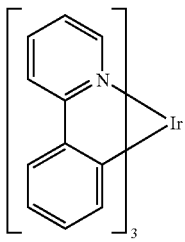

In this, and later figures herein, the dative bond from nitrogen to metal (here, Ir) is depicted in metal complexes as a straight line. Ir(ppy)$_3$ emits a spectrum at CIE 0.30, 0.63, and has a half-life of about 10,000 hours at an initial luminance of 500 cd/m$^2$, and a quantum efficiency of about 6%. Kwong et al., *Appl. Phys. Lett.*, 81, 162 (2002).

Industry standards call for the lifetime of full color displays to be at least about 5000 hours. In addition, high stability and efficiency are important characteristics of high quality displays. These requirements have helped generate a need for phosphorescent emissive materials that exhibit longer lifetimes, higher stability, and higher efficiency in the red, green and blue wavelength regimes than have been achieved in the prior art. Phosphorescent materials with improved device efficiency and stability are disclosed herein.

SUMMARY OF THE INVENTION

An organic light emitting device is provided. The device has an anode, a cathode, and an emissive layer disposed between the anode and the cathode. The emissive layer further comprises an emissive material having the structure:

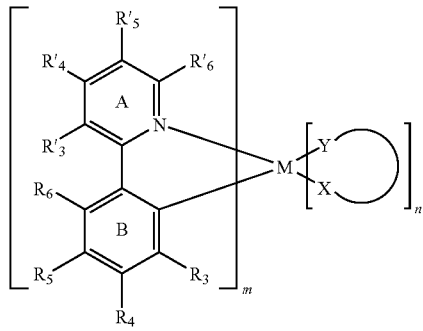

Wherein

M is a metal selected from Ir, Pt, Rh or Pd;

m is a value from 1 to the maximum number of ligands that may be attached to the metal;

m+n is the maximum number of ligands that may be attached to the metal;

(X-Y) is an ancillary ligand;

ring A is an aromatic heterocyclic or a fused aromatic heterocyclic ring having an alkyl substituent at the $R'_5$ position and having at least one nitrogen atom, N, that is coordinated to the metal M, wherein the ring A can be optionally substituted with one or more substituents at the $R'_3$, $R'_4$ and $R'_6$ positions;

additionally or alternatively the $R'_3$ and $R'_4$ substituted positions on ring A together form, independently a fused ring, wherein the fused ring may be optionally substituted;

ring B is an aromatic ring with at least one carbon atom coordinated to metal M, wherein ring B can be optionally substituted with one or more substituents at the $R_3$, $R_4$, $R_5$, and $R_6$ positions;

$R'_3$, $R'_4$ and $R'_6$ are each independently H, alkyl, alkenyl, alkynyl, heteroalkyl, alkenyl, alkynyl, heteroalkyl, aryl, heteroaryl, aralkyl; and wherein $R'_3$, $R'_4$ and $R'_6$ are optionally substituted by one or more substituents Z; and $R_3$, $R_4$, $R_5$ and $R_6$ are each independently selected from the group consisting of H, alkyl, alkenyl, alkynyl, alkylaryl, CN, $CO_2R$, $C(O)R$, $NR_2$, $NO_2$, OR, halo, aryl, heteroaryl, substituted aryl, substituted heteroaryl or a heterocyclic group such that when $R'_3$, $R'_4$, and $R'_6$ are all H, $R_3$, $R_4$, $R_5$ and $R_6$ are also all H or at least one of $R_4$, $R_5$ and $R_6$ is a linking group covalently linking two or more of the maximum number of ligands that may be attached to the metal, an unsubstituted phenyl ring, a fluoro-substituted phenyl ring or a phenyl ring substituted with a substituent that renders the phenyl ring equally or less coplanar than the unsubstituted phenyl ring with respect to Ring B;

alternatively, $R'_3$ and $R_6$ may be bridged by a group selected from —$CR_2$—$CR_2$—, —CR=CR—, —$CR_2$—, —O—, —NR—, —O—$CR_2$—, —NR—$CR_2$—, and —N=CR—;

each R is independently H, alkyl, alkenyl, alkynyl, heteroalkyl, aryl, heteroaryl, or aralkyl; wherein R is optionally substituted by one or more substituents Z;

each Z is independently a halogen, R', O R', N(R')$_2$, S R', C(O)R', C(O)O R', C(O)N(R')$_2$, CN, SO$_2$, SO R', SO$_2$ R', or SO$_3$ R'; and each R' is independently H, alkyl, alkenyl, alkynyl, heteroalkyl, aryl, or heteroaryl;

The emissive material itself is also provided. The emissive material may have improved efficiency and stability when incorporated into a light emitting device. In particular, the devices of the present invention may exhibit dramatically improved efficiency over known devices.

Although not shown here, experimental data was obtained demonstrating normalized electroluminescence spectra (normalized EL intensity vs. wavelength) at a current density of 10mA/cm² for Experimental devices 12-16 using fac-tris [3-methyl-5,6-dihydrobenzo[h]quinolinato-N,C2'] iridium (III) (Compound Example V) as the emissive material doped at 6%-10% in CBP.

Figure 17:
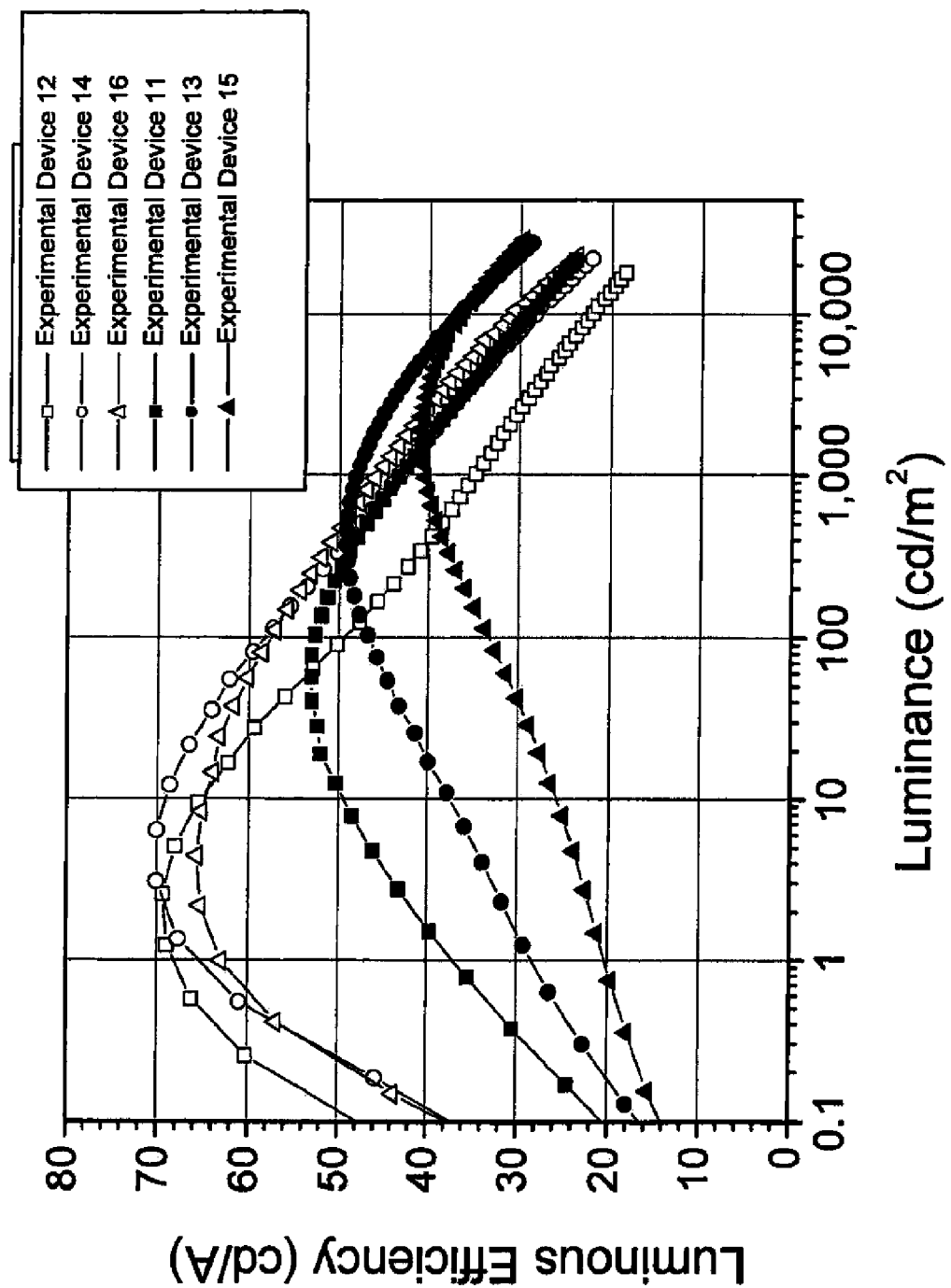

FIG. 17 shows the plots of luminous efficiency (cd/A) vs. brightness (cd/m²) comparing devices with either 100 Å of aluminum(III)bis(2-methyl-8-hydroxyquinolinato) 4-phenylphenolate (BAlq) as the ETL2 (Experimental Devices 11, 13 and 15) or 50 Å of HPT as the ETL2 (Experimental Devices 12, 14 and 16) using fac-tris [3-methyl-5,6-dihydrobenzo[h]quinolinato-N,C2'] iridium(III) (Compound Example V) as the emissive material doped at 6%-10% in CBP.

Figure 18:
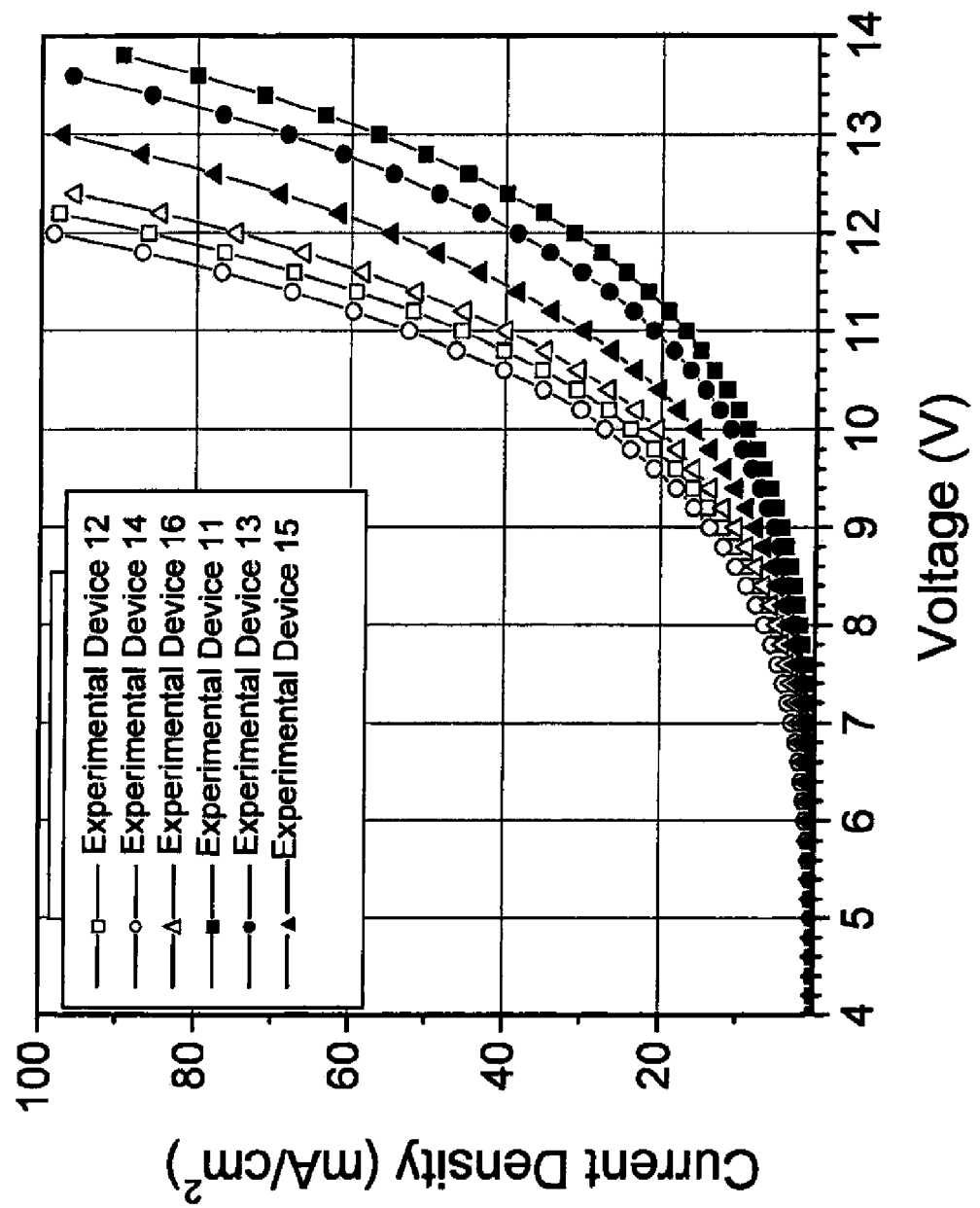

FIG. 18 shows the plots of the current density (mA/cm²) vs. the voltage (V) comparing devices with either 100 Å of aluminum(III)bis(2-methyl-8-hydroxyquinolinato) 4-phenylphenolate (BAlq) as the ETL2 (Experimental Devices 11, 13 and 15) or 50 Å of HPT as the ETL2 (Experimental Devices 12,14, and 16) using fac-tris [3-methyl-5,6-dihydrobenzo [h]quinolinato-N,C2'] iridium(III) (Compound Example V) as the emissive material doped at 6%-10% in CBP.

Figure 19:
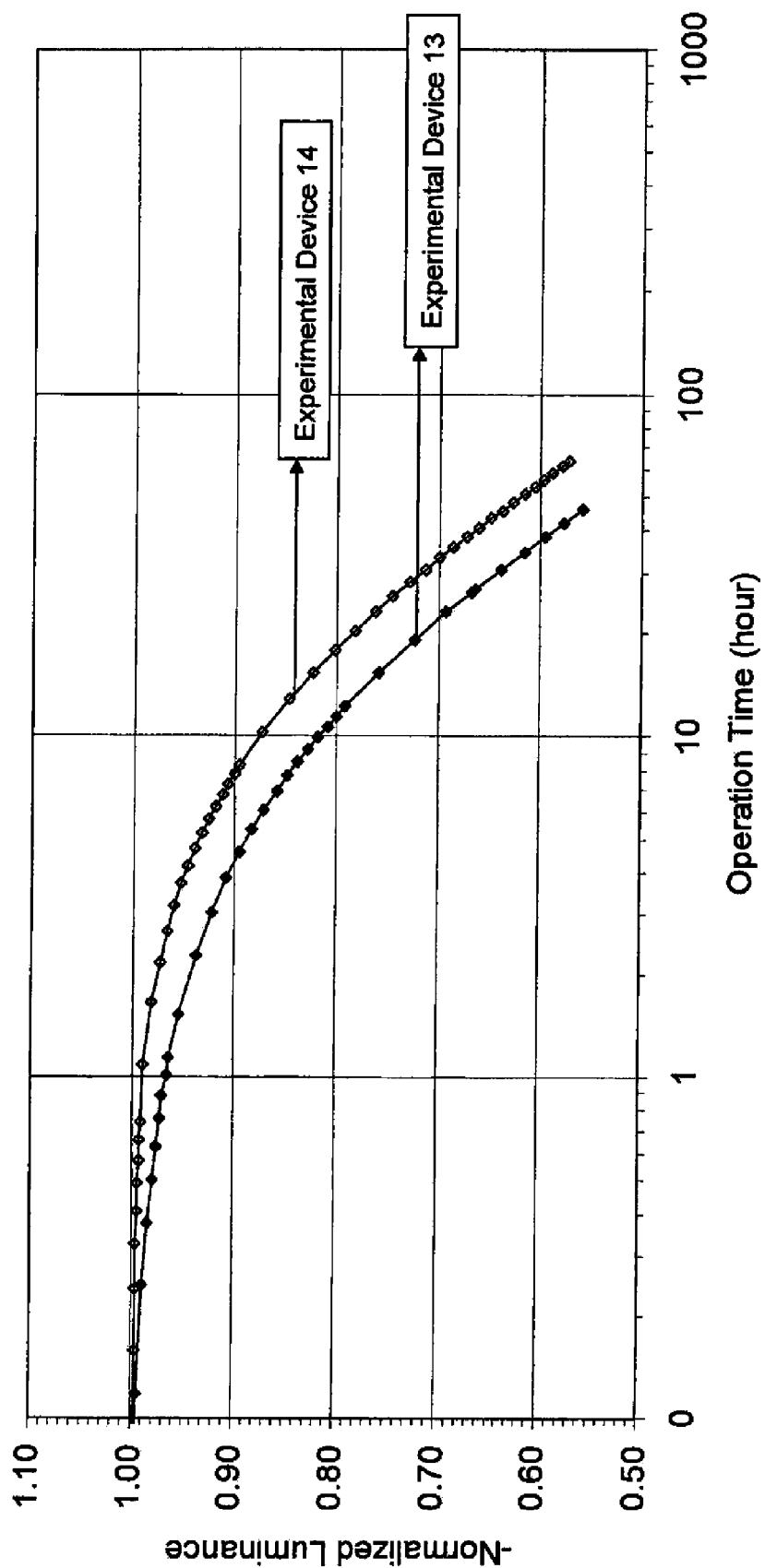

FIG. 19 shows the normalized luminance decay for Experimental Devices 13 and 14.

Figure 20:
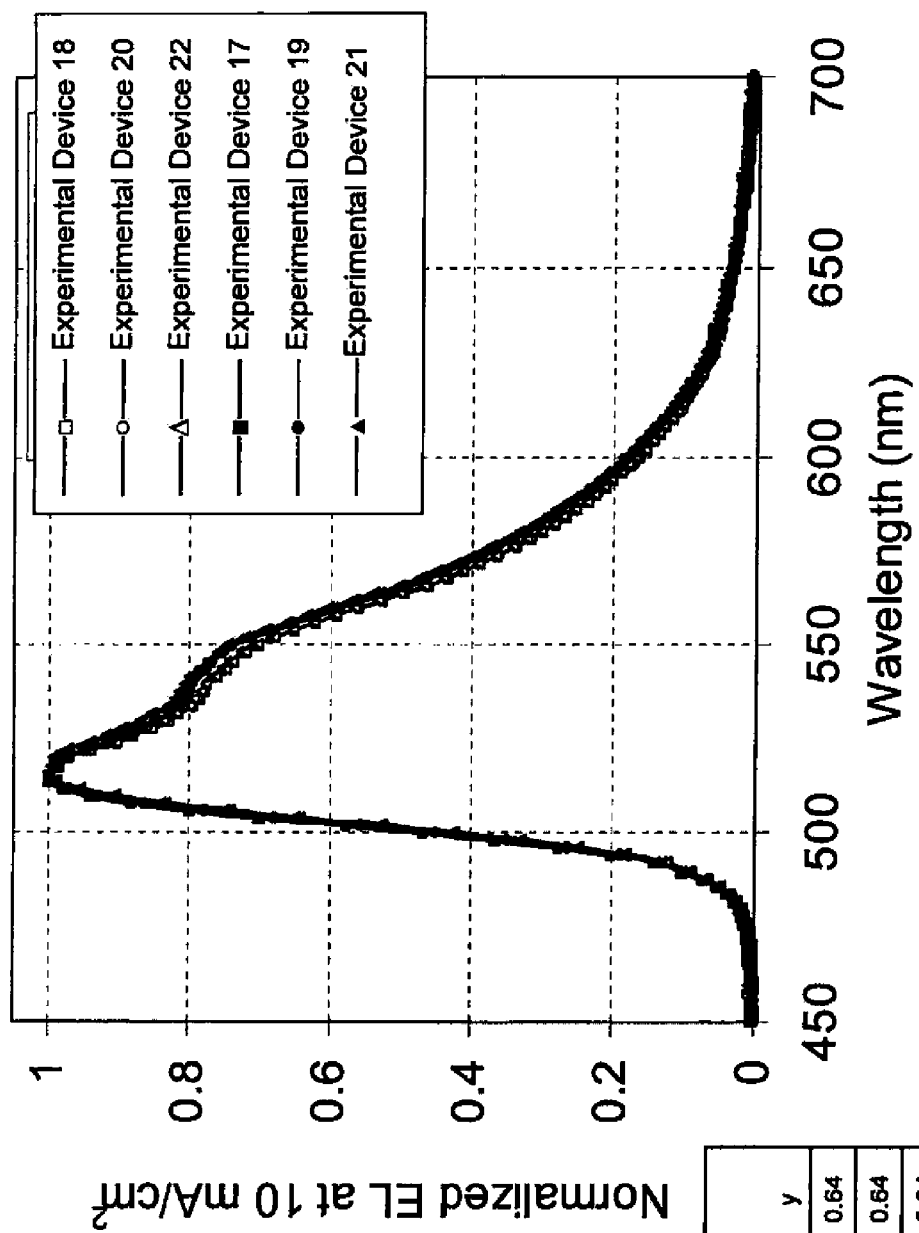

FIG. 20 shows the normalized electroluminescence spectra (normalized EL intensity vs. wavelength) at a current density of 10mA/cm² for Experimental Devices 18-22using fac-tris [2-(2'-methylbiphenyl-3-yl)pyridinato-N,C²] iridium(III) (Compound Example VI) in the emissive layer doped at 6%-12% in CBP.

Although not shown here, experimental data was obtained demonstrating luminous efficiency (cd/A) vs. brightness (cd/m²) for devices Experimental Devices 18-22 comparing devices with either 100 Å of aluminum(III)bis(2-methyl-8-hydroxyquinolinato)4-phenylphenolate (BAlq) as the ETL2 (Experimental Devices 17, 19 and 21) or 50 Å of HPT as the ETL2 (Experimental Devices 18,20, and 22) using fac-tris[2-(2'-methylbiphenyl-3-yl)pyridinato-N,C²]iridium(III) (Compound Example VI) as the emissive material doped at 6%-12% in CBP.

Figure 21:
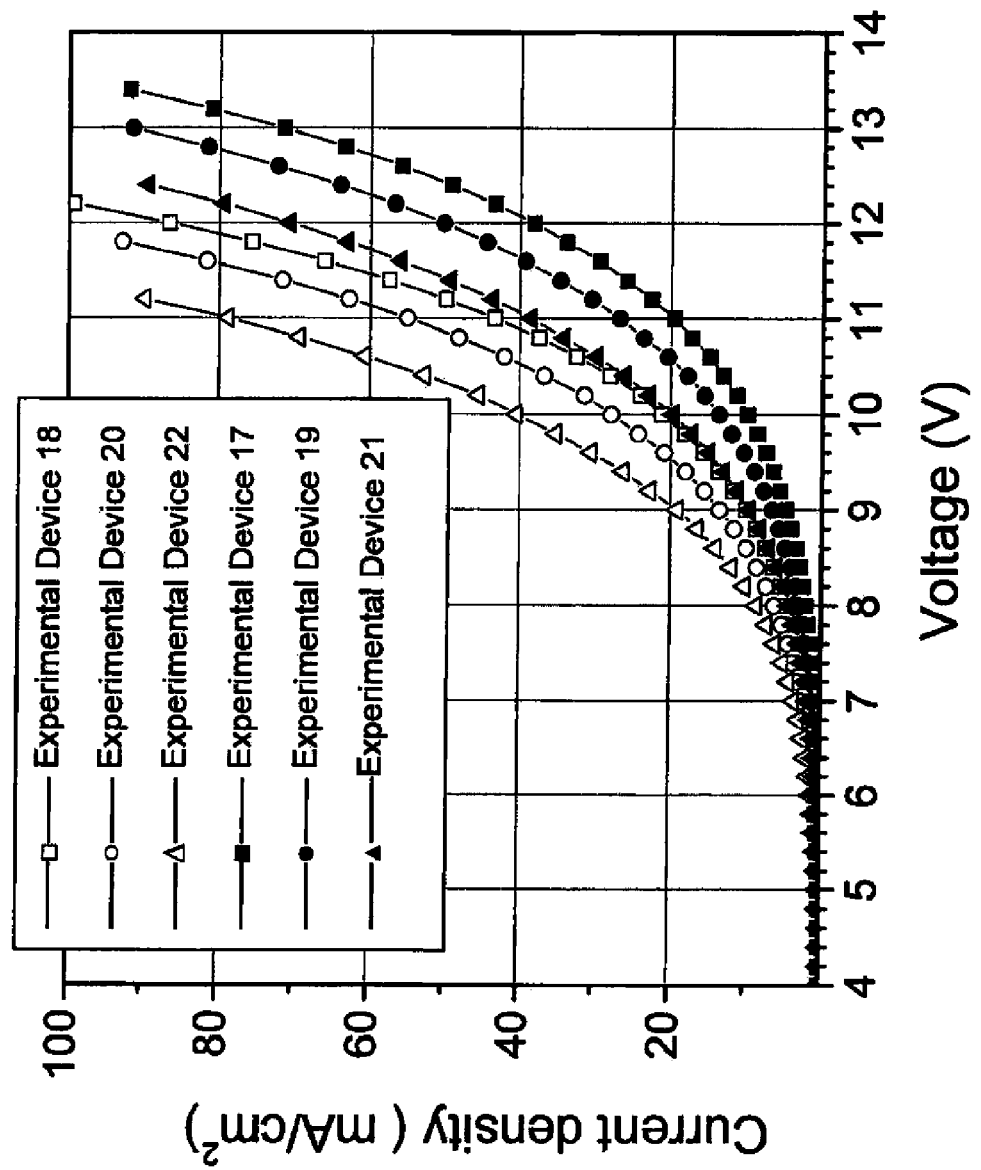

FIG. 21 shows the plots of the current density (mA/cm²) vs. the voltage (V) comparing devices with either 100 Å of aluminum(III)bis(2-methyl-8-hydroxyquinolinato) 4-phenylphenolate (BAlq) as the ETL2 (Experimental Devices 17, 19 and 21) or 50 Å of HPT as the ETL2 (Experimental Devices 18,20, and 22) using fac-tris[2-(2'-methylbiphenyl-3-yl)pyridinato-N,C²] iridium(III) (Compound Example VI)as the emissive material doped at 6%-12% in CBP.

Figure 22:
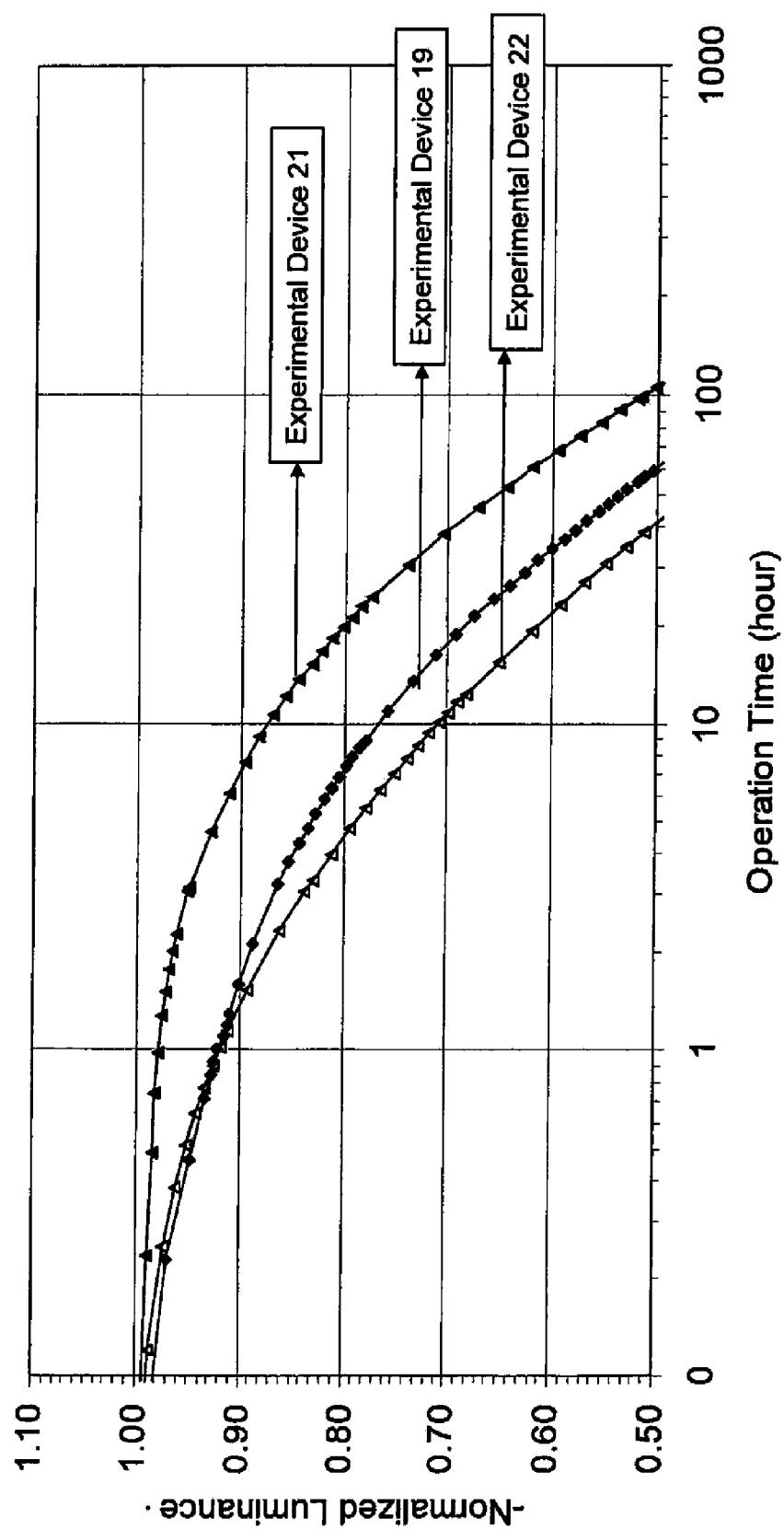

FIG. 22 shows the normalized luminance as a function of time at a current density of 40 mA/cm² for annealed Experimental Devices 19, 21 and 22.

Figure 23:
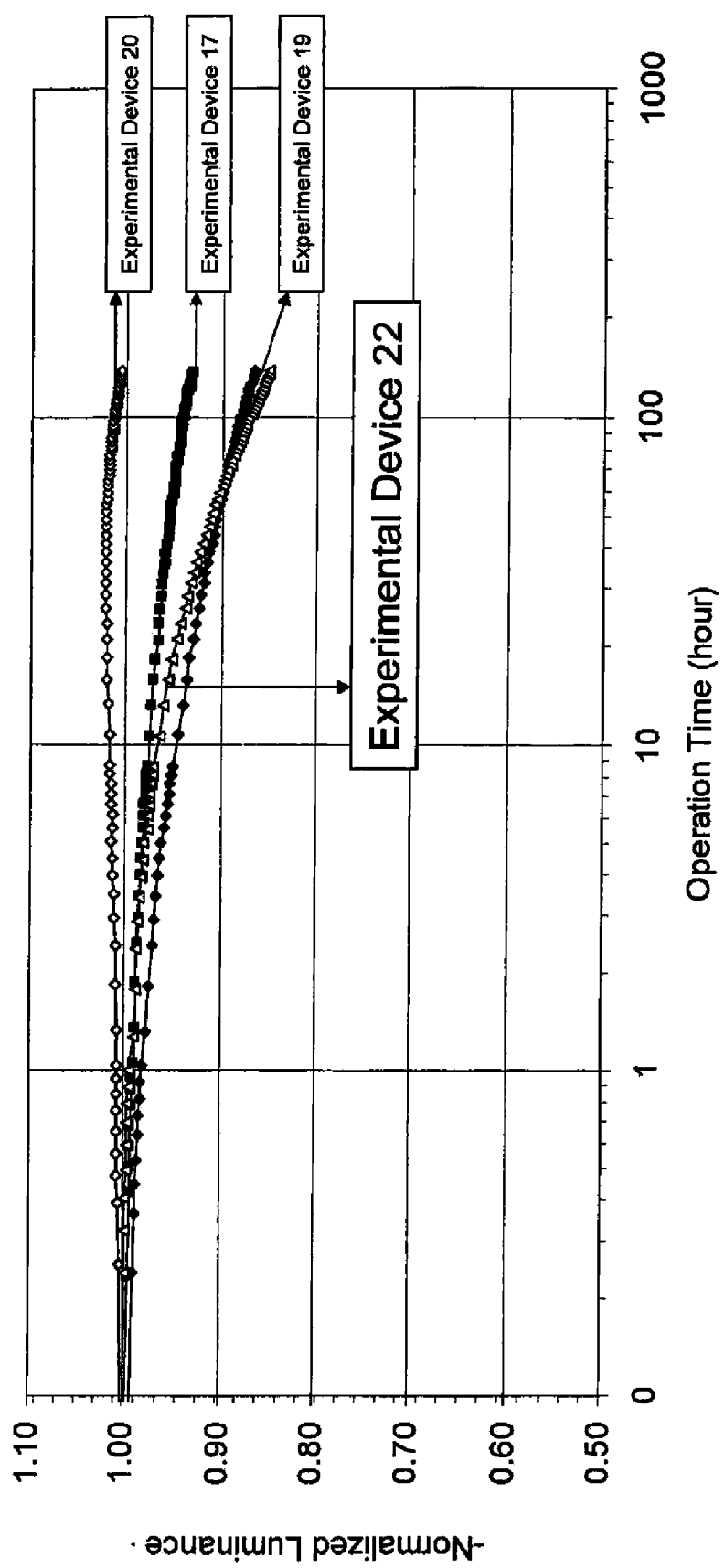

FIG. 23 shows the normalized luminance as a function of time at an initial luminance of 1000 cd/m² for Experimental Devices 17, 19, 20 and 22.

Figure 24:
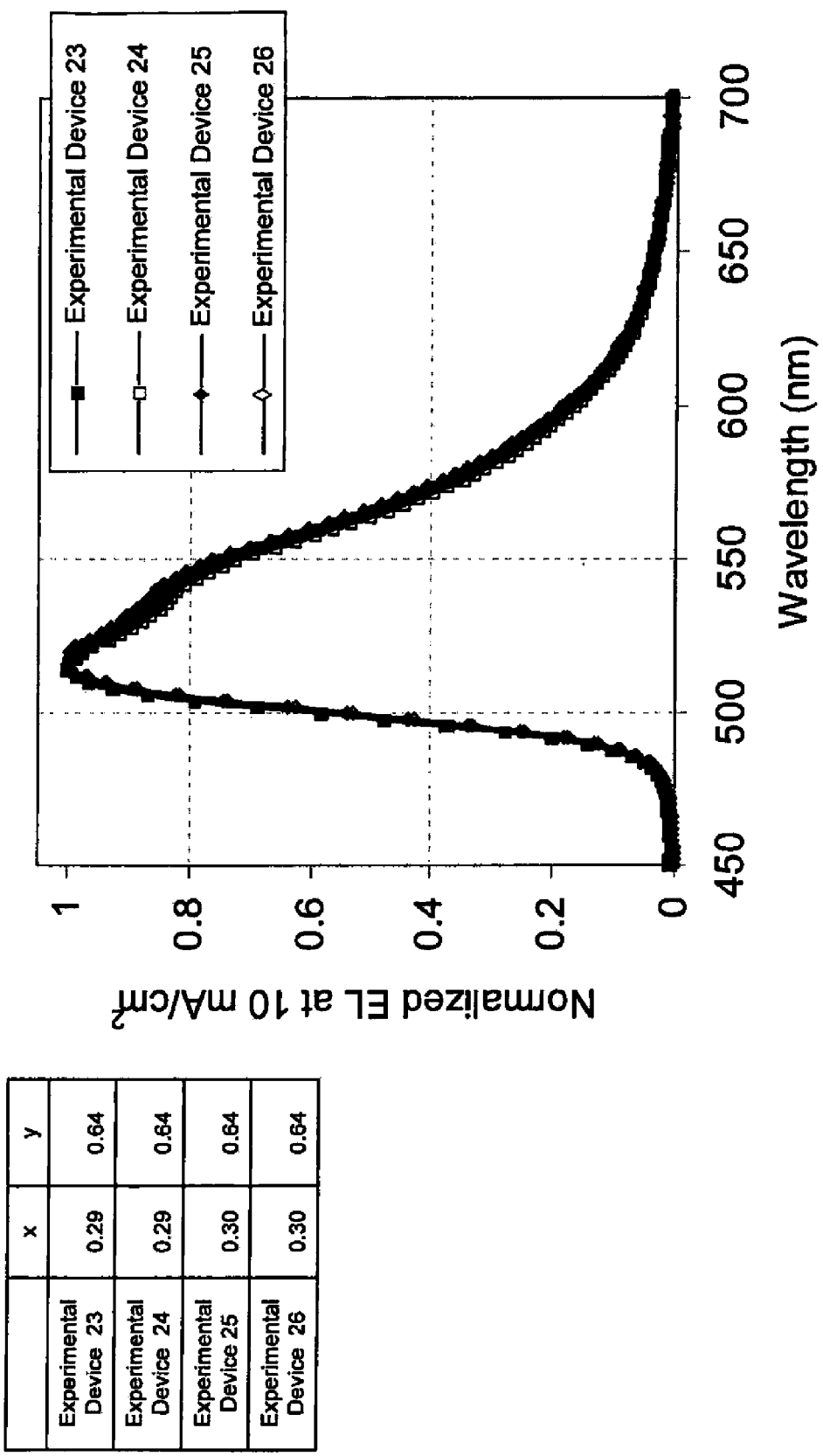

FIG. 24 shows the normalized electroluminescence spectra (normalized EL intensity vs. wavelength) at a current density of 10mA/cm$^2$ for Experimental Devices 23-26using a Hexadentate Ligand Complex (Compound Example VII) as the emissive material in the emissive layer doped at 6%-10% in CBP.

Figure 25:
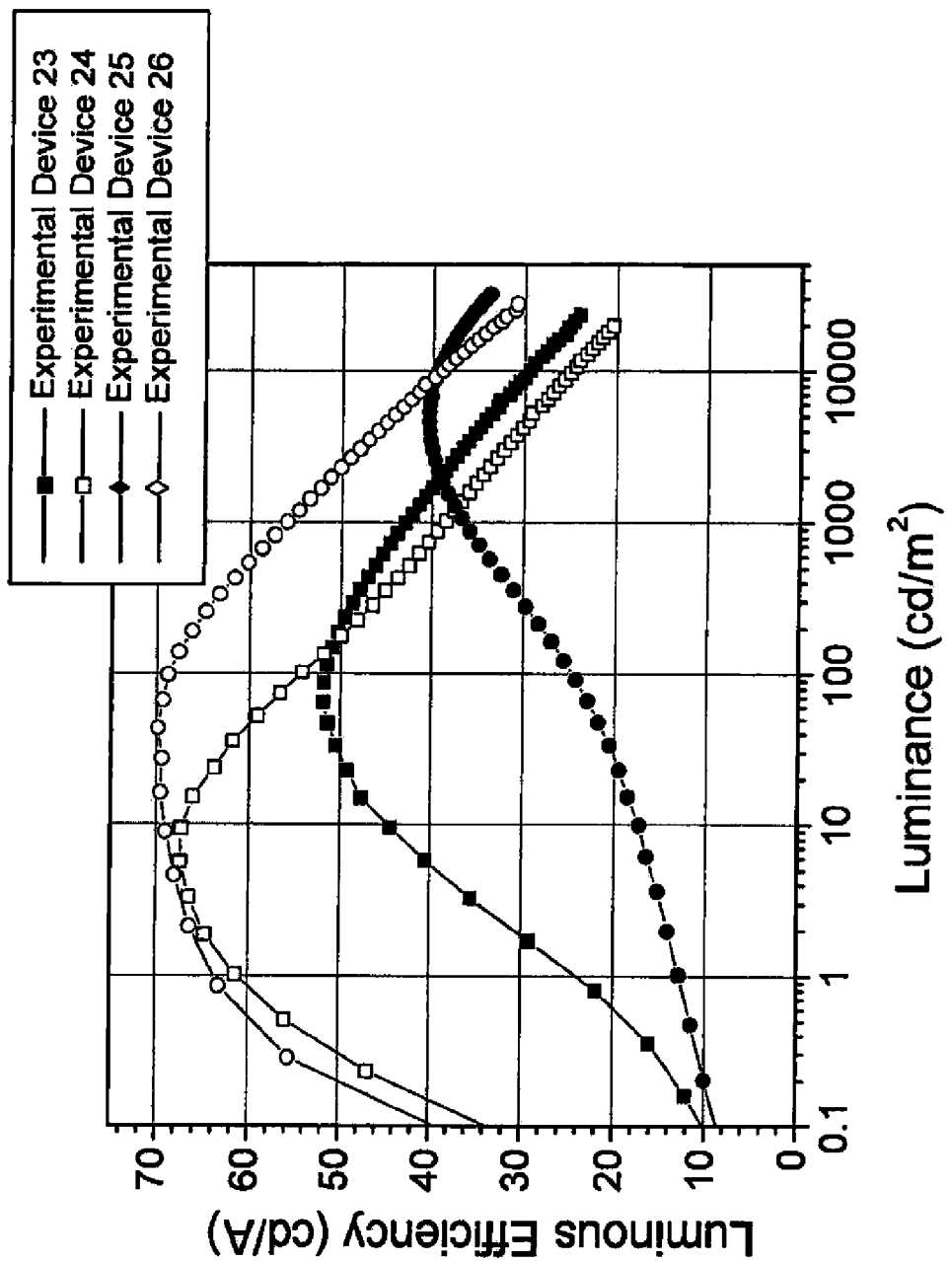

FIG. 25 shows the plots of luminous efficiency (cd/A) vs. brightness (cd/m$^2$) comparing devices with either 100 Å of aluminum(III)bis(2-methyl-8-hydroxyquinolinato) 4-phenylphenolate (BAlq) as the ETL2 (Experimental Devices 23 and 25) or 50 Å of HPT as the ETL2 (Experimental Devices 24 and 26) using a Hexadentate Ligand Complex (Compound ExampleVII) as the emissive material in the emissive layer doped at 6%-10% in CBP.

Figure 26:
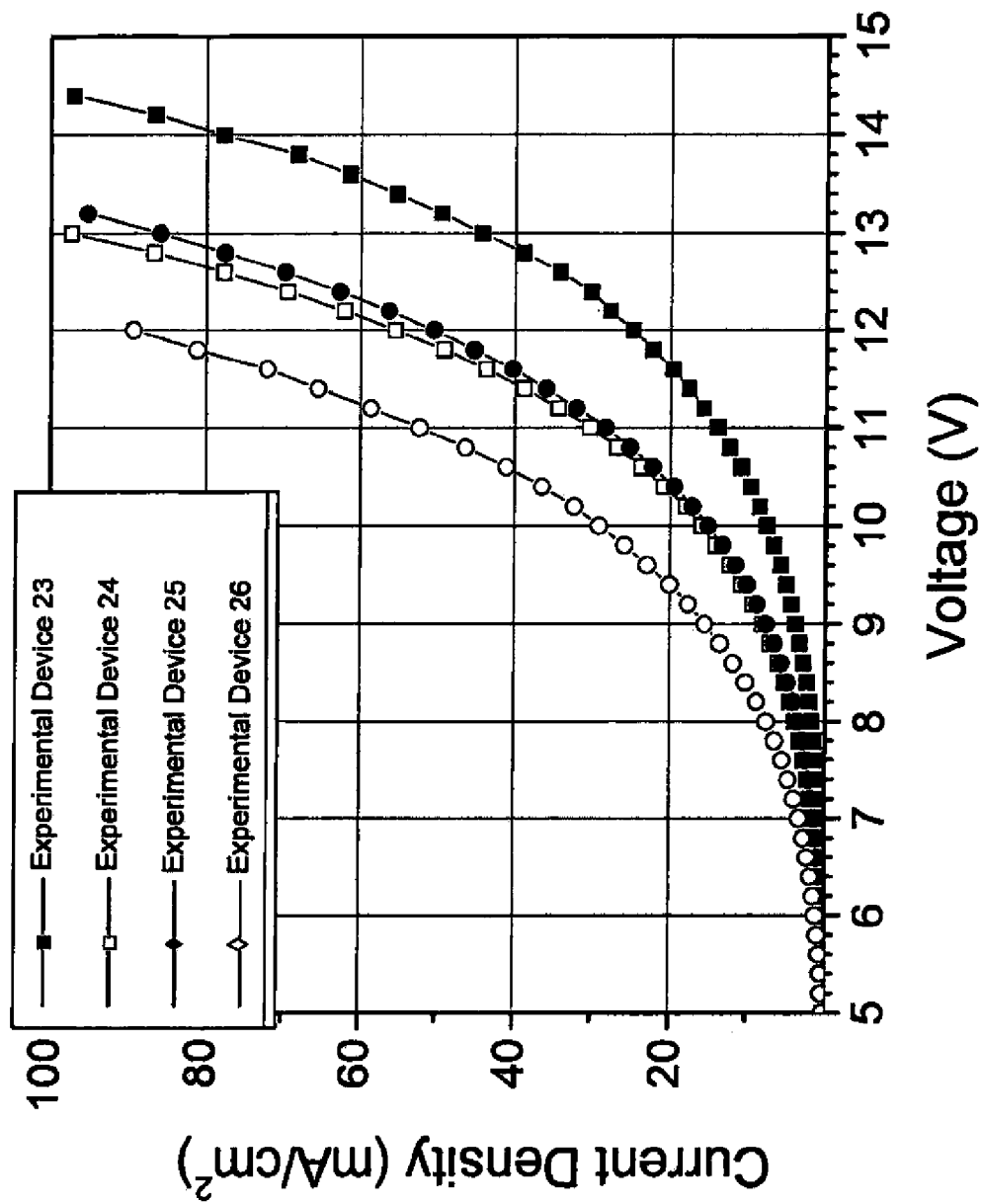

FIG. 26 shows the plots of the current density (mA/cm$^2$) vs. the voltage (V) comparing devices with either 100 Å of aluminum(III)bis(2-methyl-8-hydroxyquinolinato) 4-phenylphenolate (BAlq) as the ETL2 (Experimental Devices 23 and 25) or 50 Å of HPT as the ETL2 (Experimental Devices 24 and 26) using a Hexadentate Ligand Complex (Compound ExampleVII) as the emissive material in the emissive layer doped at 6%-10% in CBP.

Figure 27:
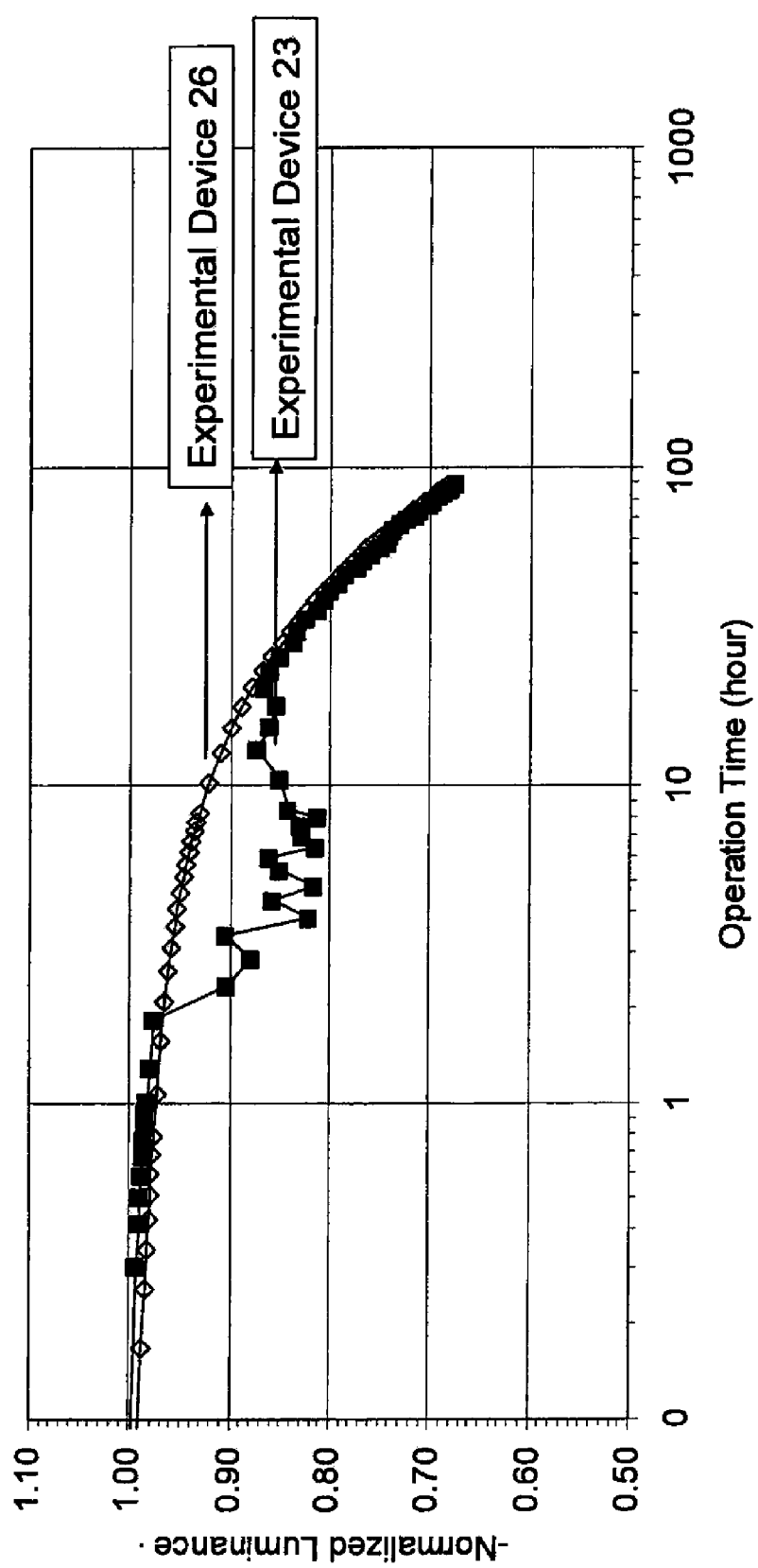

FIG. 27 shows the normalized luminance as a function of time at a current density of 40 mA/cm$^2$ for Experimental Devices 23 and 26.

Figure 28:
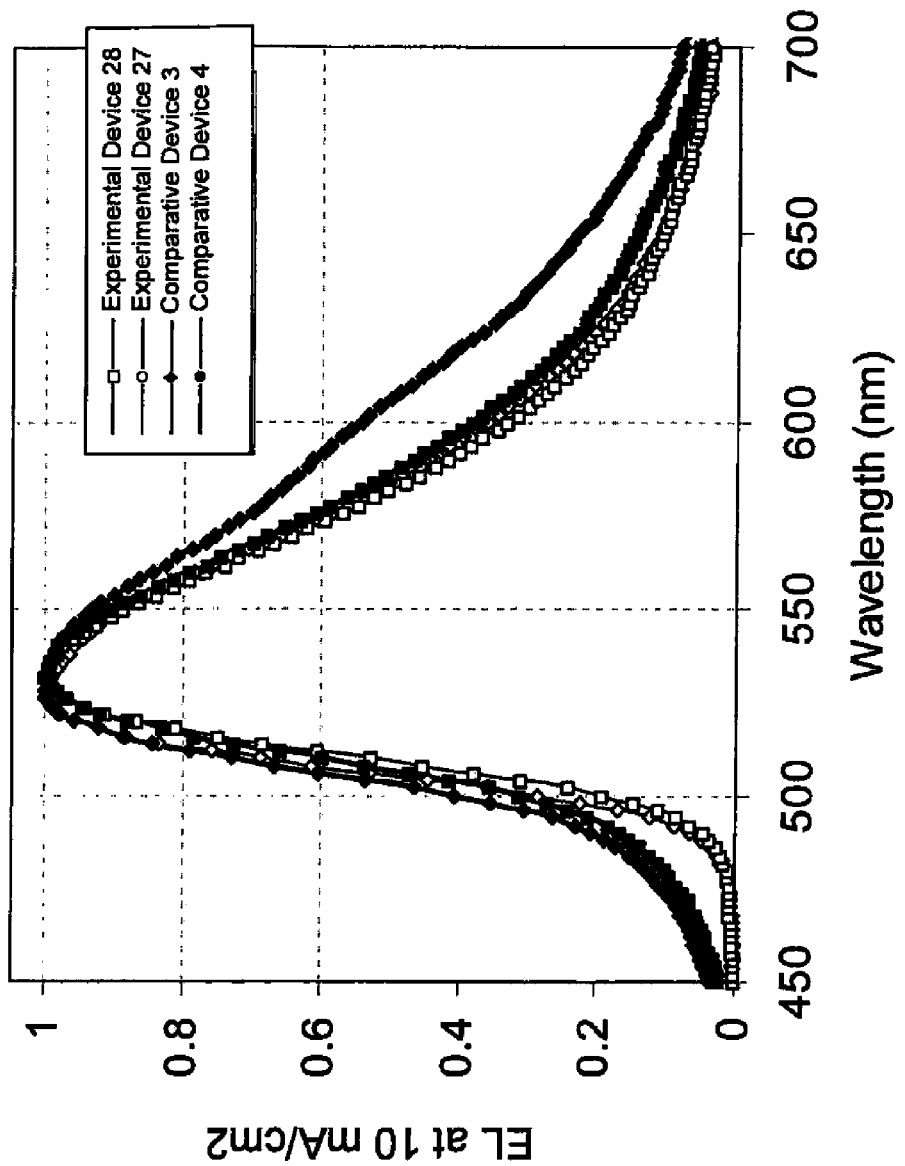

FIG. 28 shows the normalized electroluminescence spectra (normalized EL intensity vs. wavelength) at a current density of 10mA/cm$^2$ in Experimental Devices 27 and 28 having a neat layer of fac-tris[2-(2'-methylbiphenyl-3-yl)pyridinato-N,C$^2$]iridium(III) (Compound Example VI) as the emissive layer and Comparative Example Devices 3 and 4 having a neat layer of Ir(3'-Meppy)$_3$ as the emissive layer comparing devices with either 100 Å of aluminum(III)bis(2-methyl-8-hydroxyquinolinato)4-phenylphenolate (BAlq) as the ETL2 (Experimental Device 27 and Comparative Example Device 3) or 50 Å of HPT as the ETL2 (Experimental Device 28 and Comparative Example Device 4)

Figure 29:
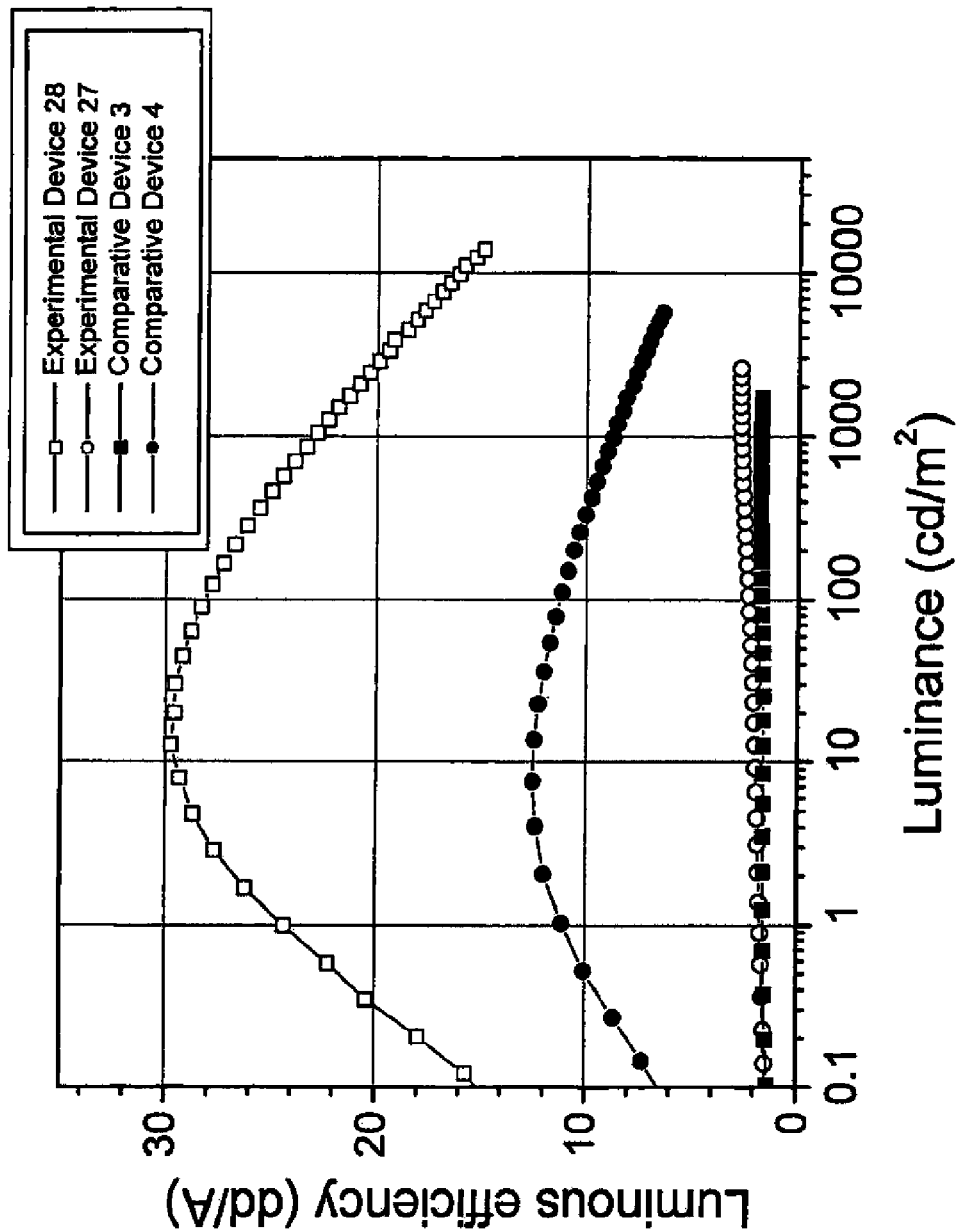

FIG. 29 shows the plots of luminous efficiency (cd/A) vs. brightness (cd/m$^2$) voltage comparing devices having neat emissive layers with either 100 Å of aluminum(III)bis(2-methyl-8-hydroxyquinolinato)4-phenylphenolate (BAlq) as the ETL2 (Experimental Device 27 and Comparative Example Device 3) or 50 Å of HPT as the ETL2 (Experimental Device 28 and Comparative Example Device 4).

Figure 30:
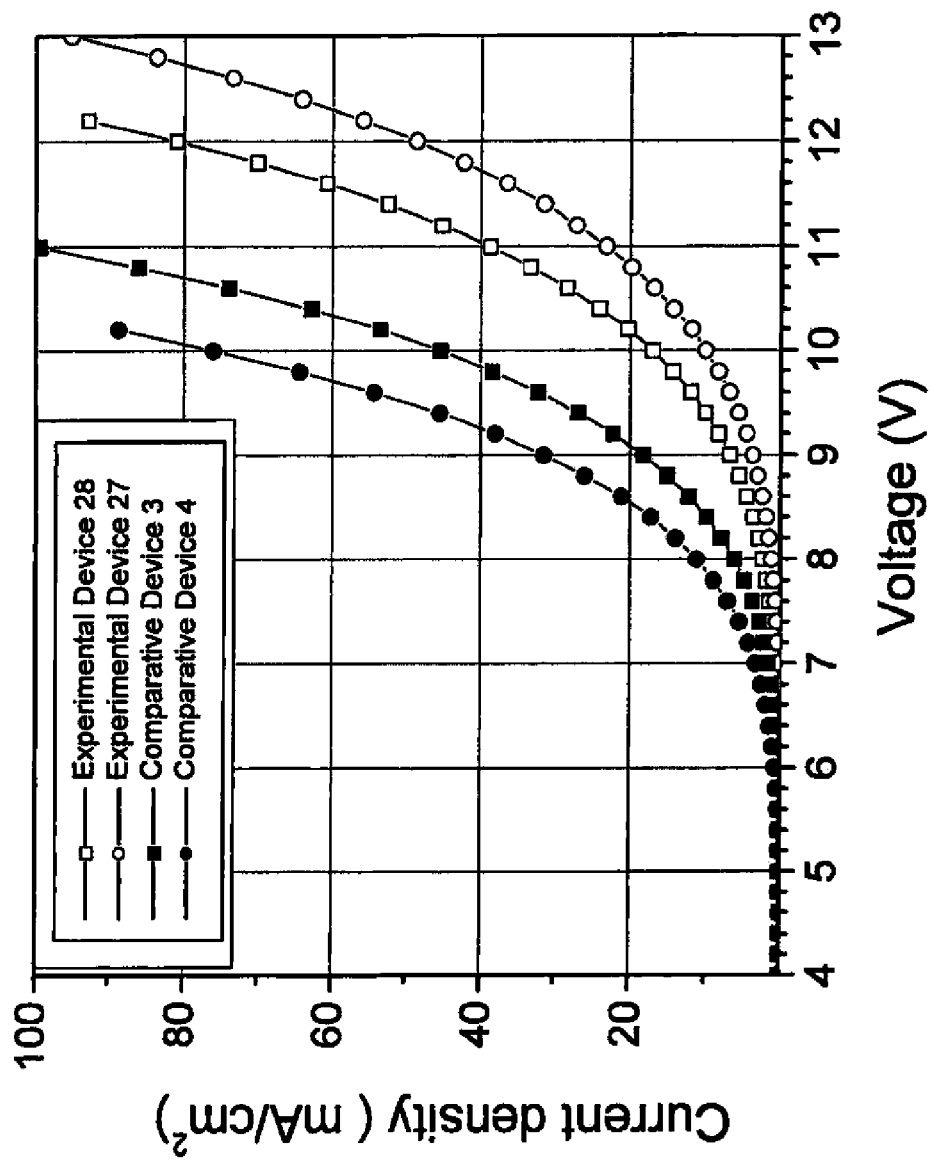

FIG. 30 shows the plots of the current density (mA/cm$^2$) vs. the voltage (V) having neat emissive layers with either 100 Å of aluminum(III)bis(2-methyl-8-hydroxyquinolinato) 4-phenylphenolate (BAlq) as the ETL2 (Experimental Device 27 and Comparative Example Device3) or 50 Å of HPT as the ETL2 (Experimental Device 28 and Comparative Example Device4).

FIG. 31 shows the plots of the current density (mA/cm$^2$) vs. the voltage (V) comparing devices with either 100 Å of aluminum(III)bis(2-methyl-8-hydroxyquinolinato) 4-phenylphenolate (BAlq) as the ETL2 (Experimental Devices 29, 31 and 33) or 50 Å of HPT as the ETL2 (Experimental Devices 30, 32 and 34) using Ir[5'-Me-5-(4-FPh)ppy]$_3$ (Compound Example VIII) as the emissive material in the emissive layer doped at 6%, 8% and 10% in CBP.

FIG. 32 shows the plots of the luminous efficiency (cd/A) vs. brightness (cd/m$^2$) comparing devices with either 100 Å of aluminum(III)bis(2-methyl-8-hydroxyquinolinato) 4-phenylphenolate (BAlq) as the ETL2 (Experimental Devices 29, 31 and 33) or 50 Å of HPT as the ETL2 (Experimental Devices 30, 32 and 34) using Ir[5'-Me-5-(4-FPh)ppy]$_3$ (Compound Example VIII) as the emissive material in the emissive layer doped at 6%, 8% and 10% in CBP.

FIG. 33 shows the plots of the external quantum efficiency (%) vs. current density (mA/cm$^2$) comparing devices with either 100 Å of aluminum(III)bis(2-methyl-8-hydroxyquinolinato)4-phenylphenolate (BAlq) as the ETL2 (Experimental Devices 29, 31 and 33) or 50 Å of HPT as the ETL2 (Experimental Devices 30, 32 and 34) using Ir[5'-Me-5-(4-FPh)ppy]$_3$ (Compound Example VIII) as the emissive material in the emissive layer doped at 6%, 8% and 10% in CBP.

FIG. 34 shows the normalized electroluminescence spectra (normalized EL intensity vs. wavelength) at a current density of 10 mA/cm$^2$ for Experimental Devices 29-34using Ir[5'-Me-5-(4-FPh)ppy]$_3$ (Compound Example VIII) as the emissive material in the emissive layer doped at 6%, 8% and 10% in CBP.

FIG. 35 shows the plots of the current density (mA/cm$^2$) vs. the voltage (V) comparing devices with either 100 Å of aluminum(III)bis(2-methyl-8-hydroxyquinolinato) 4-phenylphenolate (BAlq) as the ETL2 (Experimental Devices 35, 37 and 39) or 50 Å of HPT as the ETL2 (Experimental Devices 36, 38 and 40) using Ir[5'-Me-5-(3-FPh)ppy]$_3$ (Compound Example IX) as the emissive material in the emissive layer doped at 6%, 8% and 10% in CBP.

FIG. 36 shows the plots of the luminous efficiency (cd/A) vs. brightness (cd/m$^2$) comparing devices with either 100 Å of aluminum(III)bis(2-methyl-8-hydroxyquinolinato) 4-phenylphenolate (BAlq) as the ETL2 (Experimental Devices 35, 37 and 39) or 50 Å of HPT as the ETL2 (Experimental Devices 36, 38 and 40) using Ir[5'-Me-5-(3-FPh)ppy]$_3$ (Compound Example IX) as the emissive material in the emissive layer doped at 6%, 8% and 10% in CBP.

FIG. 37 shows the plots of the external quantum efficiency (%) vs. current density (mA/cm$^2$) comparing devices with either 100 Å of aluminum(III)bis(2-methyl-8-hydroxyquinolinato) 4-phenylphenolate (BAlq) as the ETL2 (Experimental Devices 35, 37 and 39) or 50 Å of HPT as the ETL2 (Experimental Devices 36, 38 and 40) using Ir[5'-Me-5-(3-FPh)ppy]$_3$ (Compound Example VIII) as the emissive material in the emissive layer doped at 6%, 8% and 10% in CBP.

FIG. 38 shows the normalized electroluminescence spectra (normalized EL intensity vs. wavelength) at a current density of 10mA/cm$^2$ for Experimental Devices 35-40using Ir[5'-Me-5-(3-FPh)ppy]$_3$ (Compound Example VIII) as the emissive material in the emissive layer doped at 6%, 8% and 10% in CBP.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238 and 6,310,360; U.S. Patent Application Publication Nos. 2002-0034656; 2002-0182441; and 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Pentice-Hall (1998). Thus, the term organometallic refers to compounds which have an organic group bonded to a metal through a carbon-metal bond. This class does not include per se coordination compounds, which are substances having only donor bonds from heteroatoms, such as metal complexes of anines, halides, pseudohalides (CN, etc.), and the like. In practice organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN.

Figure 1:
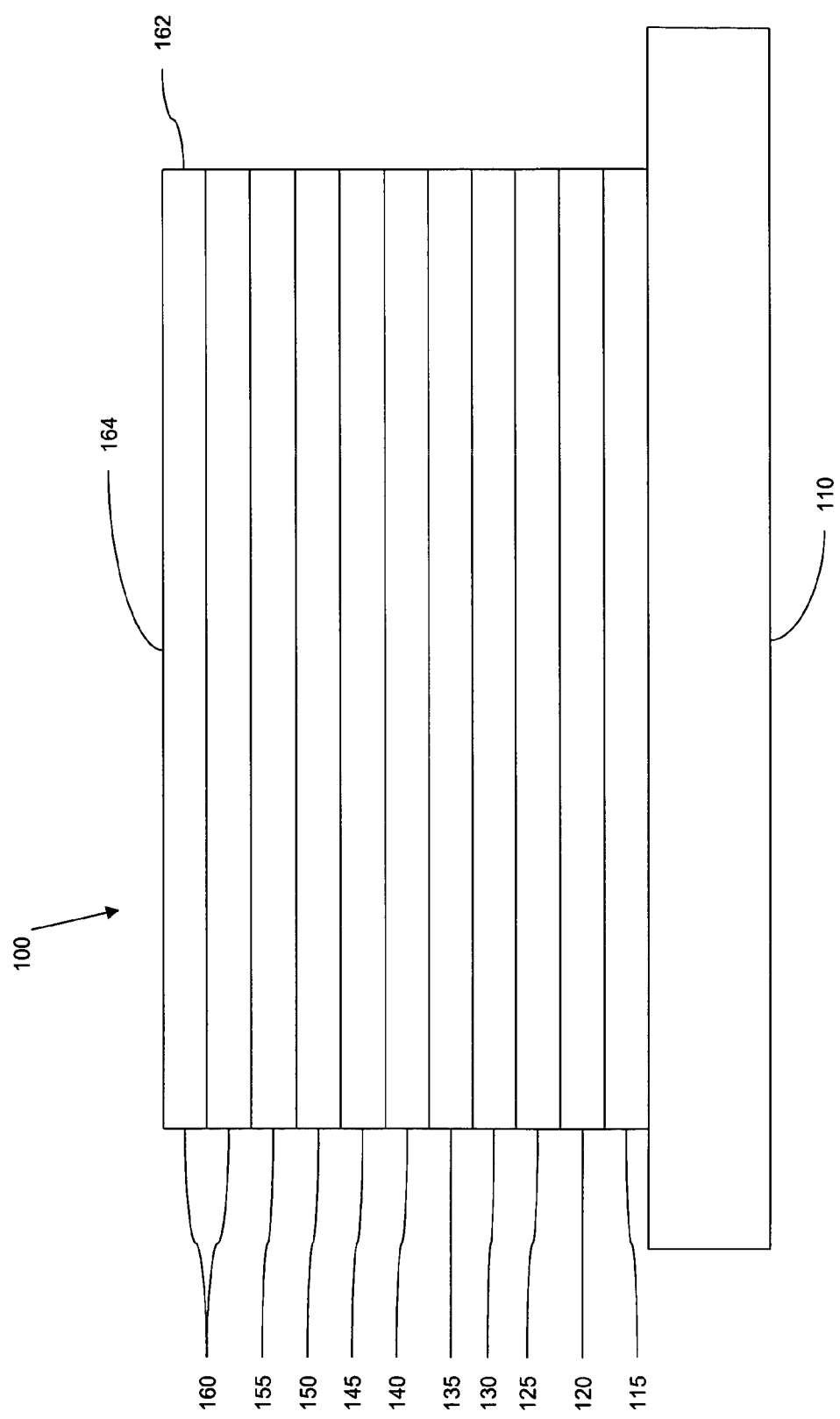
FIG. 1 shows an organic light emitting device having separate electron transport, hole transport, and emissive layers, as well as other layers.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer (ETL) 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. Patent Application Publication No. 2002-0071963 A1 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels directly involved in light emission. A ligand that is photoactive in one molecule may be ancillary in another. These definitions of photoactive and ancillary are intended as non-limiting theories.

Electron transport layer (ETL) 140 may include a material capable of transporting electrons. Electron transport layer 140 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in U.S. Patent Application Publication No. 2002-0071963 A1 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) level of the electron transport layer. The "charge carrying component" is the material responsible for the LUMO that actually transports electrons. This component may be the base material, or it may be a dopant. The LUMO level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and U.S. Patent Application Publication No. 2002-0071963 A1 to Forrest et al., which are incorporated by reference in their entireties.

As used herein, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al. now U.S. Pat. No. 7,071,615, which is incorporated by reference in its entirety.

Figure 2:
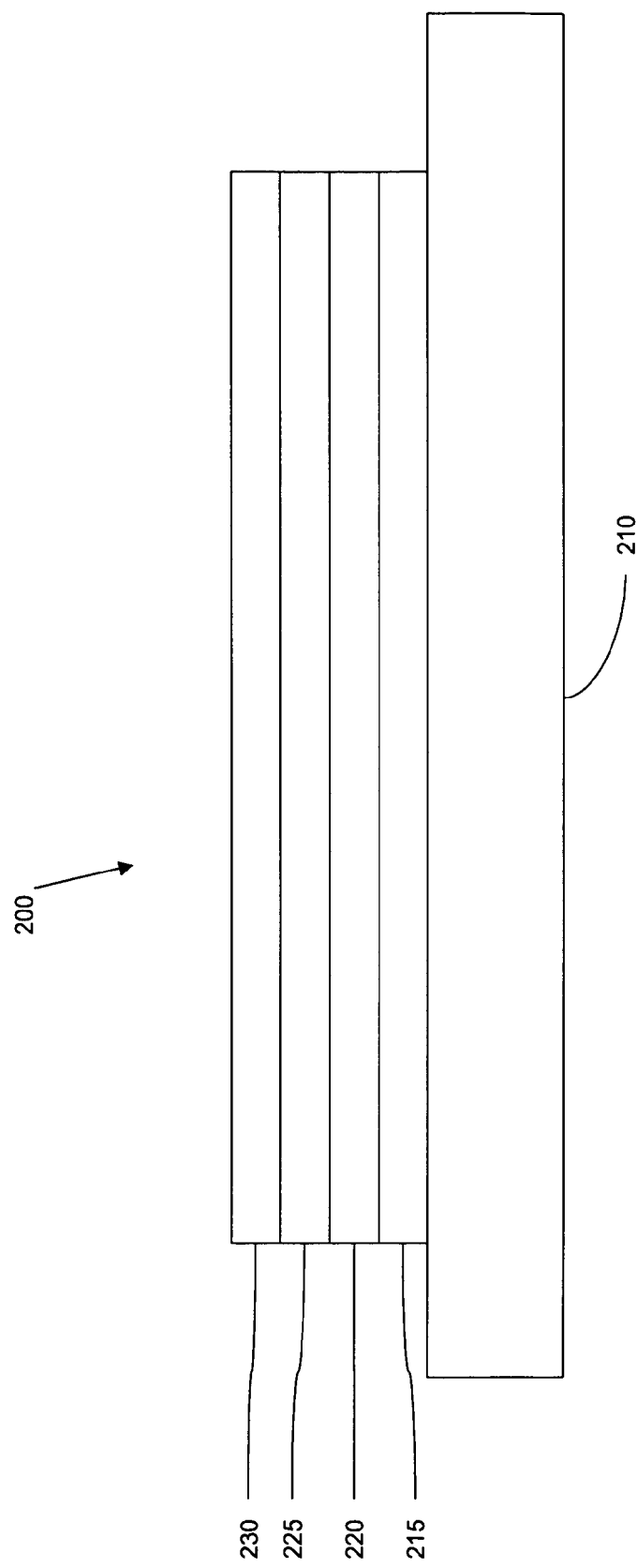
FIG. 2 shows an inverted organic light emitting device that does not have a separate electron transport layer.
Figure 3:
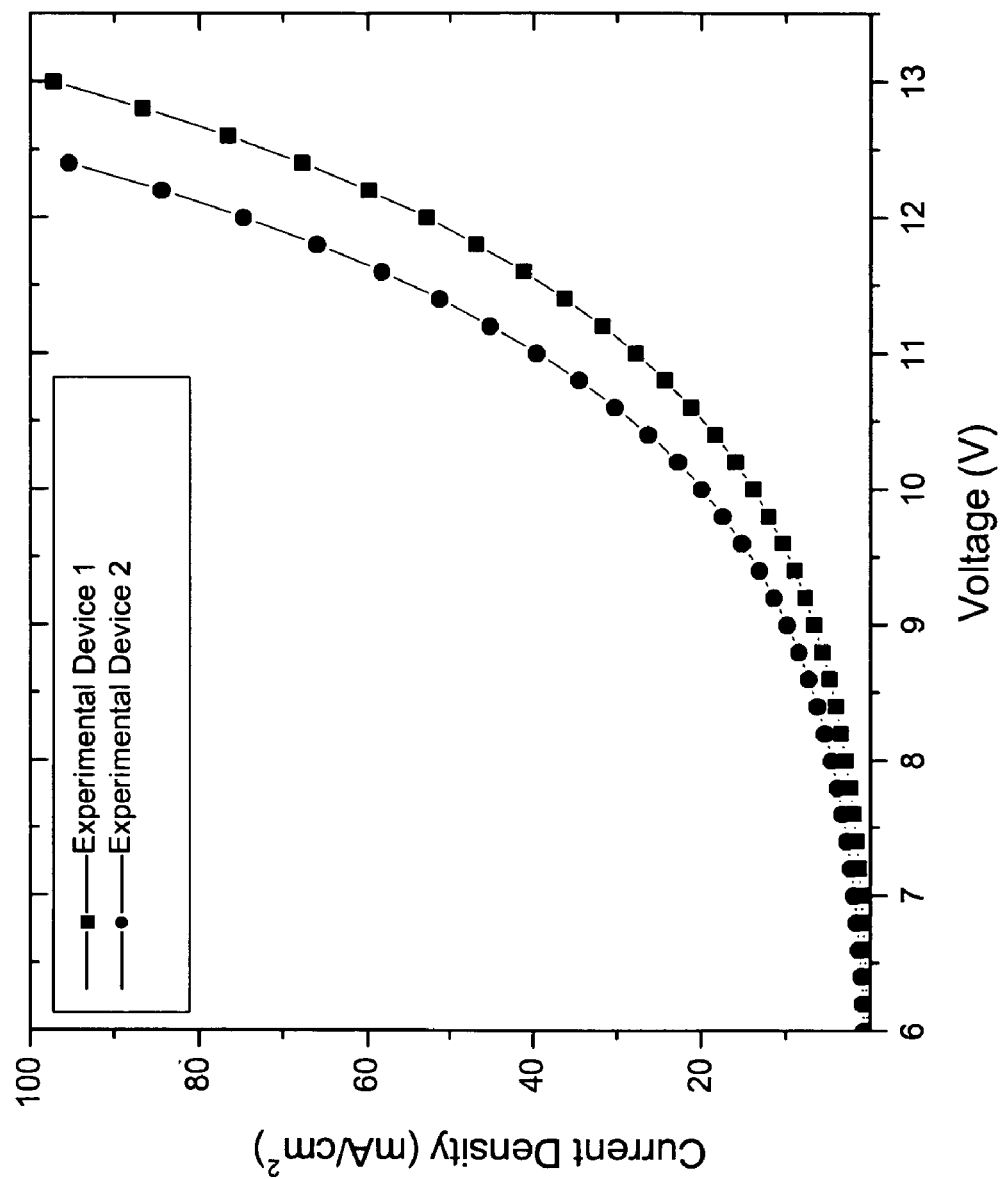
FIG. 3 shows the plots comparing current density (mA/cm$^2$) vs. voltage (V) in devices with either 100 Å of aluminum (III)bis(2-methyl-8-hydroxyquinolinato)4-phenylphenolate (BAlq) as the ETL2 (Experimental Device 1) or 100 Å of HPT as the ETL2 (Experimental Device 2) using Ir(5'-Meppy)$_3$ as the emissive material doped at 6% (all dopant concentrations are in wt % unless otherwise specified).
Figure 4:
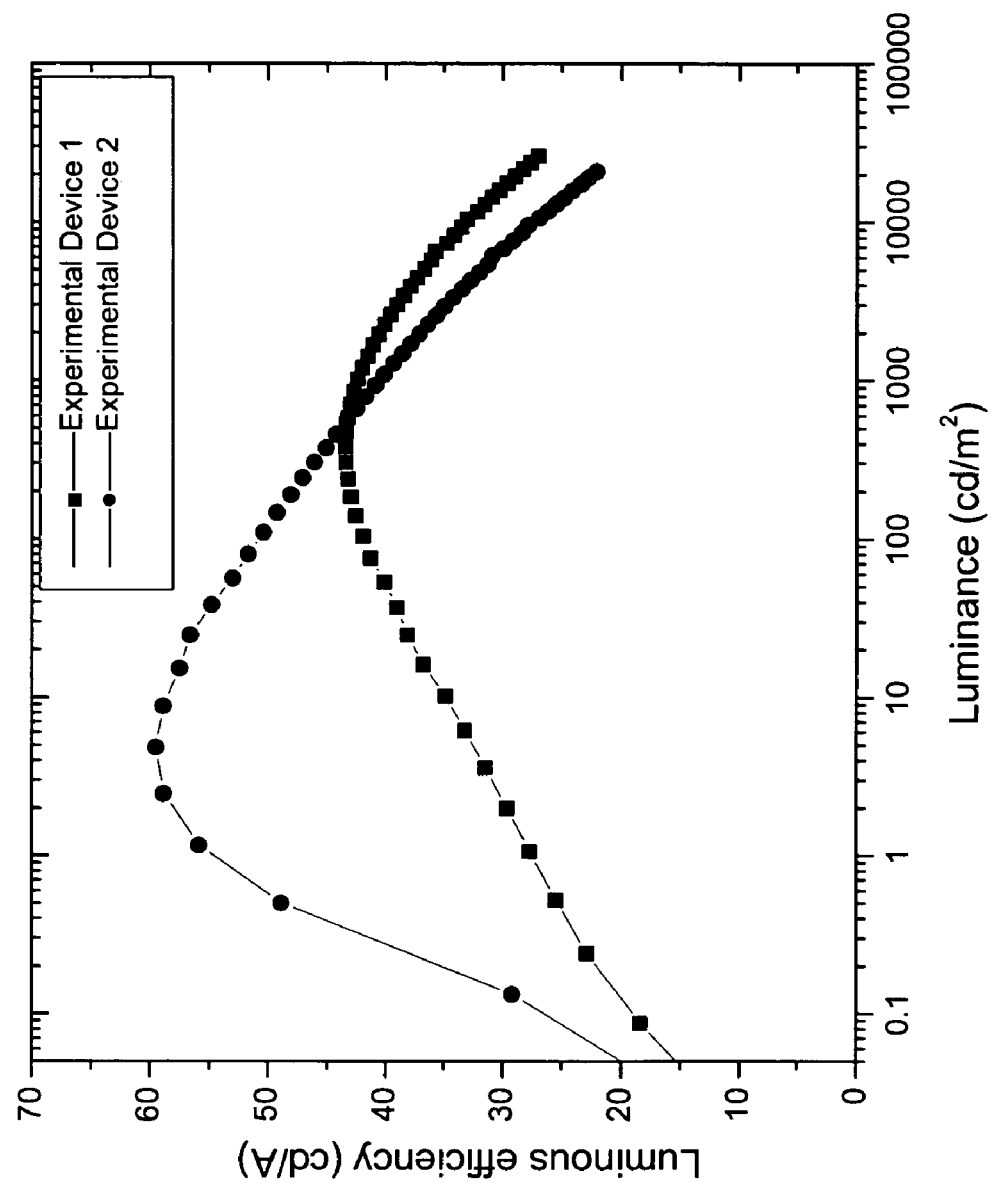
FIG. 4 shows the plots comparing luminous efficiency (cd/A) vs. brightness (cd/m$^2$) comparing devices with either 100 Å of aluminum(III)bis(2-methyl-8-hydroxyquinolinato) 4-phenylphenolate (BAlq) as the ETL2 (Experimental Device 1) or 100 Å of HPT as the ETL2 (Experimental Device 2) using Ir(5'-Meppy)$_3$ as the emissive material doped at 6%.
Figure 5:
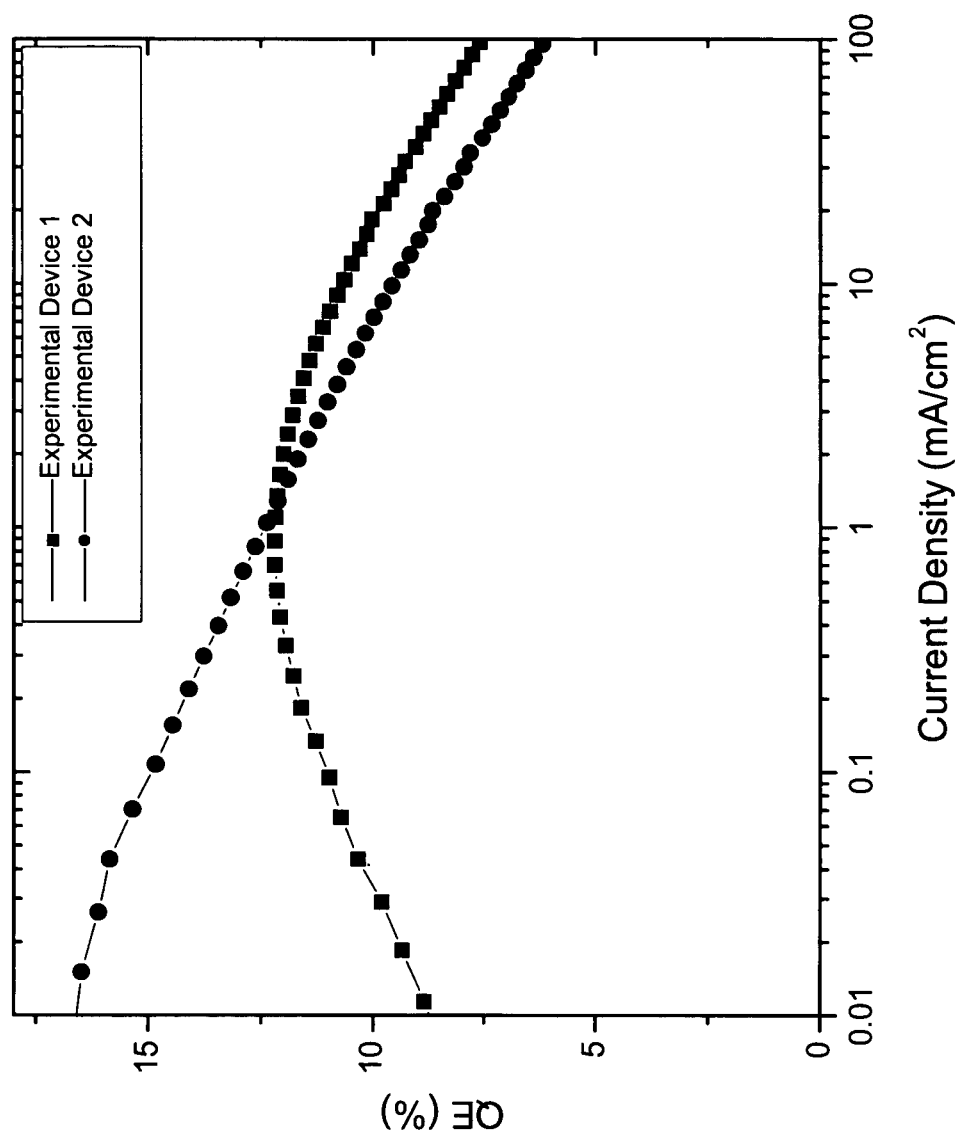
FIG. 5 shows the external quantum efficiency ($\eta_{ext}$) as a function of current density (mA/cm$^2$) comparing devices with either 100 Å of aluminum(III)bis(2-methyl-8-hydroxyquinolinato) 4-phenylphenolate (BAlq) as the ETL2 (Experimental Device 1) or 100 Å of HPT as the ETL2 (Experimental Device 2) using Ir(5'-Meppy)$_3$ as the emissive material doped at 60%.
Figure 6:
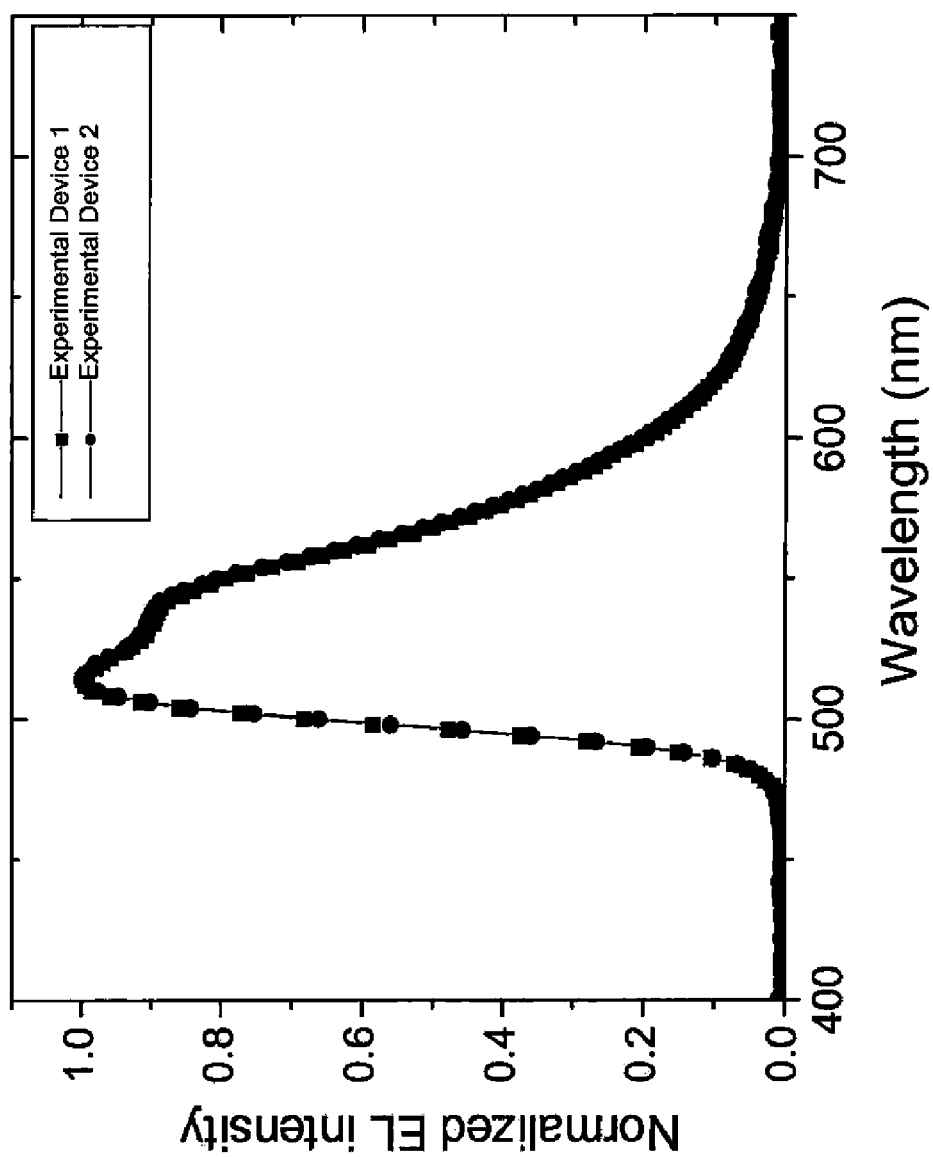
FIG. 6 shows the normalized electroluminescence spectra (normalized EL intensity vs. wavelength) at a current density of 10mA/cm² comparing devices with either 100 Å of aluminum(III)bis(2-methyl-8-hydroxyquinolinato)4-phenylphenolate (BAlq) as the ETL2 (Experimental Device 1) or 100 Å of HPT as the ETL2 (Experimental Device 2) using Ir(5'-Meppy)₃ as the emissive material doped at 6%.
Figure 7:
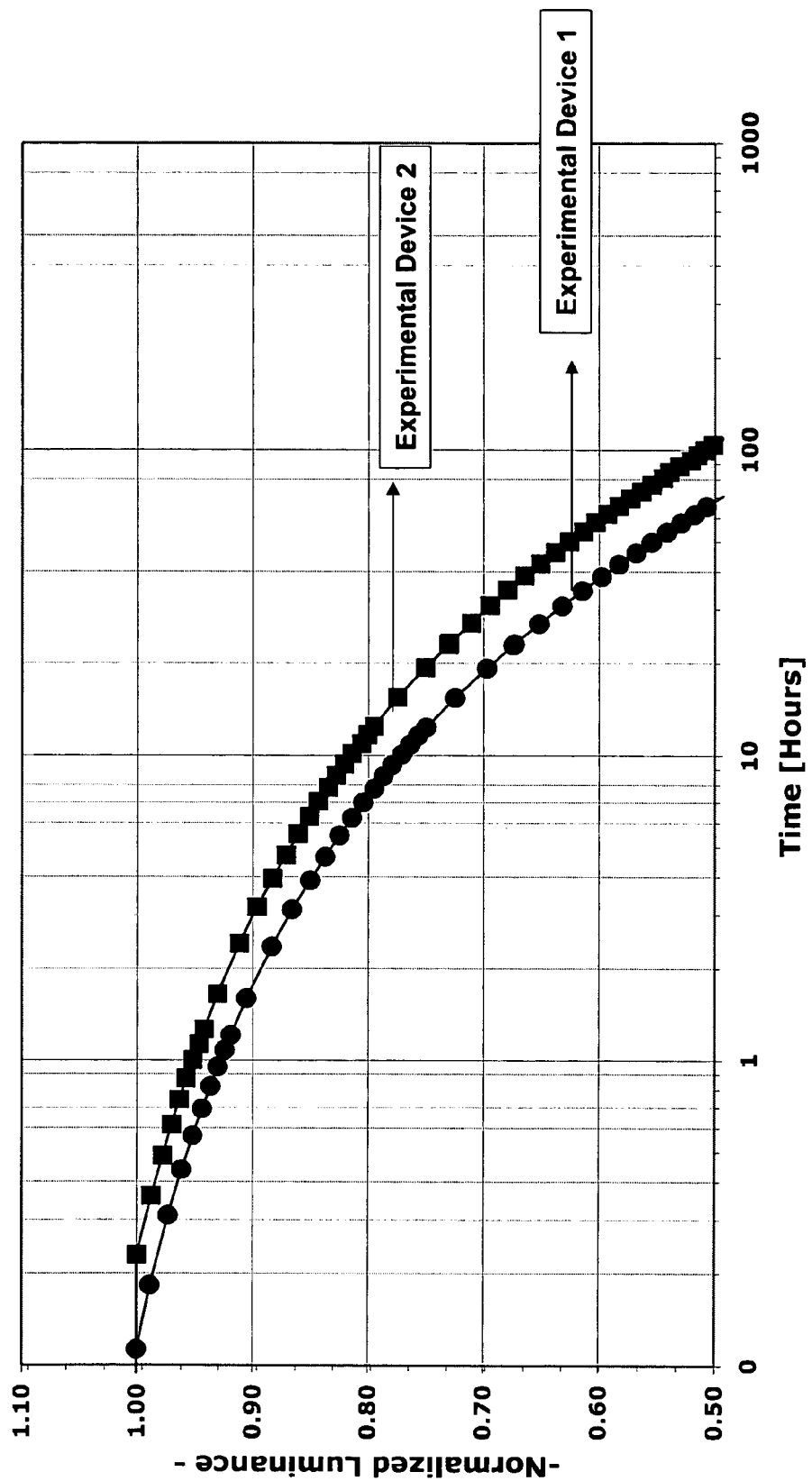
FIG. 7 shows the normalized luminance decay comparing devices with either 100 Å of aluminum(III)bis(2-methyl-8-hydroxyquinolinato)4-phenylphenolate (BAlq) as the ETL2 (Experimental Device 1) or 100 Å of HPT as the ETL2 (Experimental Device 2) using Ir(5'-Meppy)₃ as the emissive material doped at 6% under constant current drive of 40 mA/cm² at room temperature.
Figure 8:
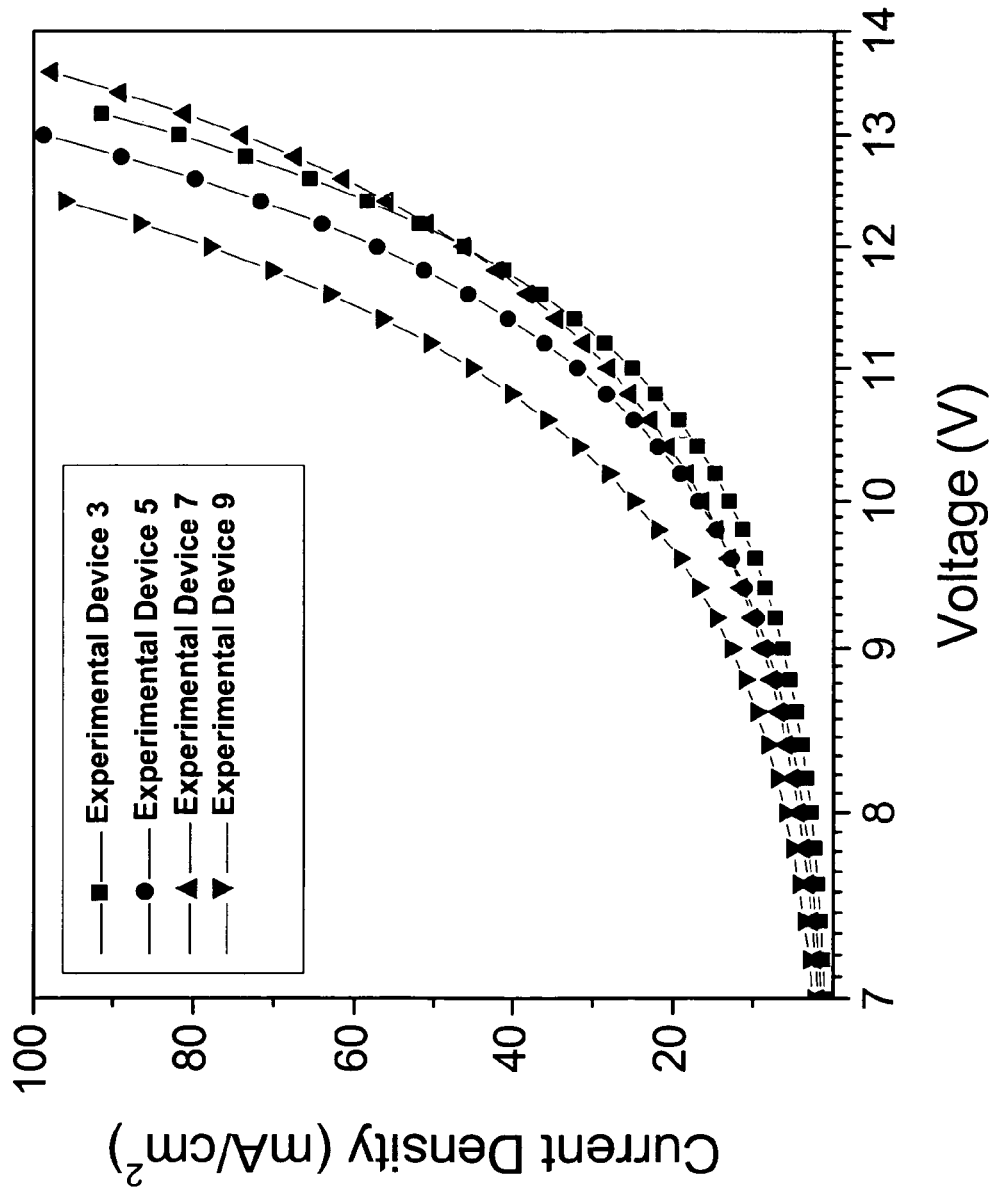
FIG. 8 shows the plots of the current density (mA/cm²) vs. the voltage (V) comparing devices using 100 Å of aluminum(III)bis(2-methyl-8-hydroxyquinolinato)4-phenylphenolate (BAlq) as the ETL2 and using Ir(5'-Me-5-Phppy)₃ as the emissive material doped at 6% (Experimental Device 3), 8% (Experimental Device 5), 10% (Experimental Device 7) and 12% (Experimental Device 9).
Figure 9:
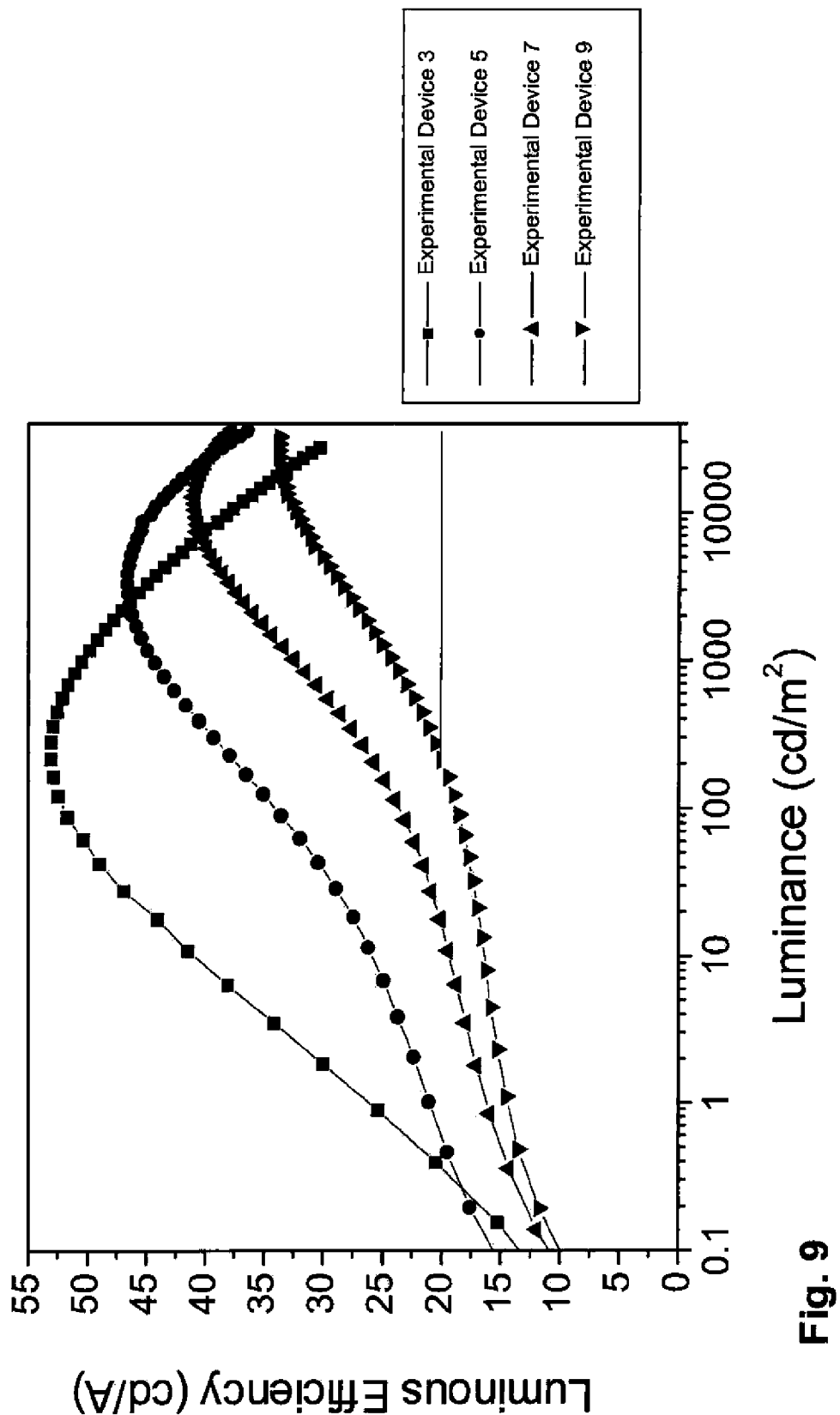
FIG. 9 shows the plots of luminous efficiency (cd/A) vs. brightness (cd/m²) for devices using 100 Å of aluminum(III)bis(2-methyl-8-hydroxyquinolinato)4-phenylphenolate (BAlq) as the ETL2 and using I Ir(5'-Me-5-Phppy)₃ as the emissive material doped at 6% (Experimental Device 3), 8% (Experimental Device 5), 10% (Experimental Device 7) and 12% (Experimental Device 9).
Figure 10:
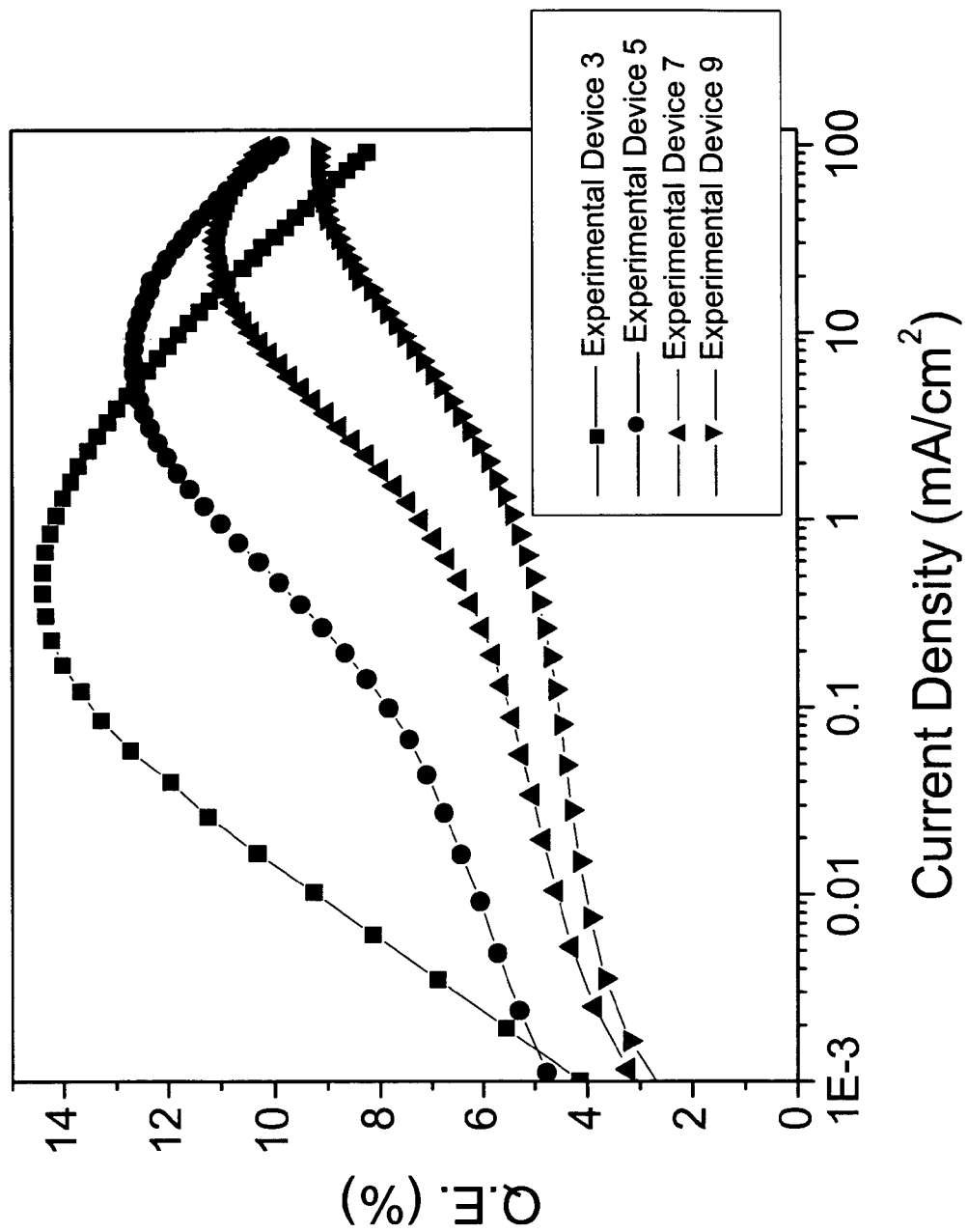
FIG. 10 shows the external quantum efficiency ($\eta_{ext}$) as a function of current density (mA/cm²) for devices using 100 Å of aluminum(III)bis(2-methyl-8-hydroxyquinolinato) 4-phenylphenolate (BAlq) as the ETL2 and using Ir(5'-Me-5-Phppy)₃ as the emissive material doped at 6% (Experimental Device 3), 8% (Experimental Device 5), 10% (Experimental Device 7) and 12% (Experimental Device 9).
Figure 11:
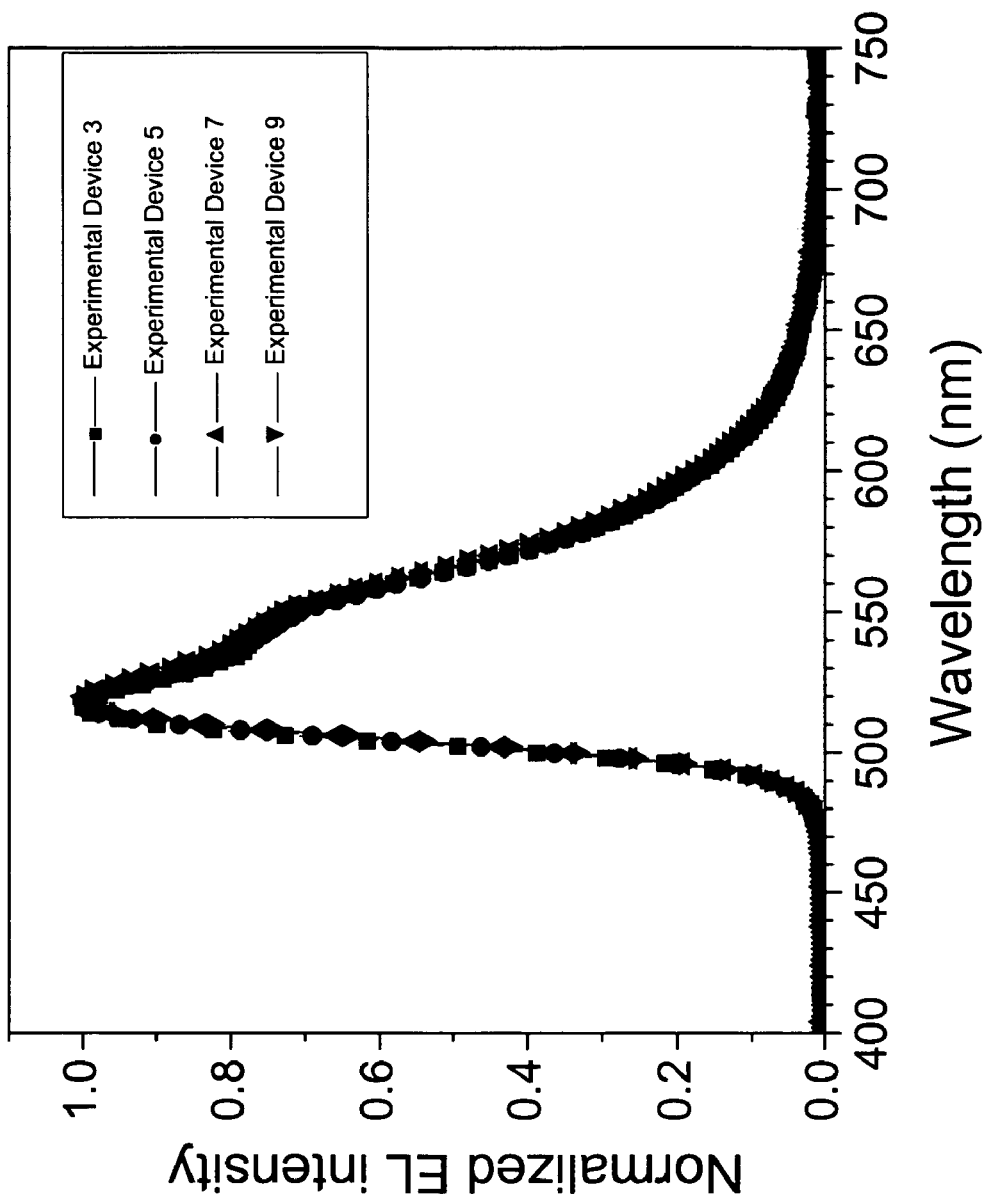
FIG. 11 shows the normalized electroluminescence spectra (normalized EL intensity vs. wavelength) at a current density of 10mA/cm² for devices using 100 Å of aluminum(III)bis(2-methyl-8-hydroxyquinolinato)4-phenylphenolate (BAlq) as the ETL2 and using Ir(5'-Me-5-Phppy)₃ as the emissive material doped at 6% (Experimental Device 3), 8% (Experimental Device 5), 10% (Experimental Device 7) and 12% (Experimental Device 9).
Figure 12:
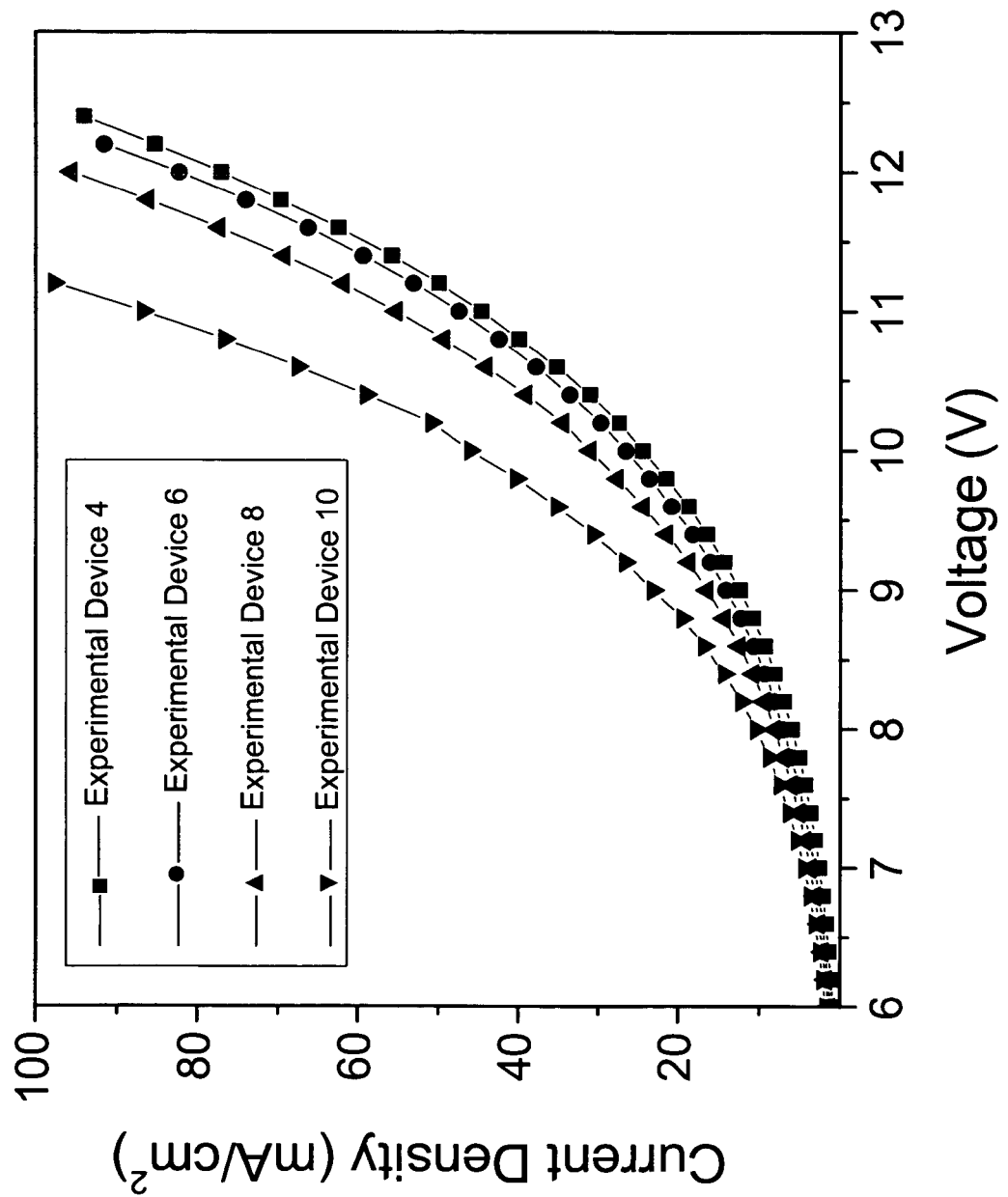
FIG. 12 shows the plots of the current density (mA/cm²) vs. the voltage (V) comparing devices using 50 Å of HPT as the ETL2 and using Ir(5'-Me-5-Phppy)₃ as the emissive material doped at 6% (Experimental Device 4), 8% (Experimental Device 6), 10% (Experimental Device 8) and 12% (Experimental Device 10).
Figure 13:
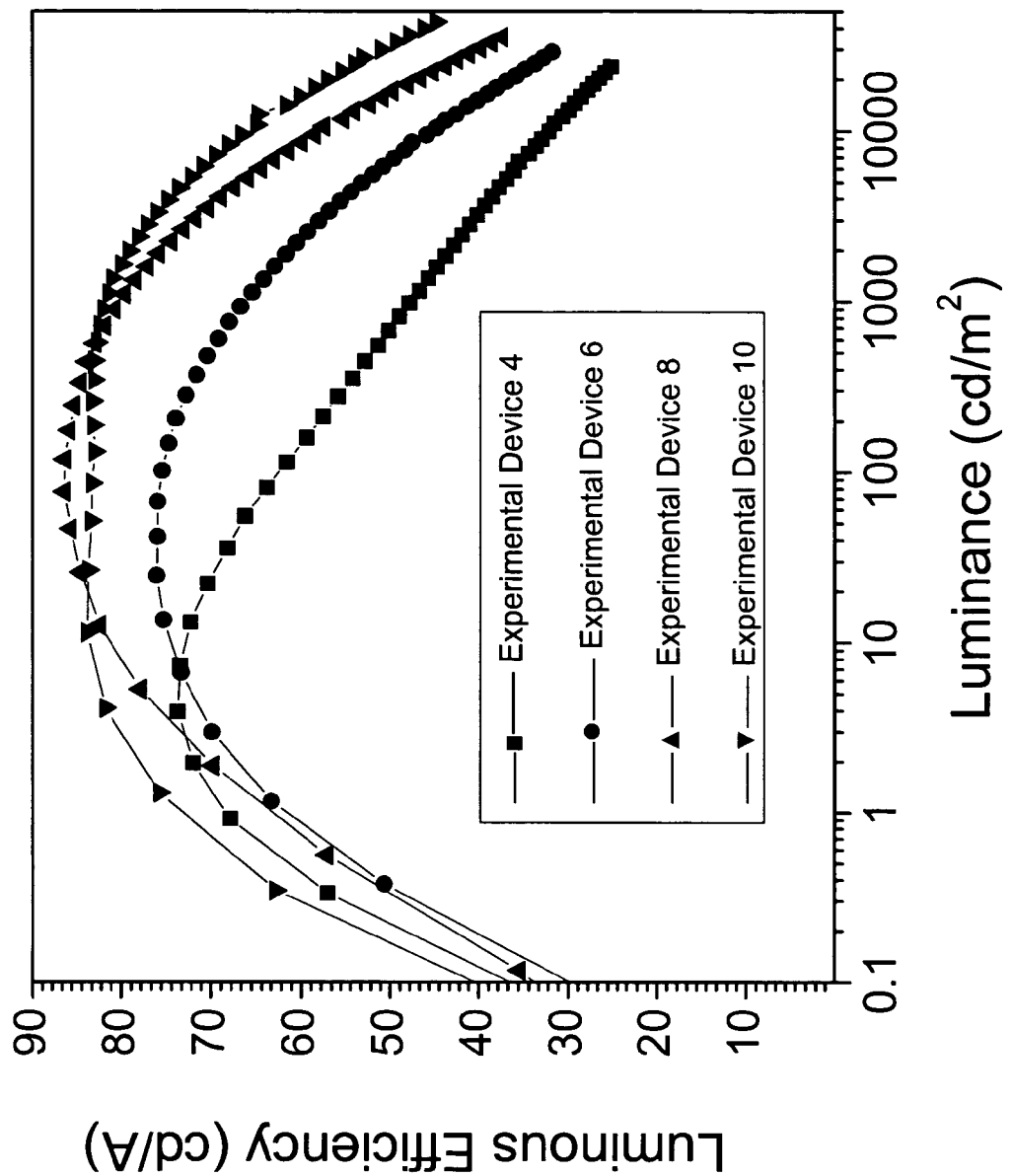
FIG. 13 shows the plots of luminous efficiency (cd/A) vs. brightness (cd/m²) comparing devices using 50 Å of HPT as the ETL2 and using Ir(5'-Me-5-Phppy)₃ as the emissive material doped at 6% (Experimental Device 4), 8% (Experimental Device 6), 10% (Experimental Device 8) and 12% (Experimental Device 10).

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Patent No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together via a linking group to form, for example, a tetradentate or hexadentate ligand having linking group that covalently links a first ligand to a second ligand. Other linkages may be formed. Suitable linking groups and linkages are described, for example, in U.S. patent application Ser. Nos. 10/771,423 (now abandoned, published as US 2005/0170206) and Ser. No. 10/859,796, now U.S. Pat. No. 7,332,232, which are incorporated by reference herein in their entireties. It is believed that this type of linking may increase stability relative to a similar compound without linking In preferred embodiments, the multidentate ligand systems are prepared by the metal catalyzed coupling of the linking group to the ligand. See, for example, Beeston et al., Inorg. Chem. 1998, 37, 4368-4379. In a preferred embodiment, the linking group X provides no π-conjugation between the linked ligands. Having π-conjugation between the linked ligands may change the electronic properties of the ligands and the resulting metal complexes, such as a red-shift in the luminescence. It is desirable to link the ligands together to without significantly altering the electronic properties of the ligands and the resulting metal complex. A non-conjugated linking group may comprise at least one atom in the linkage which contains no π-electrons, such as an $sp^3$ hybridized carbon or silicon. In a preferred embodiment of the invention, the linking group, X, is selected from the group consisting of —$(CR_2)_d$—, —$[O(CR_2)_e]O$—, or a group having the formula

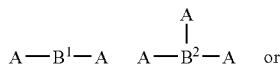

a. wherein
   A is —$(CR_2)_f$—, or -Z-$(CR_2)_g$—;
   Z is —O—, —NR—, or —$SiR_2$—;
   $B^1$ is —O—, —NR—, —CR=CR—, aryl, heteroaryl, cycloalkyl, or a heterocyclic group,

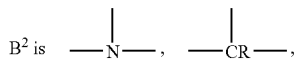

alkyl, aryl, heteroaryl, cycloalkyl, or a heterocyclic group;
   a. each R is independently selected from H, alkyl, aralkyl, aryl and heteroaryl,
      i. d is 1 to 6,
      ii. e is 1 to 6,
      iii. f is 1 to 4, and
      iv. g is 1 to 4.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, C(O)R, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, C(O)R, $NR_2$, cyclic-amino, $NO_2$, and OR.

The terms "alkylaryl" as used herein contemplates an alkyl group that has as a substituent an aromatic group. Additionally, the alkylaryl group may be optionally substituted on the aryl with one or more substituents selected from halo, CN, $CO_2R$, C(O)R, $NR_2$, cyclic-amino, $NO_2$, and OR. The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

All value ranges, are inclusive over the entire range. Thus, for example, a range between 0-4 would include the values 0, 1, 2, 3 and 4.

Phosphorescent OLEDs with unexpected and exceptionally high device efficiency are disclosed herein. In some embodiments, the phosphorescent dopants used are Ir(5'-alkyl-2-phenylpyridine) type metal complexes. Many alkyl substituted on Ir(2-phenylpyridine) complexes are known. However, we have found that 5'-alkyl substituted analogs have unexpected properties such that, when they are incorporated into an organic light emitting device, unexpected results are attained. In some embodiments, the phosphorescent dopants used are Ir(5'-alkyl substituted phenyl-isoquinoline) type metal complexes. By incorporating the phosphorescent materials of the present invention into organic light emitting devices (OLEDs), unexpected and exceptionally high device efficiencies have been demonstrated.

In one embodiment of the present invention, a phosphorescent emissive material having improved efficiency when incorporated into an organic light emitting device is provided, the emissive material having the formula I

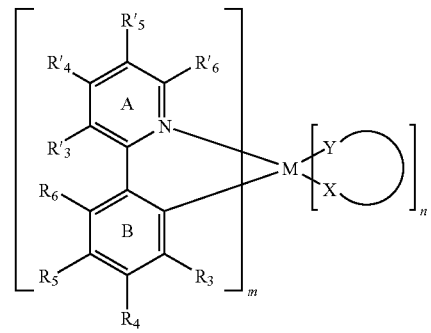

Formula I

M is a metal selected from Ir, Pt, Rh or Pd;

ring A is an aromatic heterocyclic or a fused aromatic heterocyclic ring having an alkyl substituent at the $R_{15}$ position and having at least one nitrogen atom, N, that is coordinated to the metal M, wherein the ring A can be optionally substituted with one or more substituents at the $R'_3$, $R'_4$ and $R'_6$ positions; and additionally or alternatively the $R'_3$ and $R'_4$ substituted positions on ring A together form, independently a fused ring, wherein the fused ring may be optionally substituted;

ring B is an aromatic ring with at least one carbon atom coordinated to metal M, wherein ring B can be optionally substituted with one or more substituents at the $R_3$, $R_4$ $R_5$ and $R_6$ positions;

$R'_3$ $R'_4$ and $R'_6$ are each independently H, alkyl, alkenyl, alkynyl, heteroalkyl, alkenyl, alkynyl, heteroalkyl, aryl, heteroaryl, aralkyl; and wherein $R'_3$, $R'_4$ and $R'_6$ are optionally substituted by one or more substituents Z; and $R_3 R_4 R_5$ $R_6$ are each independently selected from the group consisting of H, alkyl, alkenyl, alkynyl, alkylaryl, CN, $CO_2R$, C(O)R, $NR_2$, $NO_2$, OR, halo, aryl, heteroaryl, substituted aryl, substituted heteroaryl or a heterocyclic group such that when $R'_3$, $R'_4$, and $R'_6$ are all H, $R_3$, $R_4$, $R_5$ and $R_6$ are also all H or at least one of $R_4$, $R_5$ and $R_6$ is a linking group covalently linking two or more of the maximum number of ligands that may be attached to the metal, an unsubstituted phenyl ring, a fluoro-substituted phenyl ring or a phenyl ring substituted with a substituent that renders the phenyl ring equally or less coplanar than the unsubstituted phenyl ring with respect to Ring B;

alternatively, $R'_3$ and $R_6$ may be bridged by a group selected from —$CR_2$—$CR_2$—, —CR=CR—, —$CR_2$—, —O—, —NR—, —O—$CR_2$—, —NR—$CR_2$—, and —N=CR—;

each R is independently H, alkyl, alkenyl, alkynyl, heteroalkyl, aryl, heteroaryl, or aralkyl; wherein R is optionally substituted by one or more substituents Z; each Z is independently a halogen, R', O R', N(R')$_2$, S R', C(O)R', C(O)O R', C(O)N(R')$_2$, CN, SO$_2$, SO R', SO$_2$ R', or SO$_3$ R';

Each R' is independently H, alkyl, alkenyl, alkynyl, heteroalkyl, aryl, or heteroaryl;

(X-Y) is an ancillary ligand;

m is a value from 1 to the maximum number of ligands that may be attached to the metal; and m+n is the maximum number of ligands that may be attached to the metal.

This embodiment includes a photoactive ligand having the following ligand structure:

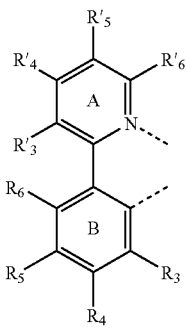

This ligand is referred to as "photoactive" because it is believed that it contributes to the photoactive properties of the emissive material. The emissive material comprises at least one photoactive ligand and a heavy metal ion such that the resulting material has (i) a carbon-metal bond between ring B and the metal and (ii) the nitrogen of ring A is coordinated to the metal. Thus the emissive materials of Formula I comprise a partial structure having the following formula

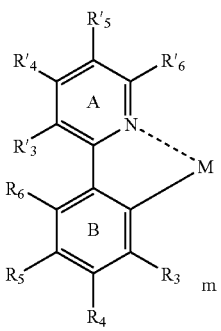

M may be Ir, Pt, Rh or Pd. Preferably, the metal is Ir or Pt. Most preferably, the metal is Ir.

Thus in the emissive material of Formula 1:

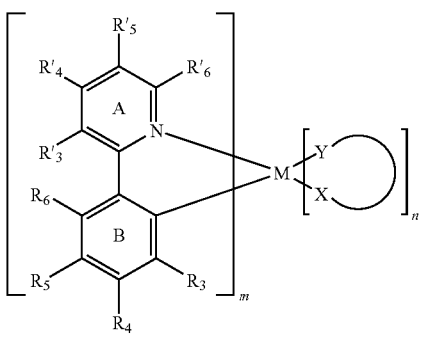

I m, the number of photoactive ligands of a particular type, may be any integer from 1 to the maximum number of ligands that may be attached to the metal. For example, for Ir, m may be 1, 2 or 3. n, the number of "ancillary" ligands of a particular type, may be any integer from zero to one less than the maximum number of ligands that may be attached to the metal. (X-Y) represents an ancillary ligand. These ligands are referred to as "ancillary" because it is believed that they may modify the photoactive properties of the molecule, as opposed to directly contributing to the photoactive properties. The definitions of photoactive and ancillary are intended as non-limiting theories. For example, for Ir, n may be 0, 1 or 2 for bidentate ligands. Ancillary ligands for use in the emissive material may be selected from those known in the art. Non-limiting examples of ancillary ligands may be found in PCT Application Publication WO 02/15645 A1 to Lamansky et al. at pages 89-90, which is incorporated herein by reference. Preferred ancillary ligands include acetylacetonate (acac) and picolinate (pic), and derivatives thereof. The preferred ancillary ligands have the following structures:

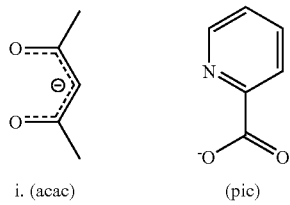

i. (acac)          (pic)

The emissive materials of Formula I include an emissive material having a formula where n is zero and m is the maximum number of ligands that may be attached to the metal as depicted in the following structure:

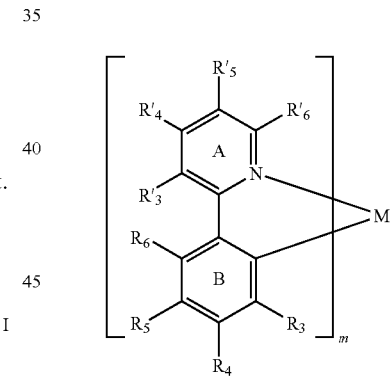

For example, for Ir, m is three in this preferred embodiment, and the structure may be referred to as a "tris" structure. The tris structure is preferred because it is believed to be particularly stable. $R_3$, $R_4$, $R_5$, $R_6$, $R'_3$, $R'_4$, $R'_5$ and $R'_6$ are defined according to the definitions of Formula I.

In one embodiment, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal.

In another embodiment of the present invention, M is Ir and m is 3, giving an emissive material of the formula:

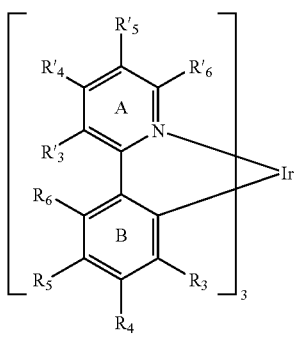

Where $R_3$, $R_4$, $R_5$, $R_6$, $R'_3$, $R'_4$, $R'_5$ and $R'_6$ are defined according to the definitions of Formula I. In some preferred embodiments, particularly in embodiments where green emission is desired, ring A is pyridyl. In other preferred embodiments, particularly in embodiments where red emission is desired, substituents at $R'_3$ and $R'_4$ form a fused ring. An example of a red emitting embodiment of the present invention includes an emissive material of Formula I having the following structure:

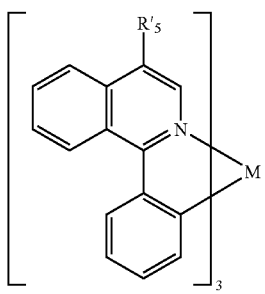

comprising a ligand having the structure:

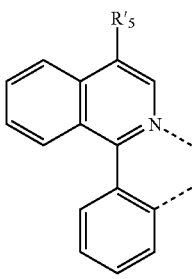

and a partial structure for the emissive material as follows:

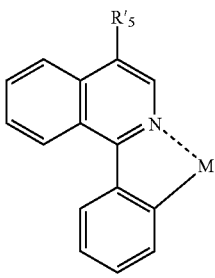

M may be Ir, Pt, Rh or Pd. Preferably, the metal is Ir or Pt. Most preferably, the metal is Ir. This embodiment includes an emissive material wherein M is iridium and $R_{15}$ is methyl having the structural formula:

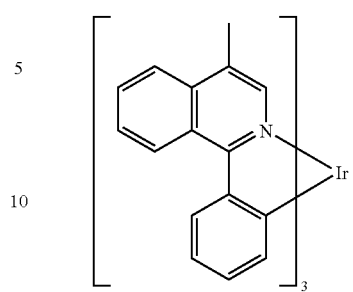

Another preferred embodiment where M is iridium and $R'_5$ is methyl includes an emissive material having the structural formula:

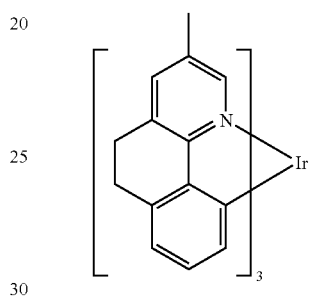

In one embodiment of the present invention according to Formula I, at least one of $R_3$, $R_4$, $R_5$, $R_6$, $R'_3$, $R'_4$, and $R'_6$ is a phenyl substituent. This embodiment includes an emissive material of Formula I where n is zero, and m is the maximum number of ligands that may be attached to the metal as depicted in the following structures:

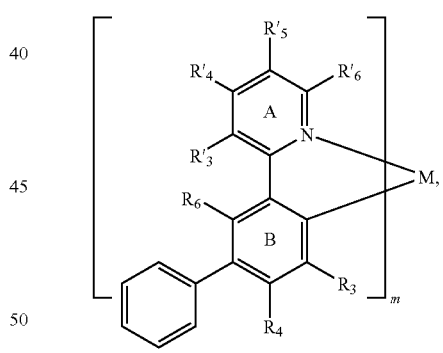

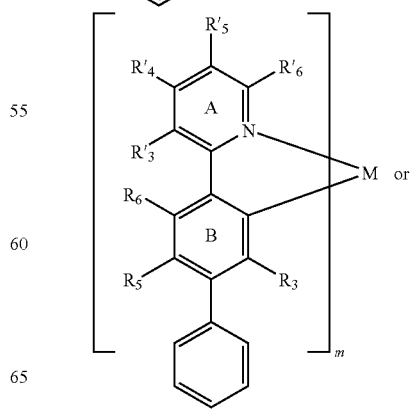

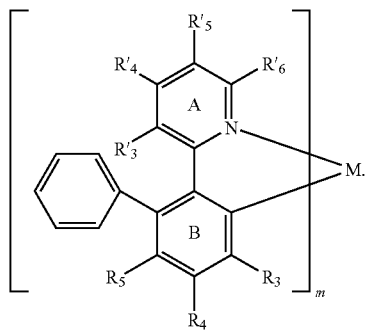

For example, for Ir, m is three in this preferred embodiment, and the structure may be referred to as a "tris" structure. The tris structure is preferred because it is believed to be particularly stable. $R_3$, $R_4$, $R_5$, $R_6$, $R'_3$, $R'_4$, $R'_5$, and $R'_6$ are defined according to the definitions of Formula I.

In one embodiment, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal.

In one embodiment of the emissive materials of Formula I, ring A is a non-fused pyridyl ring, at least one of $R_3$, $R_4$, $R_5$, $R_6$, $R'_3$, $R'_4$, and $R'_6$ comprises a phenyl moiety. In preferred embodiments at least one of $R_4$, $R_5$, $R_6$ is an unsubstituted phenyl ring, a fluoro-substituted phenyl ring or a phenyl ring substituted with a substituent that renders the phenyl ring equally or less coplanar than the unsubstituted phenyl ring with respect to Ring B. In particular embodiments, the substituent that renders the phenyl ring equally or less coplanar than the unsubstituted phenyl ring with respect to Ring B is an alkyl substituent. This embodiment includes an emissive material having the formula

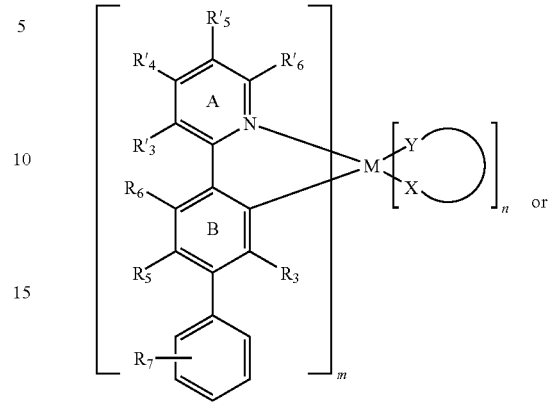

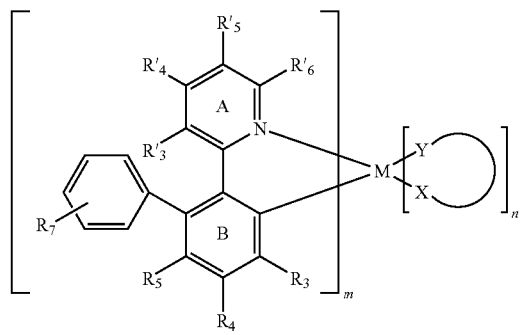

Where $R_7$ is H, F or a substituent that renders the phenyl subsituent at Ring B equally coplanar with or less coplanar than the unsubstituted phenyl ring with respect to Ring B. Preferably $R_7$ is selected from the group consisting of H, F and alkyl.

These emissive materials include a ligand structure of the formula

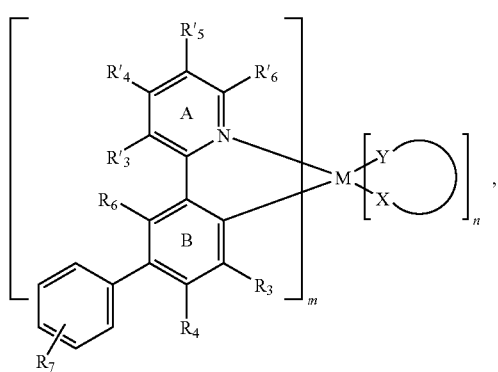

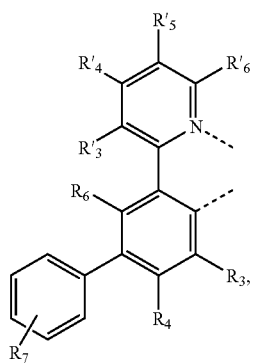

-continued

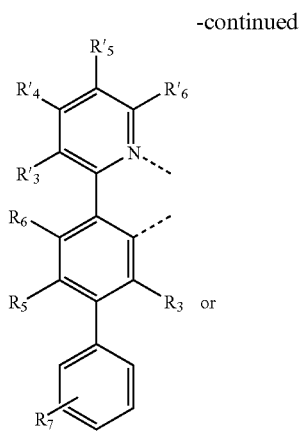

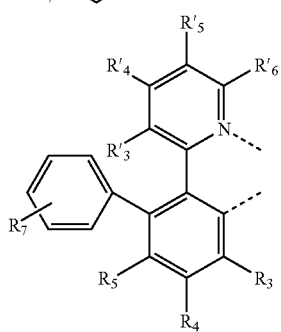

In one embodiment R'$_5$ is methyl and m is 3, giving an emissive material of the formula:

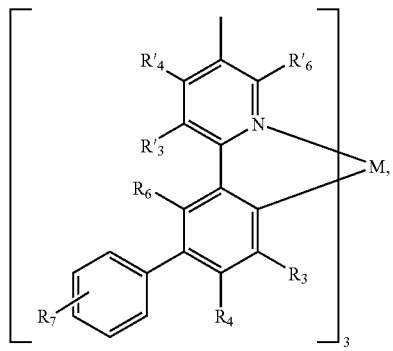

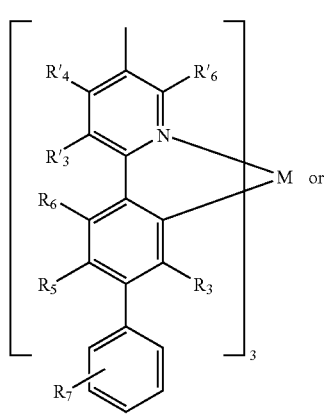

-continued

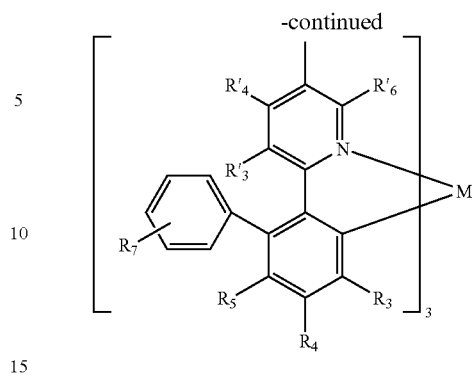

In a particularly preferred embodiment, R$_5$ is unsubstituted phenyl, giving an emissive material of the formula

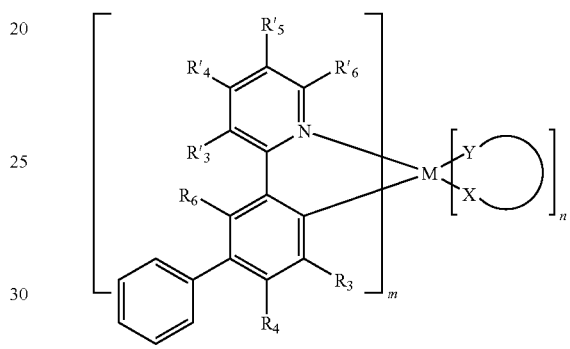

with a ligand structure having the formula:

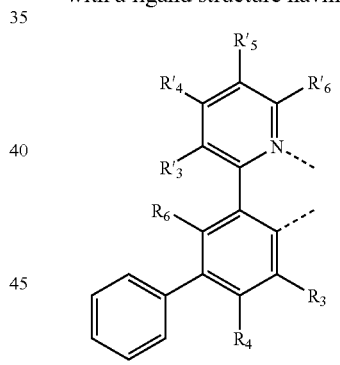

and a partial structure for the emissive material of the formula:

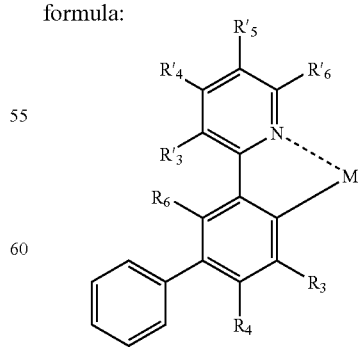

Where R$_3$, R$_4$, R$_6$, R'$_3$ R'$_4$, R'$_5$, and R'$_6$ are defined according to the definitions of Formula I.

In another embodiment R₅ is unsubstituted phenyl, M is Ir and m is 3, giving an emissive material of the formula:

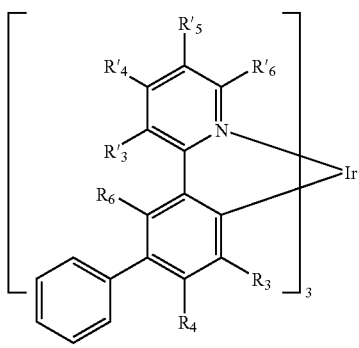

Where R₃, R₄, R₆, R'₃ R'₄, R'₅, and R₁₆ are defined according to the definitions of Formula I. Preferably R'₅ is methyl, R₅ is unsubstituted phenyl and R₃=R₄=R₆=R'₃=R'₄=R'₆=H. The emissive material of this embodiment has the following structure:

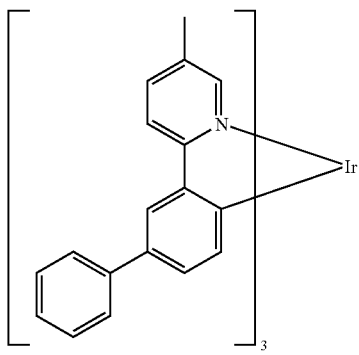

In another embodiment, R'₅ is methyl, m is 3, M is Ir and R₅ is alkyl-substituted phenyl, preferably methyl-substituted phenyl giving an emissive material of the formula:

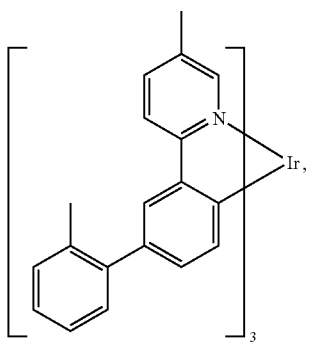

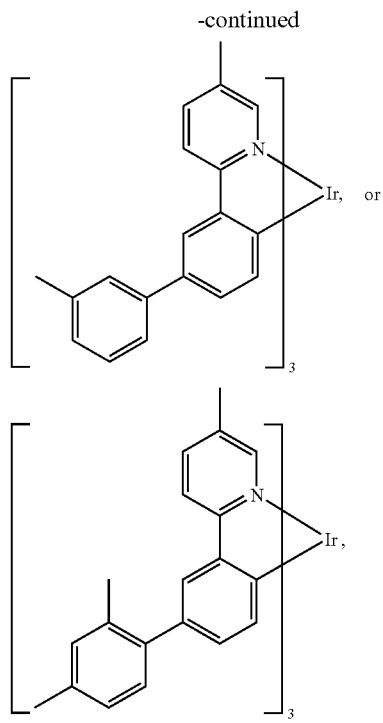

In another embodiment R'₅ is methyl, m is 3, M is Ir and R₅ is fluoro-substituted phenyl giving an emissive material of the formula:

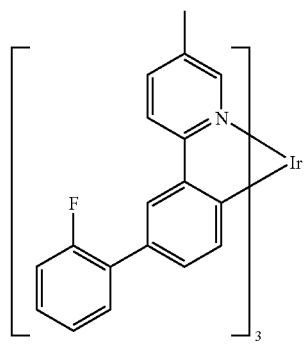

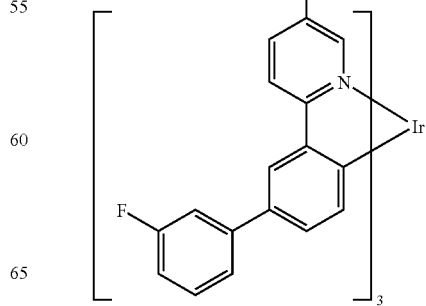

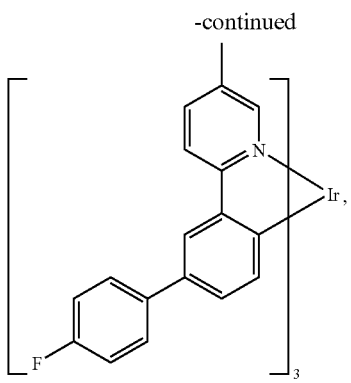

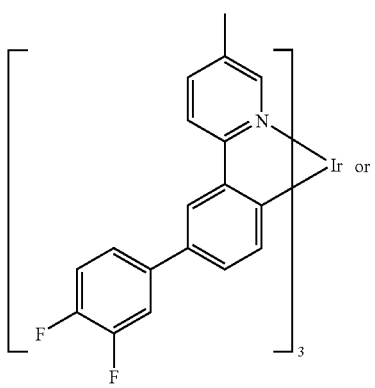

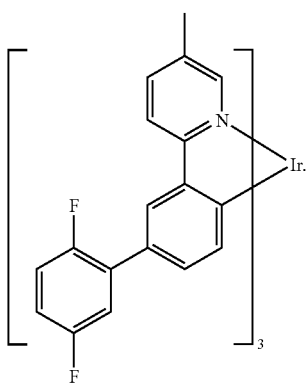

In another embodiment of the emissive materials of Formula I, $R_3=R_4=R_5=R_6=R'_3=R'_4=R'_6=H$ to give an emissive material of the formula

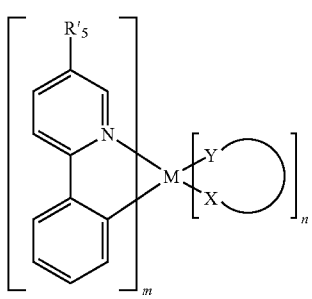

having a ligand structure of the formula:

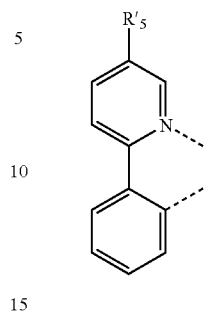

and a partial structure for the emissive material of the formula:

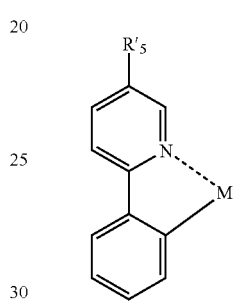

In a preferred embodiment, n is zero, and m is the maximum number of ligands that may be attached to the metal.

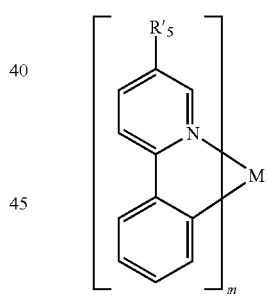

For example, for Ir, m is three in this preferred embodiment, and the structure may be referred to as a "tris" structure. The tris structure is preferred because it is believed to be particularly stable. $R'_5$, is alkyl as defined in Formula I.

In one embodiment, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal. Preferably, if there are different photoactive ligands attached to the metal, each photoactive ligand has the structure indicated in Formula I.

In preferred embodiment, M is Ir and m is 3, giving an emissive material of the formula:

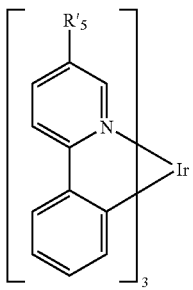

Wherein $R_5$, is alkyl as defined in Formula I. In a particularly preferred embodiment, $R'_5$ is methyl. The emissive material of this embodiment has the following structure:

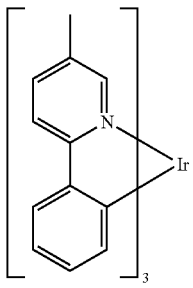

and comprises a ligand having the following structure

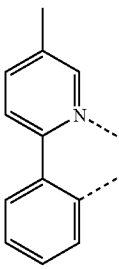

and a partial structure of for the emissive material as follows:

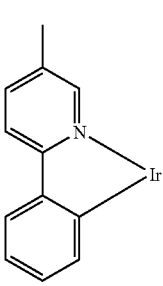

In another embodiment of Formula I, at least one of $R'_3$, $R'_4$ and $R'_6$ is alkyl in addition to $R'_5$ being alkyl. In such an embodiment, the remaining positions can be optionally substituted according to the definitions of Formula I. This embodiment includes emissive materials in which at least one of $R'_3$, $R'_4$ and $R'_6$ is methyl as depicted in the following structural formulas

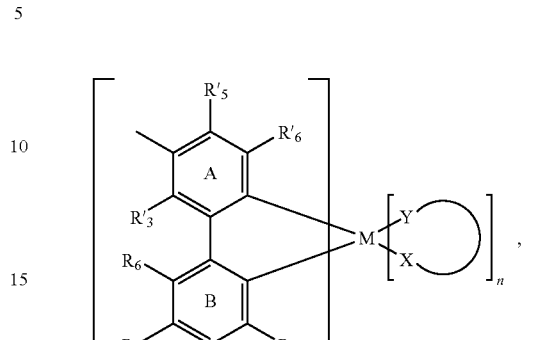

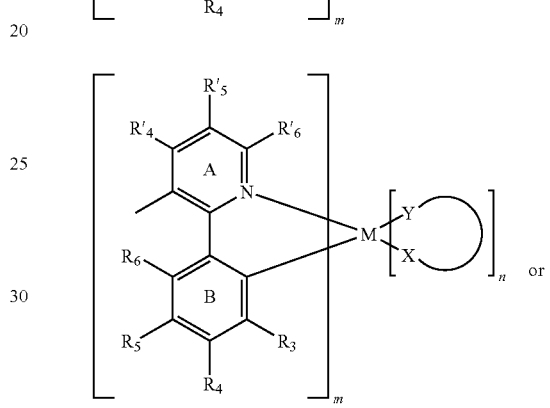

having corresponding ligand structures as depicted respectively below:

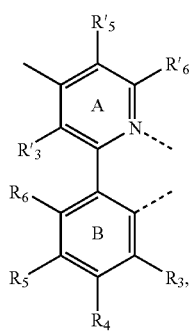 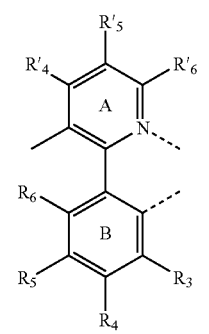

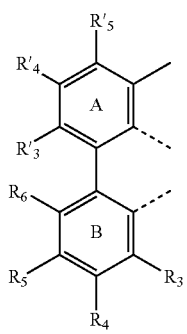

and having partial structures for the emissive material comprising ligand structures of depicted respectively below:

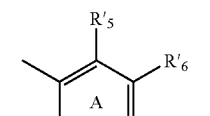 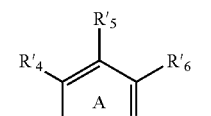

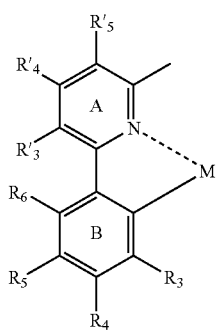

In preferred embodiments, n is zero, and m is the maximum number of ligands that may be attached to the metal as depicted in the structures below:

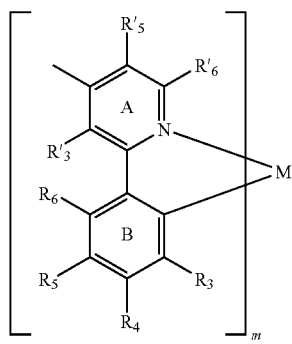

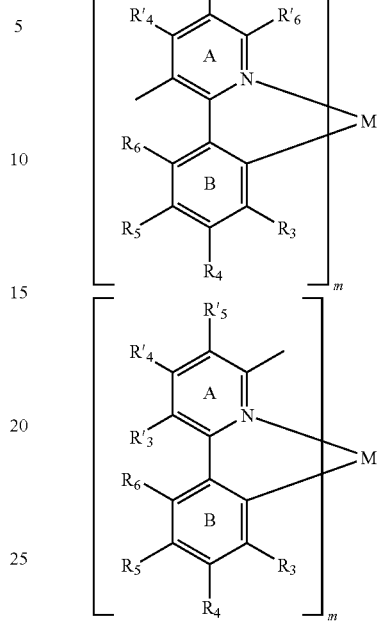

This embodiment of the invention includes, for example, molecules with the following structures where M is Ir and m is 3, and $R'_5$ is methyl:

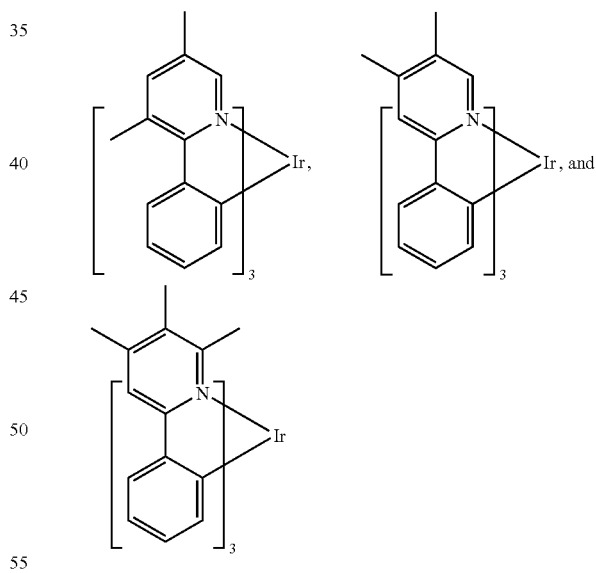

Another embodiment of the invention comprises an emissive material having a formula in which at least one of $R'_3$, $R'_4$, and $R'_6$ is alkyl and at least one of $R_3$, $R_4$, $R_5$ and R is aryl, preferably phenyl or substituted phenyl. This includes an embodiment in which $R_5$ is a phenyl substituent and at least one of $R'_3$, $R'_4$, and $R'_6$ is a methyl substituent. In one embodiment $R_5$ is phenyl and $R'_4$ is methyl. In another embodiment $R_5$ is phenyl and $R'_3$ is methyl. In another embodiment $R_5$ is phenyl and $R'_6$ is methyl. These embodiments respectively, give an emissive material comprising a molecule with one of the following formulas:

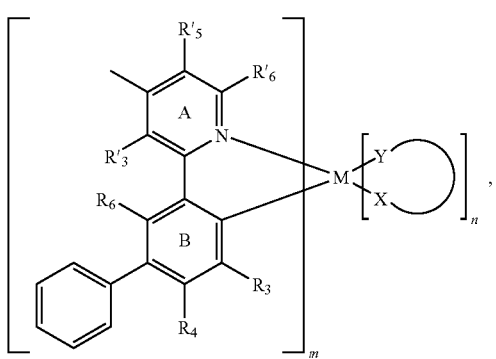

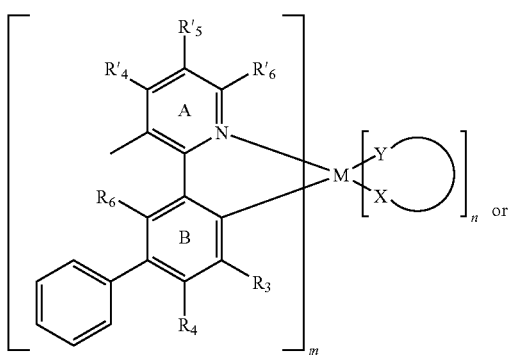

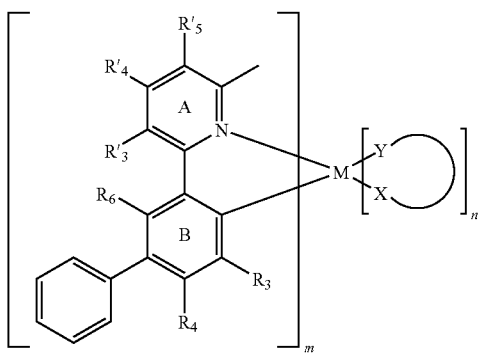

each having a corresponding ligand structure as depicted, respectively, below:

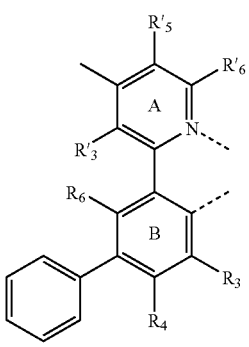 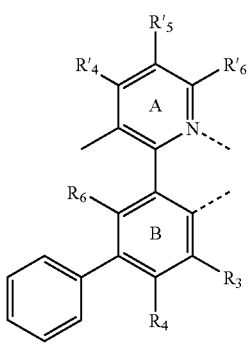

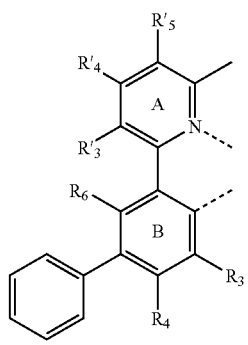

and partial structures for the emissive material as depicted, respectively, below:

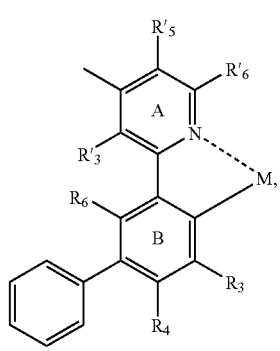

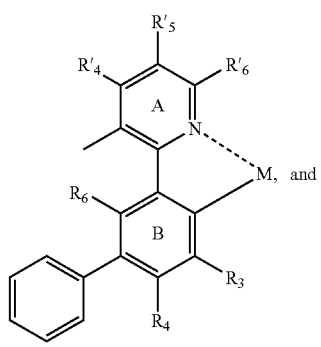

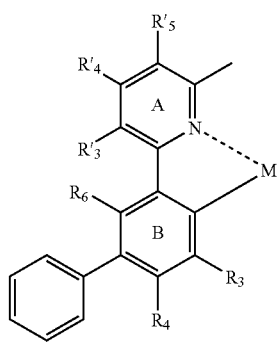

In other preferred embodiments, n is zero, and m is the maximum number of ligands that may be attached to the metal. These embodiments include and emissive material comprising a molecule with the structure:

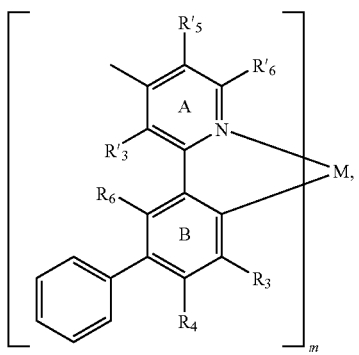
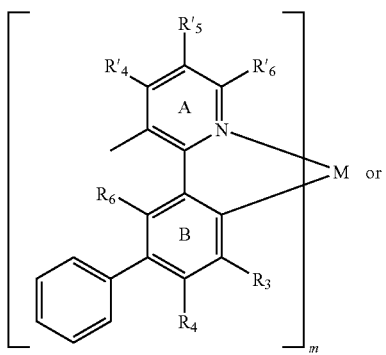
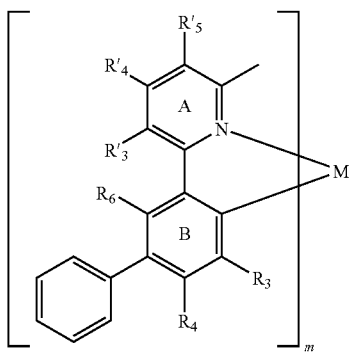
In one embodiment, the emissive materials comprises a molecule having a formula where M is Ir and m is 3 as depicted below:
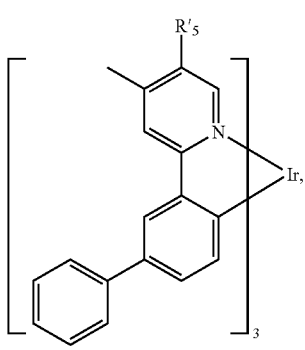
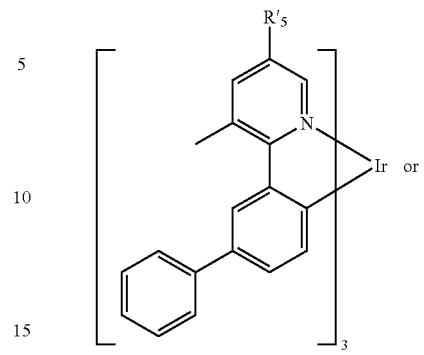
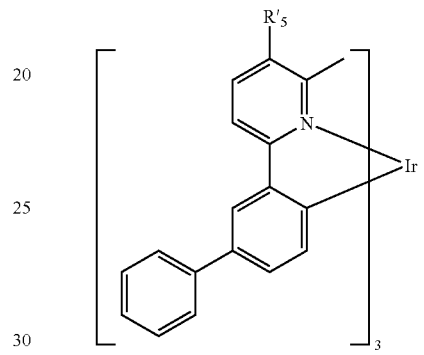
Where R$_5$, is defined according to the definitions of Formula I. In particular preferred embodiments R'$_5$ is methyl giving an emissive material of the formula:
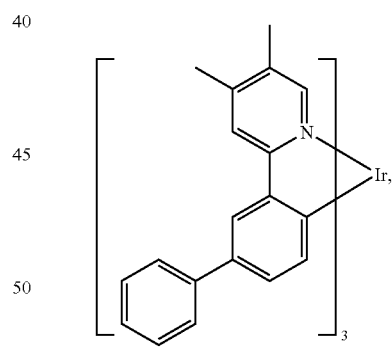
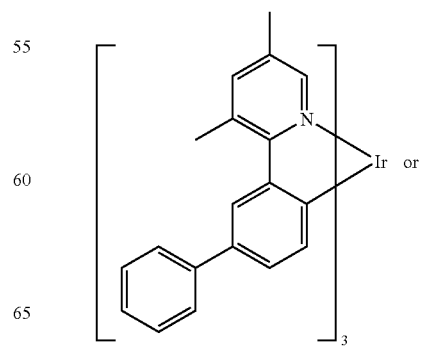

-continued

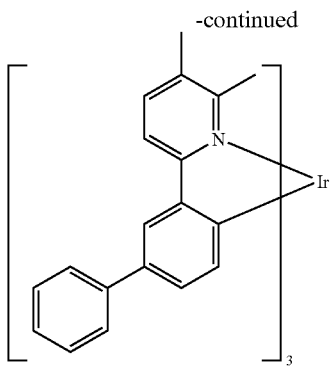

Figure 14:
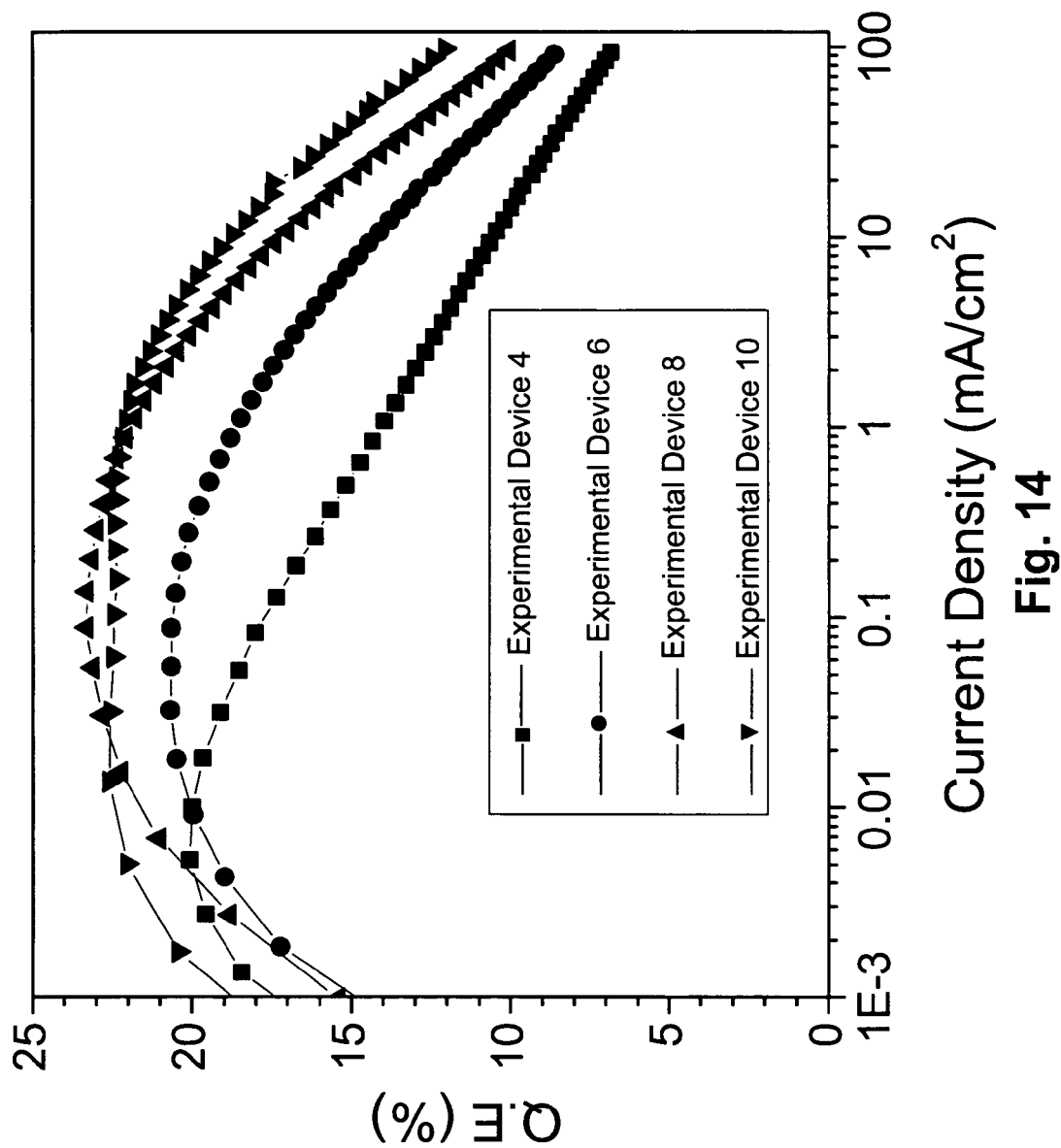
FIG. 14 shows the external quantum efficiency ($\eta_{ext}$) as a function of current density (mA/cm²) comparing devices using 50 Å of HPT as the ETL2 and using Ir(5'-Me-5-Phppy)₃ as the emissive material doped at 6% (Experimental Device 4), 8% (Experimental Device 6), 10% (Experimental Device 8) and 12% (Experimental Device 10).
Figure 15:
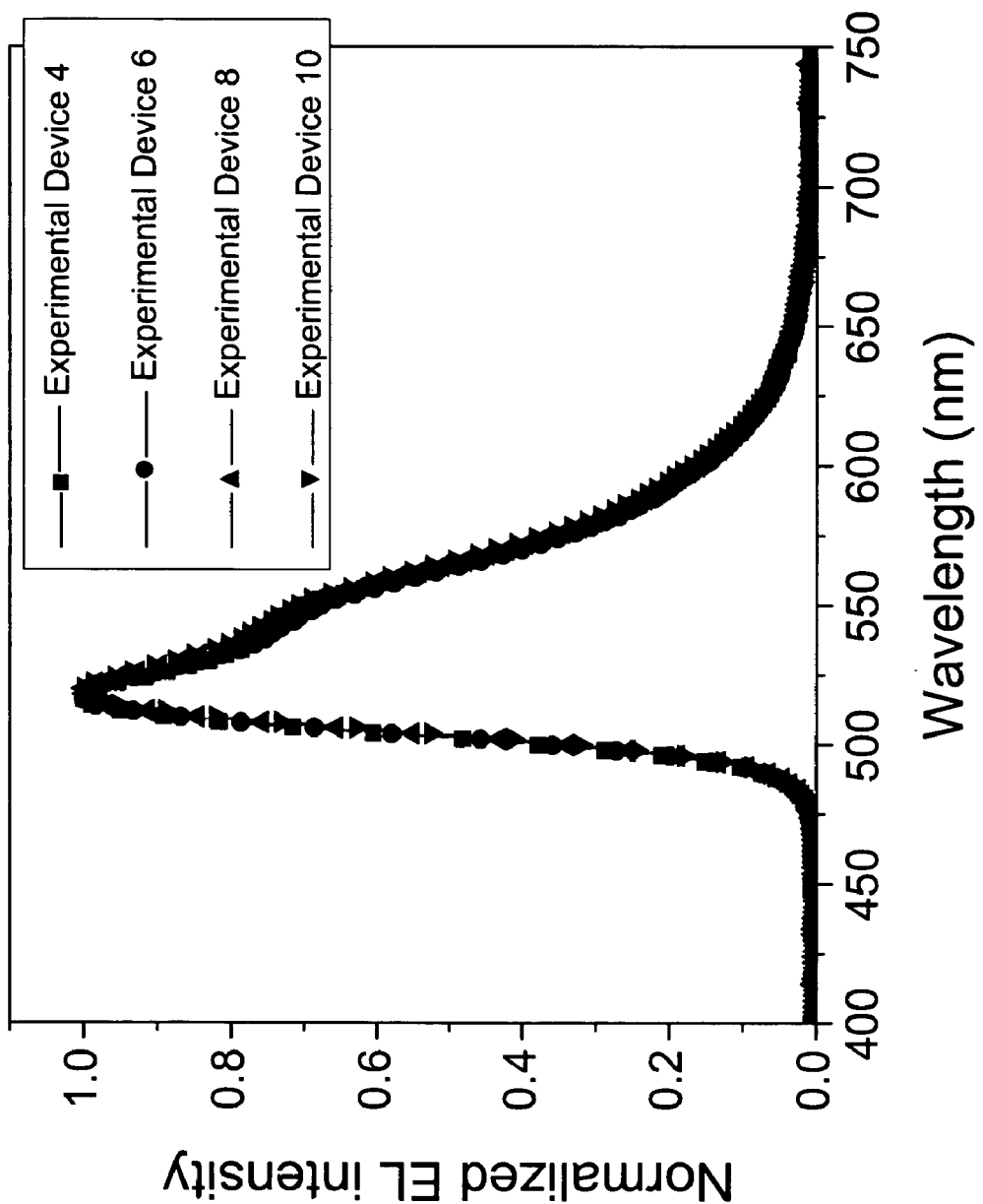
FIG. 15 shows the normalized electroluminescence spectra (normalized EL intensity vs. wavelength) at a current density of 10mA/cm² comparing devices using 50 Å of HPT as the ETL2 and using Ir(5'-Me-5-Phppy)₃ as the emissive material doped at 6% (Experimental Device 4), 8% (Experimental Device 6), 10% (Experimental Device 8) and 12% (Experimental Device 10).
Figure 16:
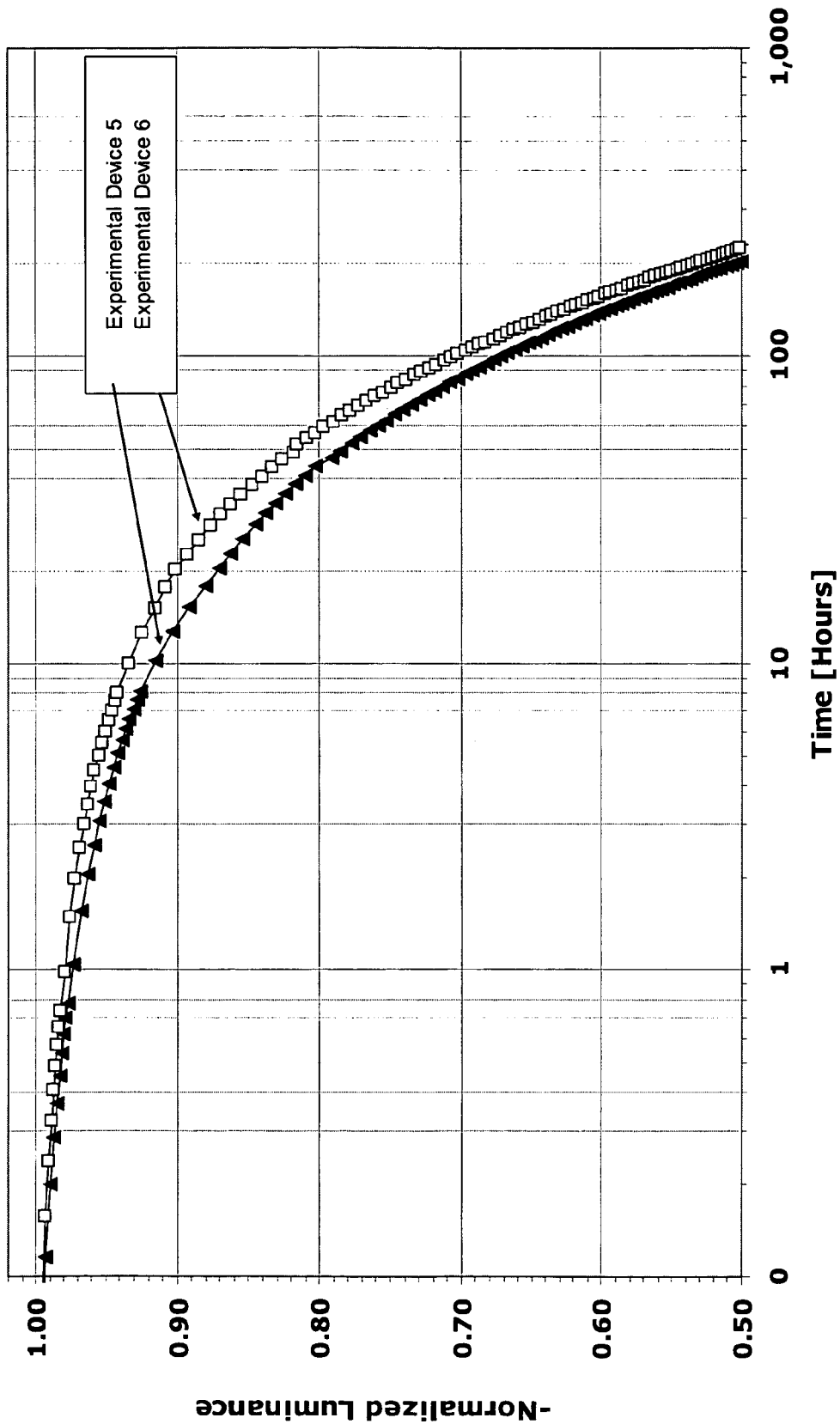
FIG. 16 shows the normalized luminance decay comparing devices with either 100 Å of aluminum(III)bis(2-methyl-8-hydroxyquinolinato)4-phenylphenolate (BAlq) as the ETL2 (Experimental Device 5) or 50 Å of HPT as the ETL2 (Experimental Device 6) using Ir(5'-Me-5-Phppy)₃ as the emissive material doped at 8% under constant current drive of 40 mA/cm² at room temperature.

Particular devices fabricated according to the present invention have exhibited a maximum external efficiency of 23% (FIG. 14) which we believe is higher than any thus far reported for OLEDs. Without being limited to any theory as to how the present invention works, it is believed that the alkyl substituent at position R'$_5$ as disclosed in Formula I leads to an emissive material resulting in high efficiency and operational stability when incorporated into an OLED device. In addition to exceptional efficiency, the light emitting devices of the present invention may exhibit an operational half-life in excess of about 50 hours, or preferably 100 hours, or even more preferably 200 hours at initial luminance of about 10,700 cd/m$^2$ or preferably 12,000 cd/m$^2$, or even more preferably 16,000 cd/m$^2$ or most preferably 17,000 cd/m$^2$. We have previously shown substitution at the R'$_3$ position to increase device lifetime as disclosed in U.S. patent application Ser. No. 10/765,295 to Kwong et al., now U.S. Pat. No. 7,279,232, which is incorporated by reference herein in its entirety. Substitution at the R$_5$ position has also been shown to increase device lifetime, as disclosed in U.S. patent application Ser. No. 10/289,915 to Brown et al. (now abandoned, published as US 2004/0086743), which is also incorporated by reference in its entirety.

In the present invention, alkyl substitution at the R'$_5$ position shows exceptional efficiency in particular devices. Substitution at the R$_5$ in addition to alkyl substitution R'$_5$ position may show a further improvement in efficiency over alkyl substitution at only the R'$_5$ position. For example, it is believed that specific substituents shown in Formula I provide a particularly efficient molecule, when R$_5$ is phenyl and R'$_5$ is methyl, both un-substituted. It is further believed that the enhanced efficiency is still present if the phenyl and/or methyl in the R$_5$ and R'$_5$ positions, respectively, are substituted.

As used herein, the term "external quantum efficiency" refers to the percentage of charge carriers injected into a device that result in the emission of a photon from the device in the forward direction. A number of factors can affect the external quantum efficiency, including the "internal quantum efficiency," which is the percentage of charge carriers injected into a device that result in the creation of a photon, and the "outcoupling efficiency," which is the percentage of photons created that are emitted from a device towards a viewer. In some embodiments of the present invention an organic layer comprising a 5'alkyl substituted dopant (with and without an aromatic hydrocarbon layer (HPT) that is in direct contact with an emissive layer) may enhance the internal quantum efficiency and thus the external quantum efficiency of the device. Because external quantum efficiency is more readily and directly measured than internal quantum efficiency, it may be desirable to describe certain aspects of the invention with respect to external quantum efficiency. But, in order to determine whether an enhanced external quantum efficiency is due to the use of an alkyl substituent at position 5', it is preferable to account for other factors that affect external quantum efficiency. The term "unmodified external quantum efficiency" as used herein refers to the external quantum efficiency of a device, after multiplication by a factor to account for any differences in the outcoupling efficiency of that device and the outcoupling efficiency of the devices described experimentally herein. For example, a device having an external quantum efficiency of 5%, but having an outcoupling efficiency 3 times better than the devices described herein, would have an "unmodified external quantum efficiency" of 1.33% (one third of 5%). A typical outcoupling efficiency for the types of devices described herein is about 20-30%. There are device structures having better outcoupling efficiencies than the devices described herein, and it is anticipated that improvements to outcoupling efficiency will be made over time. Such improvements would enhance external quantum efficiency, but should not affect "unmodified" external quantum efficiency, and devices having such improvements may fall within the scope of the present invention.

"Stability" may be measured in a number of ways. One stability measurement is the operational stability of the electroluminescent device which can be measured in terms of operational half-life. The operational half-life is the time required for the luminance of the device to decay from the initial luminance ($L_0$) to 50% of its initial luminance ($L_{0.5}$) under constant current and at room temperature unless otherwise noted. Operational half-life depends upon luminance at which the device is operated, because a higher luminance generally corresponds to a faster decay in a particular device. Luminance may be measured in cd/m$^2$. Devices in accordance with embodiments of the present invention can advantageously have an operational half-life in excess of about 50 hours, preferably about 100 hours, more preferably about 200 hours at initial luminance of about 10,700 cd/m$^2$ preferably about 12,000 cd/m$^2$, more preferably about 16,000 cd/m$^2$, most preferably about 17,000 cd/m$^2$ or higher.

The emissive material of the present invention may comprise a compound of Formula I such that the device has an unmodified external quantum efficiency of at least about 10% at current densities between about 0.1 to about 1000 mA/cm$^2$; and a lifetime of at least about 50 hours at an initial luminance of at least about 10700 cd/m$^2$. In another embodiment, the emissive material may comprise a compound of Formula I such that the device has an unmodified external quantum efficiency of at least about 15%, preferably at least about 20% at current densities from about 0.1 to about 1000 mA/cm$^2$; and a lifetime of at least about 50 hours at an initial luminance of at least about 10,700 cd/m$^2$. In yet another embodiment, the emissive layer may be in direct contact with an electron transport layer comprising a material having a molecular dipole moment less than about 2.0 debyes, such that the device has an external quantum efficiency of at least about 10% at about at current densities between about 0.1 to about 1000 mA/cm$^2$.

In one embodiment, it is believed that the use of a second electron transport layer (ETL2) including an aromatic hydrocarbon having a zero or low molecular dipole moment (TPD) adjacent to the emissive layer may further enhance device performance, as disclosed in U.S. patent application Ser. No. 10/785,287 now abandoned, published as US 2005/0025993) which is incorporated by reference in its entirety herein. Without intending to limit all embodiments with a particular theory of how the invention works, it is believed that this symmetric energy structure may improve electron injection from ETL2 into the emissive layer. The (ETL2) may be in direct contact with the cathode, or there may be a separate organic layer between the organic enhancement layer and the cathode. Other aromatic hydrocarbon materials may be used.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:

| | |
|---|---|
| CBP: | 4,4'-N,N-dicarbazole-biphenyl |
| m-MTDATA | 4,4',4''-tris(3-methylphenylphenylamino)triphenylamine |
| Alq₃: | 8-tris-hydroxyquinoline aluminum |
| Bphen: | 4,7-diphenyl-1,10-phenanthroline |
| n-BPhen: | n-doped BPhen (doped with lithium) |
| F₄-TCNQ: | tetrafluoro-tetracyano-quinodimethane |
| p-MTDATA: | p-doped m-MTDATA (doped with F₄-TCNQ) |
| Ir(ppy)₃: | tris(2-phenylpyridine)-iridium |
| Ir(ppz)₃: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | N,N'-diphenyl-N-N'-di(1-naphthyl)-benzidine |
| TPD: | N,N'-diphenyl-N-N'-di(3-tolyl)-benzidine |
| BAlq: | aluminum(III)bis(2-methyl-8-hydroxy-quinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT:PSS: | an aqueous dispersion of poly(3,4-ethylenedioxythiophene) with polystyrenesulfonate (PSS) |
| HPT: | 2,3,6,7,10,11-hexaphenyltriphenylene |

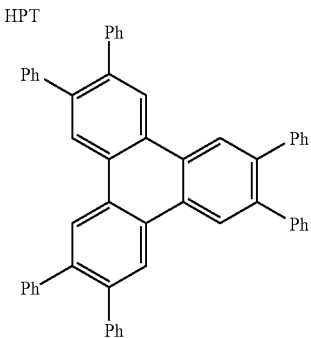

EXPERIMENTAL

Specific representative embodiments of the invention will now be described, including how such embodiments may be made. It is understood that the specific methods, materials, conditions, process parameters, apparatus and the like do not necessarily limit the scope of the invention.

Compound I tris[5-methyl-2-phenylpyridine-N,C²']iridium (III) [Ir(5'-Meppy)₃] Synthesis Step 1: Synthesis of 3-methyl-6-phenylpyridine

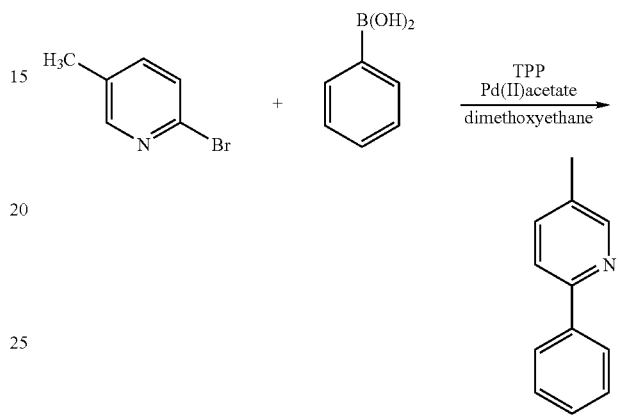

To a 2 L flask, 45.0 g (262 mmol) of 6-bromo-3-methylpyridine, 38.3 g (314 mmol) of phenylboronic acid, 1.47 g (6.54 mmol) of palladium acetate, 6.86 g (26.2 mmol) of triphenylphosphine and 353 mL of 2M K₂CO₃ were added to 405 mL of dimethoxyethane. The mixture was heated at reflux for 20 hours and cooled to room temperature. The aqueous phase was extracted twice with 200 mL of ethyl acetate. The combined organic extractions were then extracted with brine and dried over magnesium sulfate. The filtrate was evaporated in vacuo and the resultant oil purified by Kugelehor distillation (190° C. @ 500 microns) to give 37.2 g (84.1% yield) of 3-methyl-6-phenylpyridine as white solids.

Step 2 Synthesis of tris[5-methyl-2-phenylpyridine-NC²'] iridium (III)

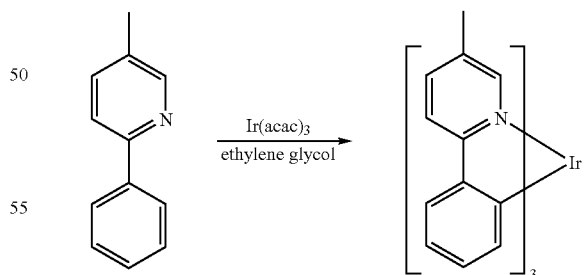

To a 100 mL round bottom flask containing 40 mL of ethylene glycol degassed at 180° C., then cooled to room temperature, was added 3.0 g (17.7 mmol) of 3-methyl-6-phenylpyridine and 2.18 g (4.43 mmol) of Ir(acac)₃. The reaction mixture was stirred for 20 hours at 175° C. under N2. The cooled material was then poured into EtOH and the solids collected by filtration and rinsed with EtOH. These solids were dissolved in CH₂Cl₂ and purified on a silica gel column using CH$_2$Cl$_2$/hexanes as eluent. The pure fractions were evaporated of solvent and the solids recrystallized from CH$_2$Cl$_2$/MeOH to give ~1 g of the product after filtration, MeOH rinse and drying. The solids were finally vacuum evaporated to give 0.50 g of Ir(5'-Meppy)$_3$ (98.9% assay) and was confirmed by NMR as the facial isomer.

Compound II tris[2-(biphenyl-3-yl)-5-methylpyridine]iridium(III) [Ir(5'-Me-5-Phppy)$_3$] Synthesis Step 1—Synthesis of 2-(3-bromophenyl)-5-methylpyridine

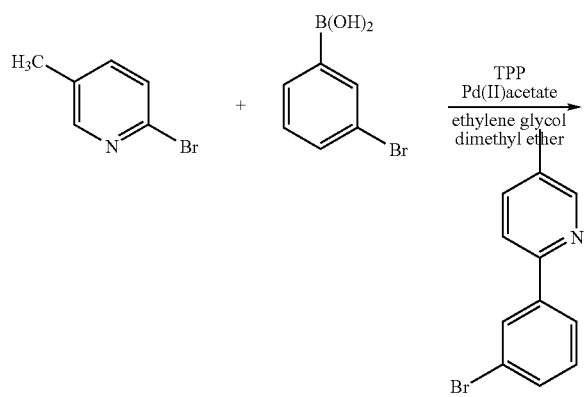

2-Bromo-5-methylpyridine (46.1 g, 267 mmol), 3-bromophenylboronic acid (35.8 g, 178 mmol), palladium(II) acetate (1.00 g, 4.4 mmol), triphenylphosphine (4.67 g, 17.8 mmol), and potassium carbonate (67.8 g, 491 mmol) were mixed with 370 mL of ethylene glycol dimethyl ether and 245 mL of water in a 1000 mL round bottom flask equipped with a temperature probe, reflux condenser, and a magnetic stir bar. The solution was heated at reflux under nitrogen for 16 hr. The cooled reaction mixture was then placed in a separatory funnel, and 100 mL of ethyl acetate was added. The aqueous layer was discarded. The organic layer was extracted twice with a saturated solution of sodium chloride, dried over magnesium sulfate, and evaporated to dryness. After the excess 2-bromo-5-methylpyridine was distilled off in vacuo at 110° C., the 2-(3-bromophenyl)-5-methylpyridine was distilled at 200° C. to give 30.1 g (68.1% yield) of a slightly orange liquid, which was used for the next step without further purification.

Step 2 Synthesis of 2-biphenyl-3-yl-5-methylpyridine

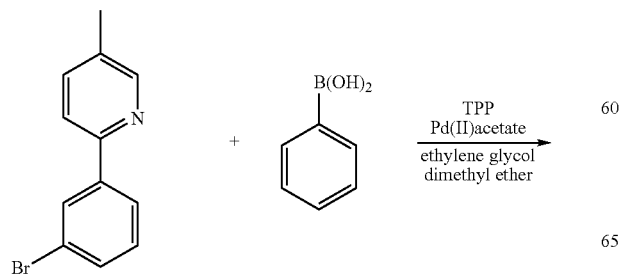

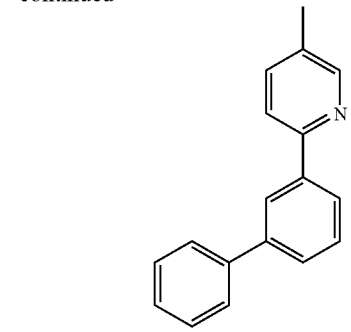

2-(3-bromophenyl)-5-methylpyridine (14.0 g, 61 mmol), phenylboronic acid (8.8 g, 72 mmol), palladium (II) acetate (0.34 g, 1.5 mmol), triphenylphosphine (1.6 g, 6.1 mmol), and potassium carbonate (22.3 g, 162 mmol) were mixed with 120 mL of ethylene glycol dimethyl ether and 80 mL of water in a 500 mL round bottom flask equipped with a temperature probe, reflux condenser, and a magnetic stir bar. The solution was then heated at reflux under nitrogen for 16 hr. The cooled reaction mixture was placed in a separatory funnel, and 100 mL of ethyl acetate was added. The aqueous layer was discarded. The organic layer was extracted twice with a saturated solution of sodium chloride, dried over magnesium sulfate, and evaporated to dryness. After the removal of several impurities by vacuum distillation at 115° C., distillation at 190° C. gave 13.7 g of 2-biphenyl-3-yl-5-methylpyridine as a viscous light yellow liquid, which was further purified on a silica gel column with ethyl acetate/hexane to give 12.8 g (87.1% yield) of 2-biphenyl-3-yl-5-methylpyridine as a white solid.

Step 3—Synthesis of tris[2-(biphenyl-3-yl)-5-methylpyridine-N,C$^{2'}$] iridium (III)

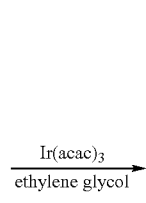

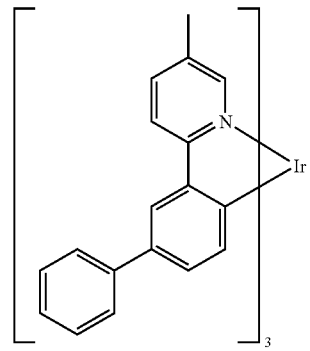

To a 100 mL three-neck round bottom flask equipped with a temperature probe, reflux condenser, nitrogen inlet, and a mechanical stirrer was added 30 mL of ethylene glycol. Nitrogen was then bubbled through the solvent at reflux for 1 hr after which time the 2-biphenyl-3-yl-5-methylpyridine (7.75 g, 31.6 mmol) was added. After the solution had become homogeneous, Ir(acac)$_3$ (3.87 g, 7.9 nmol) was added. The reaction mixture was heated at reflux under nitrogen for 24 h, resulting in a yellow precipitate. Methanol (60 mL) was added to the cooled reaction mixture, and the precipitate was collected by vacuum filtration and washed with methanol to give 5.7 g (78.1 yield %) of tris[2-(biphenyl-3-yl)-5-methylpyridine-N,C$^{2'}$] iridium (III).

Compound III

Comparative Example Compound tris(2-[3-biphenyl]pyridine) Iridium (III): [Ir(5-Phppy)$_3$] Synthesis

[Ir(5-Phppy)$_3$] was synthesized by the method described in U.S. Application Publication No. 2004/0086743, Example 1, to give tris(2-[3-biphenyl]pyridine) Iridium (III):

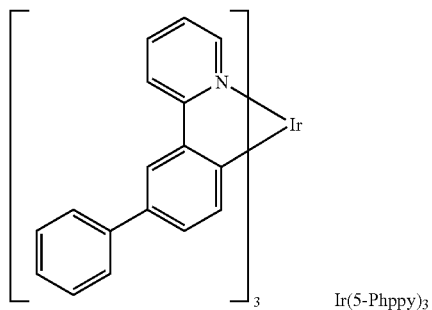

Ir(5-Phppy)$_3$

Compound IV fac tris[1-phenyl-4-methylisoquinolinolato-N,C$^{2'}$] iridium(III) [Ir(4-Me-1-piq)$_3$] Synthesis Step 1—Synthesis of N-(2-phenylpropyl)benzamide

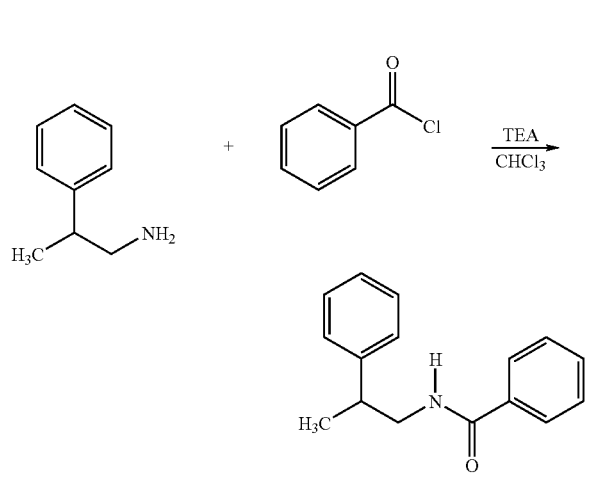

To a solution of 1-amino-2-phenylpropane (25.0 g, 0.185 mol) and triethylamine (18.2 g, 0.185 mol) in 150 mL of chloroform was added dropwise, a solution of benzoyl chloride (26.0 g, 0.185 mol) in 150 mL of chloroform under nitrogen. After completion of the addition, the reaction mixture was heated at reflux for 1 hour. The solution was then washed with water and the organic layer dried over magnesium sulfate. Removal of the solvent yielded 42.0 g (95%) of N-(2-phenylpropyl)benzamide as a white powder.

Step 2—Synthesis of 1-phenyl-4-methyl-3,4-dihydroisoquinoline

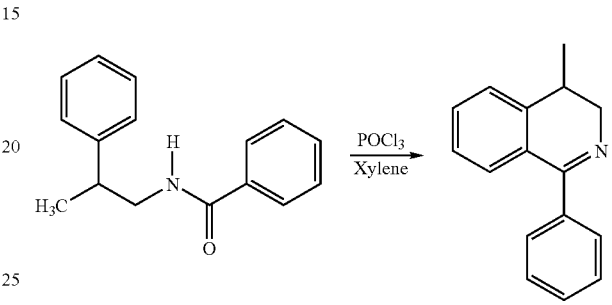

To a suspension of phosphorus oxychloride (224 g, 136 mL, 1.46 mol) and phosphorus pentoxide (136 g, 0.480 mol) in 410 mL of dry xylene was added N-(2-phenylpropyl)benzamide (40 g, 0.167 mol). The suspension was heated with stirring at reflux for 4 h under nitrogen. After cooling to room temperature, the solvent was decanted off. The reaction vessel was then placed in an ice bath, and the residue was dissolved in ice water. Basification with 50% aqueous potassium hydroxide yielded a white precipitate, which was then stirred with dichloromethane and filtered. The solids were discarded. After drying over magnesium sulfate, the dichloromethane was removed by rotary evaporation, yielding 29.0 g (78%) of 1-phenyl-4-methyl-3,4-dihydroisoquinoline as a yellow oil, which was used for the next reaction without further purification.

Step 3—Synthesis of 1-phenyl-4-methylisoquinoline

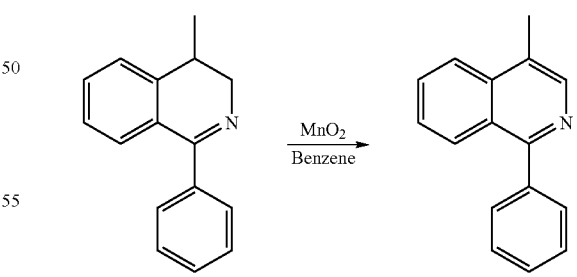

To a suspension of activated magnesium dioxide (270 g, 0.132 mol) in 550 mL of benzene was added 1-phenyl-4-methyl-3,4-dihydroisoquinoline (29.0 g, 0.131 mol) with stirring. The reaction mixture was heated at reflux for 16 hours. The magnesium dioxide was removed by vacuum filtration and washed with methylene chloride. Evaporation of the solvent yielded 12.2 g (42%) of pure yellow crystals of 1-phenyl-4-methylisoquinoline.

Step 4—Synthesis of Bis[1-phenyl-4-methylisoquinolinato-N,C2']iridium (III) μ-dichloro-bridged dimer.

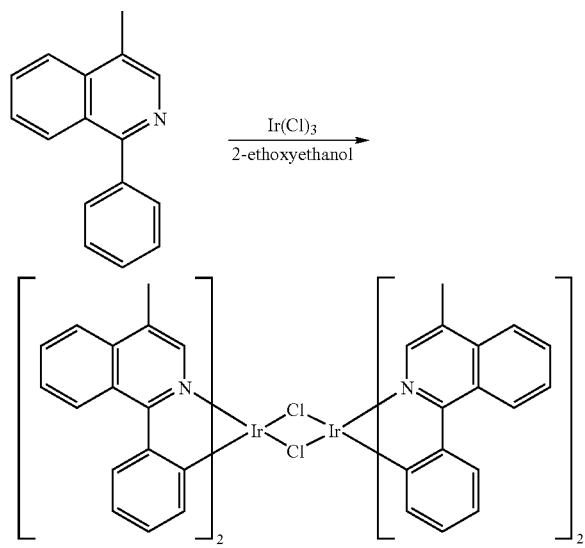

A suspension of 1-phenyl-4-methylisoquinoline (6.0 g, 27.4 mmol) and iridium chloride (5.0 g, 13.7 mmol) in 75 mL of 2-ethoxyethanol and 20 mL of water was heated at reflux for 36 h under nitrogen, resulting in a red precipitate, which, after cooling, was collected by vacuum filtration and washed with methanol, followed by hexane, yielding 6.5 g (67%) of bis[1-phenyl-4-methylisoquinolinato-N,C2']iridium (III) μ-dichloro-bridged dimer.

Step 5-Bis(1-phenyl-4-methylisoquinolinato-N,C2') iridium (III) acetylacetonate

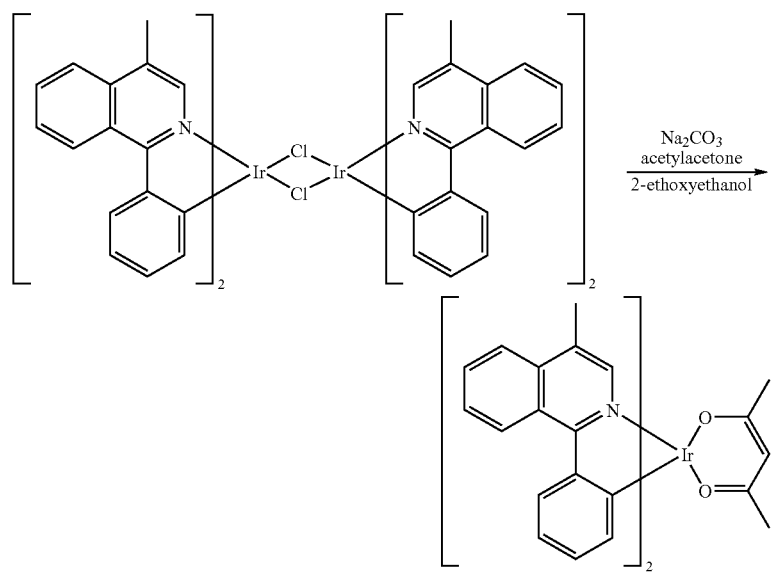

A suspension of bis[1-phenyl-4-methylisoquinolinato-N, C2']iridium (III)) 1-dichloro-bridged dimer (6.5 g, 4.9 mmol), acetylacetone (4.9 g, 49 mmol), and sodium carbonate (10.3 g, 98 mmol) in 160 mL of 2-ethoxyethanol was heated at reflux under nitrogen fro 14 hours. After cooling, the product was collected by vacuum filtration and washed with water, followed by methanol, yielding 2.6 g (37%) of bis(1-phenyl-4-methylisoquinolinato-N,C2')iridium acetylacetonate.

Step 6—tris[1-phenyl-4-methylisoquinolinolato-N, C2'] iridium(III)

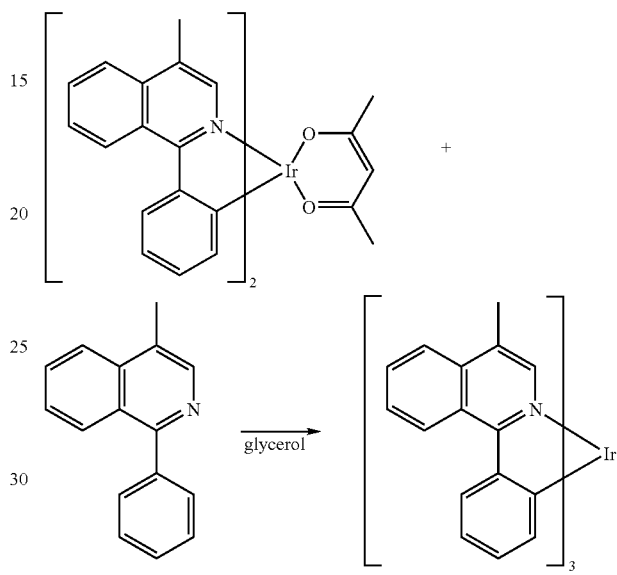

A suspension of bis(1-phenyl-4-methylisoquinolinato-N, C2')iridium(acetylacetonate) (2.3 g, 3.1 mmol) and 1-phenyl-4-methylisoquinoline (2.7 g, 12.3 mmol) were heated with stirring in 50 mL of glycerol under nitrogen for 24 hours yielding 1.9 g (73%) of crude iridium, tris[1-phenyl-4-methylisoquinolinolato-N,C2'] iridium(III). Purification on a silica gel column using 70/30 dichloromethane/hexane as the mobile phase yielded 0.9 g (33% yield). The product (375 mg) was then purified by vacuum evaporation (Z-1=180° C., Z2=220° C., Z3=280° C., 1×10$^{-5}$ torr) yielding 100 mg of the desired product.

V fac tris[3-methyl-5,6 dihydrobenzo [h] quinolinato-N,C$^{2'}$] iridium(III) [Ir(3-Me-dhbq)$_3$] Synthesis Step 1: 2-methylene-3,4-dihydronaphthalen-1-one

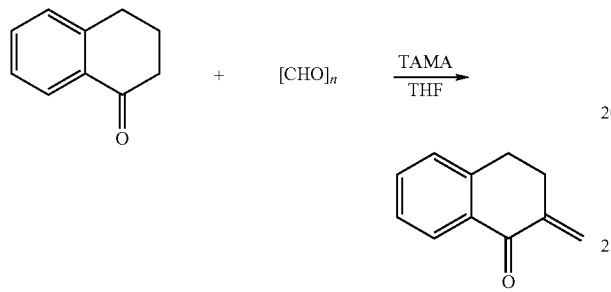

To a suspension of paraformaldehyde (46.2 g, 1.54 mol) and N-methylanilinium trifluoroacetate (TAMA, 46.2 g, 1.54 mol) in 340 mL of dry THF was added α-tetralone (50 g, 0.342 mol). The solution was heated at reflux under nitrogen with stirring for 4 h, during which time the paraformaldehyde dissolved. After cooling, diethyl ether (700 mL) was added to the reaction mixture. The solvent was separated from the reaction mixture and washed with 500 mL of saturated sodium bicarbonate. Additional diethyl ether was added to the reaction mixture, separated and used to back extract the aqueous sodium bicarbonate layer. The combined organic layers were dried over magnesium sulfate, and the solution was then concentrated to a volume of approximately 300 mL and filtered through Celite. Complete evaporation of the ether yielded 50 g (90%) of crude 2-methylene-3,4-dihydronaphthalen-1-one, which was used immediately for the next reaction to prevent polymerization of the product.

Step 2: 2-ethoxy-3-methyl-3,4,5,6-tetrahydrobenzo [h]chromene

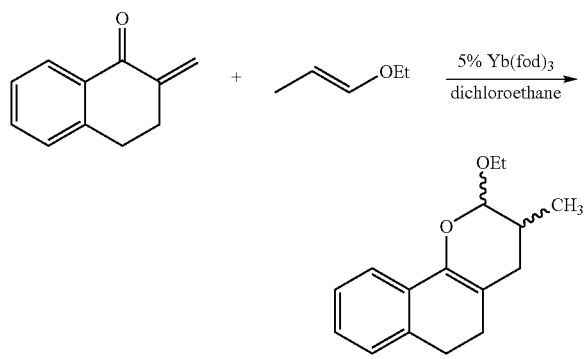

A solution of 2-methylene-3,4-dihydronaphthalen-1-one (44.9 g, 282 mmol), tris(6,6,7,7,8,8,8-heptafluoro-2,2-dimethyl-3,5-octanedionato)ytterbium [Yb(fod)$_3$, 15.0 g, 14.2 mmo], and ethyl propenyl ether (300 g, 390 mL, 3.5 mol) in 830 mL of dichloroethane was heated at reflux under nitrogen with stirring for 20 hours. Evaporation of the solvent left 200 g of a brown liquid that was purified on a silica gel column with 15/85 ethylacetate/hexane as the eluent, yielding 140 g of product, which was used without further purification.

Step 3: 3-methyl-5,6-dihydrobenzo[h]quinoline

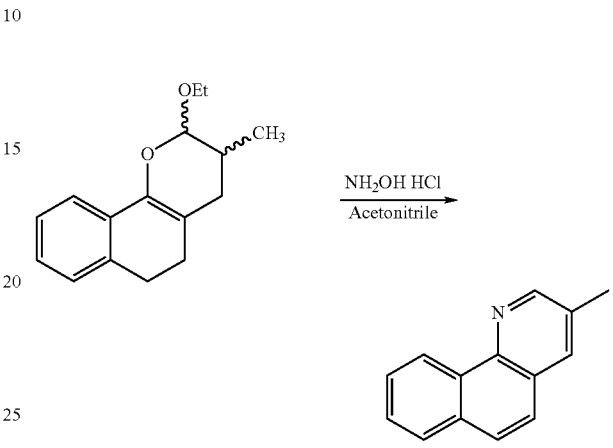

To a suspension of hydroxylamine hydrochloride (46.1 g, 0.663 mol) in 1070 mL of acetonitrile was added 2-ethoxy-3-methyl-3,4,5,6-tetrahydrobenzo[h]chromene (140 g, 0.265 mol) from step two. The reaction mixture was heated at reflux under nitrogen with stirring for 16 h. Evaporation of the acetonitrile, followed by vacuum distillation of the product yielded 34.5 g of a crude product that was further purified by silica gel chromatography with 5/95 ethyl acetate/hexane as the eluent, yielding 23.2 g (45%) of 5,6-dihydrobenzo[h]quinoline as a yellow liquid.

Step 4: fac tris[3-methyl-5,6-dihydrobenzo[h]quinolinato-N,C$^{2'}$] iridium(III)+

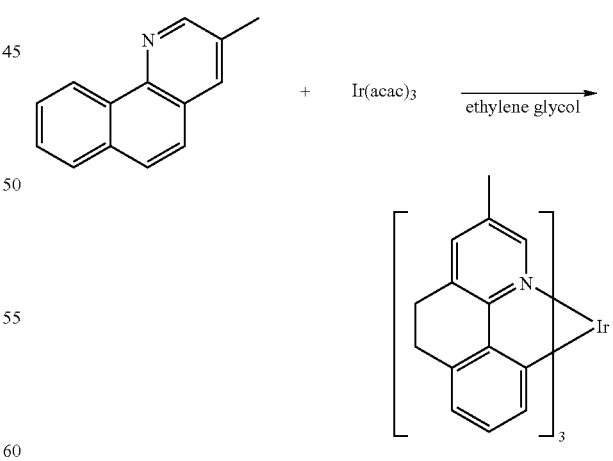

To 50 mL of ethylene glycol at reflux under a nitrogen atmosphere were added 10.2 g (52.2 mmol) of 3-methyl-5,6-dihydrobenzo[h]quinoline. To this solution were then added 6.4 g (13.1 mmol) of Ir(acac)$_3$, and the reaction mixture was maintained at reflux for 3 h, resulting in the formation of a yellow precipitate. The mixture was then cooled and diluted with methanol, and the product was collected by vacuum filtration and washed with methanol, yielding 6.0 g (59%) of a yellow powder, which was purified by silica gel column chromatography using 70/30 dichloromethane/hexane as the eluent, yielding 3.8 g (37%) of product that was then recrystallized from 140 mL of 1,2-dichlorobenzene to give 3.3 (32%) of yellow needles. Vacuum evaporation ($Z_1$=190° C., $Z_2$=220° C., $Z_3$=275° C., $1\times10^{-5}$ torr) yielded 2.4 g (24%) of pure product.

Compound VI fac tris[2-(2'-methylbiphenyl-3-yl)pyridinato-N,$C^{2'}$] iridium(III) (Ir[5'-Me-5-(2-MePh)ppy]$_3$) Synthesis Step 1: 2-(3-bromophenyl)-5-methylpyridine

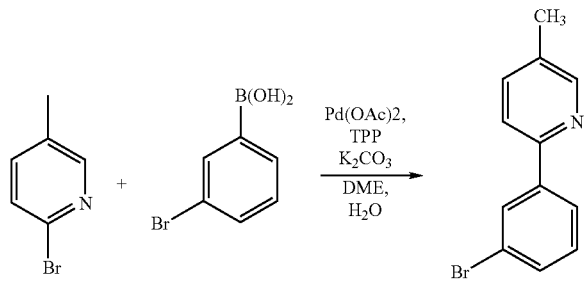

To a solution of 2-bromo-5-methylpyridine (46.1, 267 mmol), 3-bromophenylboronic acid (35.8 g, 178 mmol), palladium (II) acetate (1.0 g, 4.4 mmol), and triphenylphosphine (4.8 g, 18.3 mmol) in dimethoxyethane (370 mL) was added a solution of potassium carbonate (67.8 g, 491 mmol) in 245 mL of water. The reaction mixture was heated at reflux under a nitrogen atmosphere for 16 h and cooled. Ethyl acetate was added, and the aqueous phase was discarded. Evaporation of the organic phase after drying over magnesium sulfate yielded a brown liquid from which the excess 2-bromo-5-methylpyridine was distilled in vacuo at 110° C. Further vacuum distillation at 200° C. yielded 30.1 g (68%) of 2-(3-bromophenyl)-5-methylpyridine as a light brown liquid.

Step 2: 2-(2'-methylbiphenyl-3-yl)5-methylpyridine

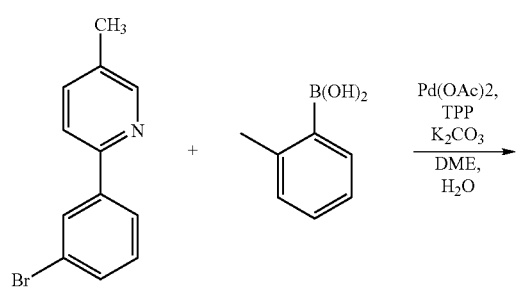

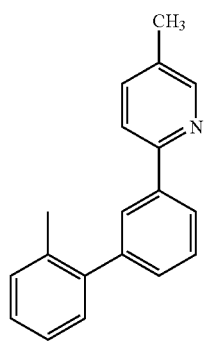

To a solution of 2-(3-bromophenyl)-5-methylpyridine (26.4 g, 106 mmol), o-tolylboronic acid (17.4 g, 128 mmol), palladium (II) acetate (0.60 g, 2.7 mmol), and triphenylphosphine (2.8 g, 10.7 mmol) in 215 mL of dimethoxyethane was added a solution of potassium carbonate (39.7 g, 287 mmol) in 145 mL of water. The reaction mixture was heated at reflux under a nitrogen atmosphere for 16 h and cooled. Ethyl acetate was added, and the aqueous phase was discarded. Evaporation of the organic phase after drying over magnesium sulfate yielded a yellow liquid that was then subjected to vacuum distillation at 160° C. to remove most of the impurities. Further distillation at 220° C. yielded 29.9 g of a colorless liquid that was further purified by silica gel column chromatography with 10/90 ethyl acetate/hexane as the eluent to give 22.5 g (81%) of pure 2-(2'-methylbiphenyl-3-yl)pyridine as a colorless, viscous liquid.

Step 3 Dimer

To a mixture of 2-ethoxyethanol (95 mL) and water (25 mL) were added 11.0 g (42.4 mmol) of 2-(2'-methylbiphenyl-3-yl)pyridine and 7.9 g (21.2 mmol) of IrCl$_3$. The reaction mixture was heated under a nitrogen atmosphere at reflux for 50 h and cooled. The yellow precipitate that formed was collected by vacuum filtration and washed with methanol and ethyl acetate to give 11.0 g (70%) of chloro-bridged dimer Step 4: fac tris[2-(2'-methylbiphenyl-3-yl)pyridinato-N,C²'] iridium(III)

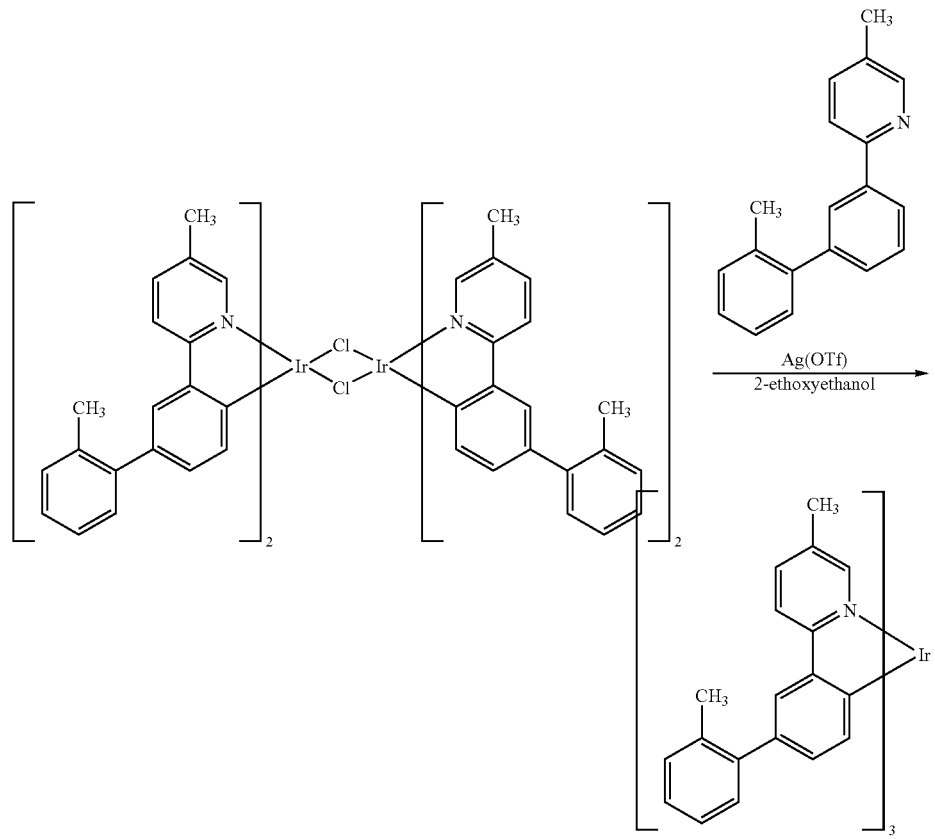

A suspension of dimer (11.0 g, 7.4 mmol), silver triflate (14.7 mmol), and 2-(2'-methylbiphenyl-3-yl)pyridine (7.6 g, 29.3 mmol) in 160 mL of 2-ethoxyethanol was heated under a nitrogen atmosphere at 95° C. for 60 h and then cooled. The precipitate was collected by vacuum filtration and washed with methanol to give 13.2 g of crude product that was then subjected to silica gel column chromatography with 50/50 dichloromethane/hexane as the eluent, yielding 4.5 g of pure product in addition to 4.1 g of more impure fractions. The pure fraction was recrystallized from 60 mL of a 90/10 toluene/hexane mixture to give 3.4 g (24%) of product that was then evaporated in vacuo to yield 0.9 g (6%) of pure fac tris[2-(2'-methylbiphenyl-3-yl)pyridine] iridium(III).

Compound VII

Hexadentate Ligand Complex Synthesis

Step 1: 2-(4-bromophenyl)-5-methylpyridine—

To a 500 mL round bottom flask, 4-bromophenylboronic acid (25.0 g, 0.125), 2-bromo-5-methylpyridine (20.0 g, 0.114 mol), palladium(0)tetrakistriphenylphosphine (4.0 g, 0.0035 mol), potassium carbonate (47.0 g, 0.34 mol.), 1,2-dimethoxyethane (120 mL) and water (120 mL.) were added. The mixture was heated to reflux under nitrogen atmosphere for 18 hours. After the reaction was cooled down, 100 mL of water and 150 mL of ethyl acetate were added. The mixture was separated in a separatory funnel. The organic phases were collected, combined and evaporated. The mixture was distilled using a kugelrohred (spelling?) to obtain 2-(4-bromophenyl)-5-methylpyridine (26.0 g) as a white solid that was further purified by recrystallization in hexanes.

Step 2

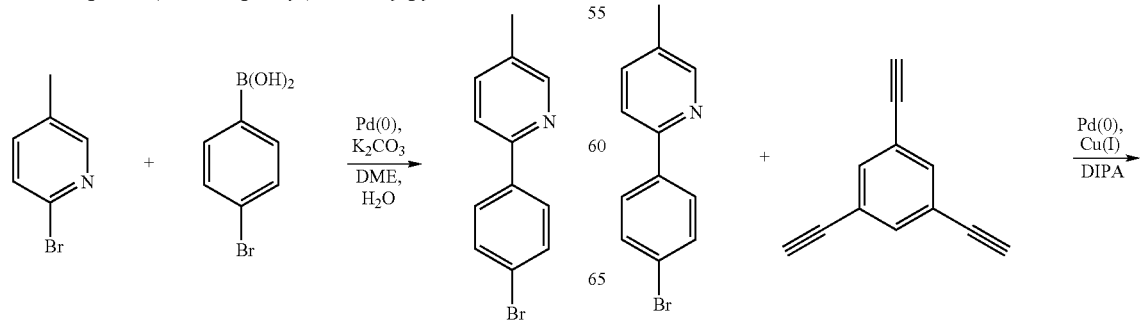

-continued

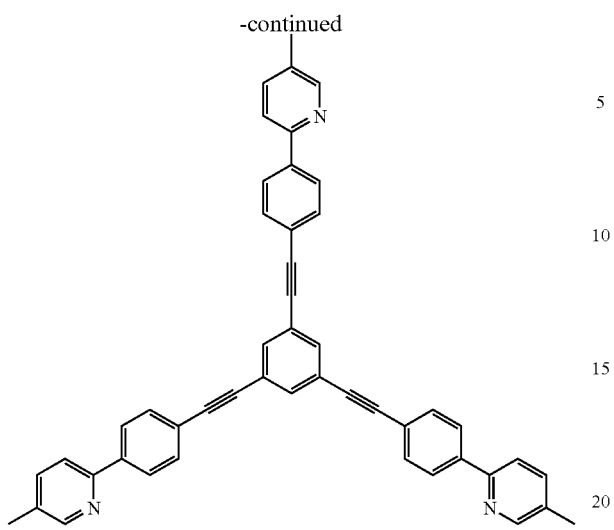

i. B 2-(4-Bromophenyl)-5-methylpyridine (9.3 g, 0.038 mol.) was added to a mixture of dry toluene (70 mL), dry diisopropylamine (70 mL), 1,3,5-triethynylbenzene (2.0 g, 0.0133 mol), palladium(0)tetrakistriphenylphosphine (1.4 g, 0.0012 mol), CuI (0.15 g) were added in a dry three-necked reaction flask. The mixture was stirred under nitrogen at room temperature for 3 hours, and then heated up to 60° C. for 2 days. The reaction mixture was cooled down and purified by silica gel column chromatography using dichloromethane/ethyl acetate as the eluent. The pure fractions were collected and concentrated to give Compound B (8.0 g) as a white solid.

Step 3

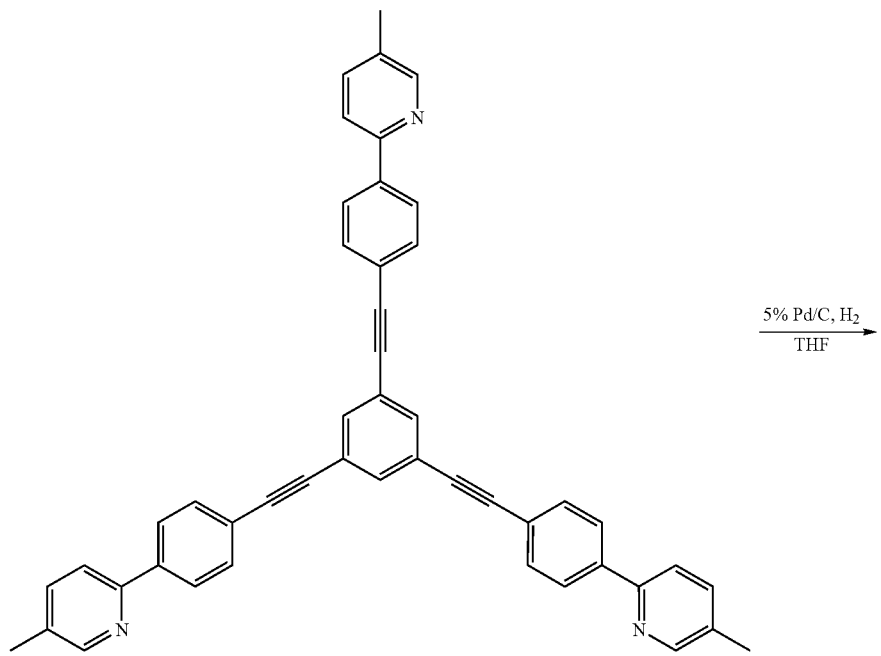

B

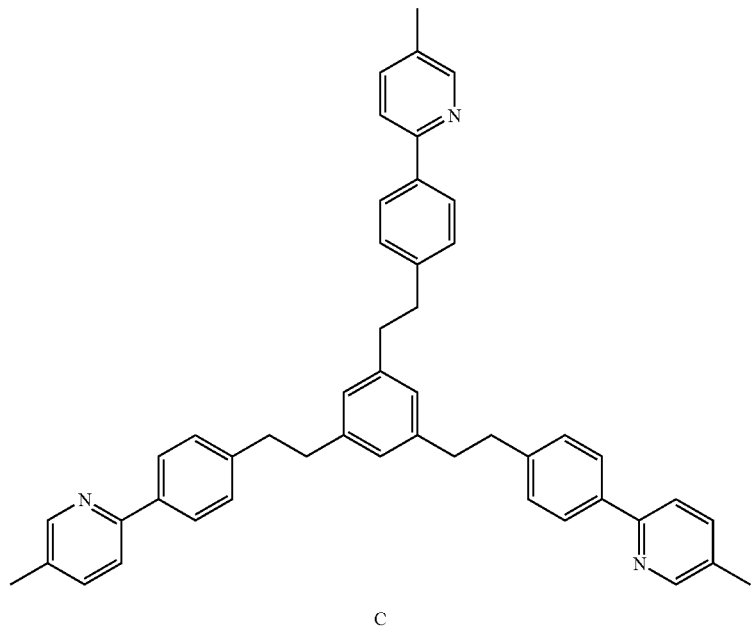

C

30

In a computer controlled hydrogenation apparatus, Compound B (10.0 g, 0.015 mol.), 5% Pd/C catalyst (5.0 g, 0.0024 mol.) and ~300 mL of THF were added in reactor. The reaction was placed under 45 psi of hydrogen pressure and stirred under room temperature overnight. After the reaction was completed the crude product was filtered and the solvent concentrated. The crude product was purified by a silica gel column chromatography using 30% ethyl acetate in hexane to give Compound C (9.0 g) as a white solid.

Step 4: Hexadentate Ligand Complex

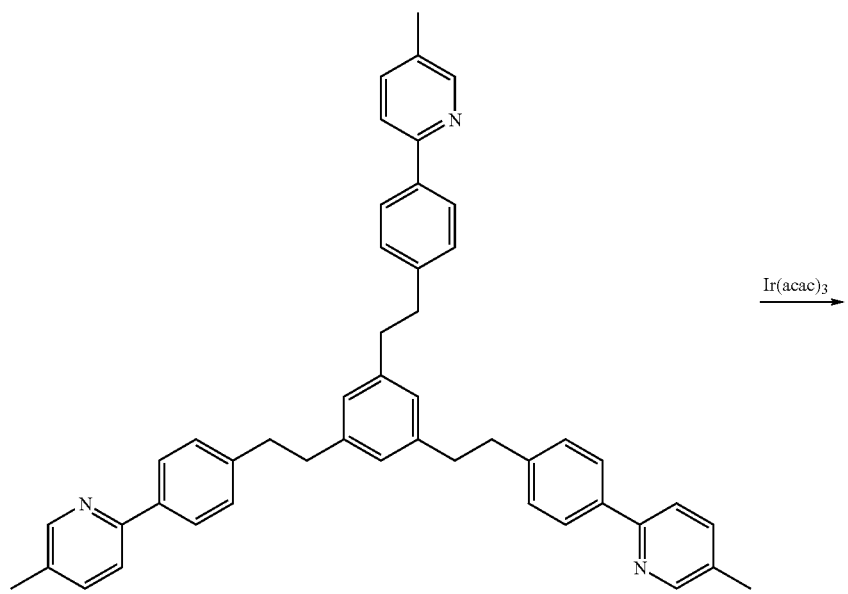

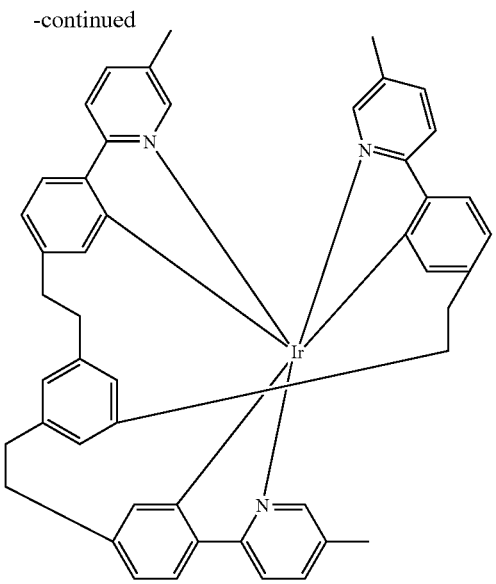

Approximately 70 mL of ethylene glycol, Ir(acac)₃, (0.76 mg, 0.00154 mol) and Compound C (1.0 g, 0.00151 mol) were added to a 100 mL round bottom flask. The reaction was heated to 160° C. under nitrogen atmosphere for 24 hours and then cooled down. Methanol was added and the yellow solid collected by vacuum filtration. The crude yellow product was purified by silica gel column chromatography using 40% dichloromethane in hexane to give the desired compound (900 mg) as a yellow solid.

Compound VIII fac tris[2-(4'-fluorobiphenyl-3-yl)-5-methylpyridine] iridium(III) ("Ir[5'-Me-5-(4-FPh)ppy]₃") Synthesis Step 1: 2-(3-bromophenyl)-5-methylpyridine

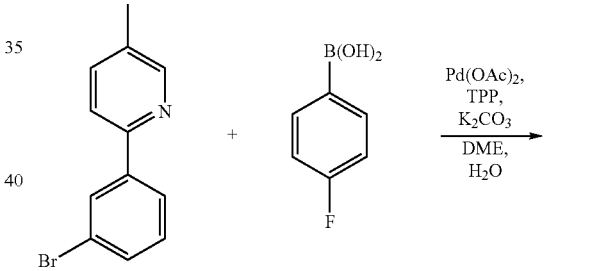

To a 500 mL. reaction flask were added together 2-bromo-5-methylpyridine (46.1 g, 267 mmol), 3-bromophenylboronic acid (35.8 g, 178 mmol), palladium (II) acetate (1.0 g, 4.4 mmol), triphenylphosphine (4.8 g, 18.3 mmol), dimethoxyethane (370 mL) and a solution of potassium carbonate (67.8 g, 491 mmol) in 245 mL of water. The reaction mixture was heated at reflux under a nitrogen atmosphere for 16 h and cooled. Ethyl acetate was added, and the aqueous phase was discarded. Evaporation of the organic phase after drying over magnesium sulfate yielded a brown liquid from which the excess 2-bromo-5-methylpyridine was distilled in vacuo at 110° C. Further vacuum distillation at 200° C. yielded 30.1 g (68%) of 2-(3-bromophenyl)-5-methylpyridine as a light brown liquid.

Step 2: 2-(4'-Fluorobiphenyl-3-yl)-5-methylpyridine

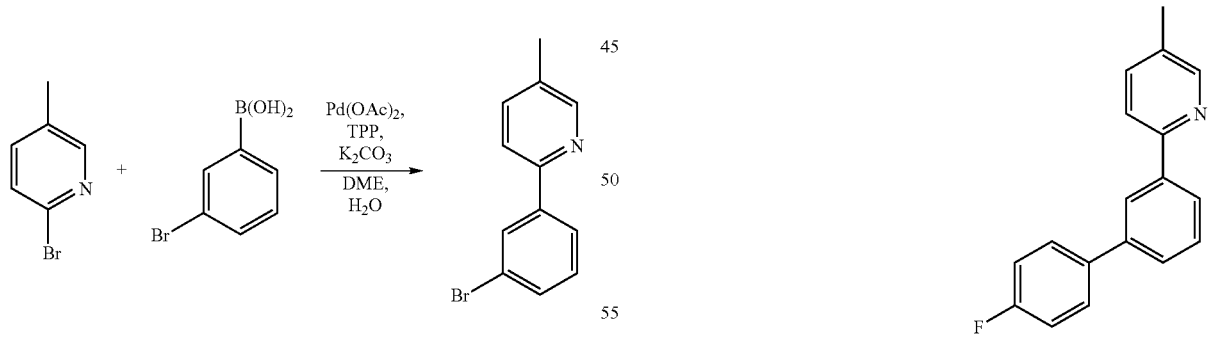

In a 500 mL. reaction flask added together 2-(3-bromophenyl)-5-methylpyridine (10. g, 40 mmol), 4-fluorophenylboronic acid (6.7 g, 48 mmol), palladium (II) acetate (0.22 g, 1.0 mmol), and triphenylphosphine (1 g, 4.0 mmol) in 200 mL of dimethoxyethane and a solution of potassium carbonate (12.7 g, 120 mmol) in 100 mL of water. The reaction mixture was heated at reflux under a nitrogen atmosphere for 16 h and cooled. Ethyl acetate was added, and the aqueous phase was discarded. The solvent was removed under vacuum and purified by silica gel column chromatography with 50/50 ethyl acetate/hexane as the eluents to give 9.0 g (91%) of 2-(4'-fluorobiphenyl-3-yl)-5'-methylpyridine as a colorless, viscous liquid.

Step 3: fac tris[2-(4'-fluorobiphenyl-3-yl)-5-methylpyridine] iridium(III)

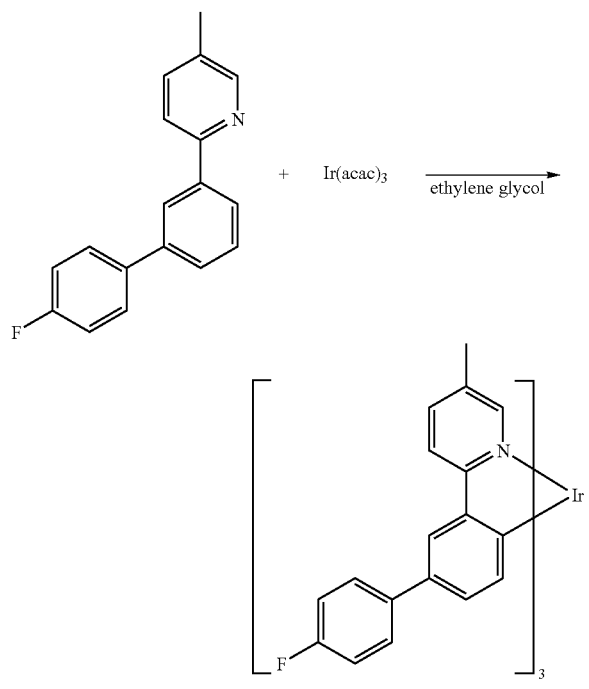

To ethylene glycol (100 mL) were added 2.8 g (10.6 mmol) of 2-(4'-fluorobiphenyl-3-yl)$_5$-methylpyridine and 1.7 g (3.6 mmol) of Ir(acac)$_3$. The reaction mixture was heated under a nitrogen atmosphere at reflux for 24 hours and cooled to room temperature. The yellow precipitate that formed was collected by vacuum filtration and washed with methanol followed by hexanes to give 1.4 g (40%) of the desired product. The crude product was purified by a silica gel column using methylene chloride as the eluent followed by crystallization using 2-methoxyethoxyethanol as the solvent.

Compound IX fac tris[2-(3'-fluorobiphenyl-3-yl)pyridine] iridium (III) ("Ir[5'-Me-5-(3-FPh)ppy]$_3$") Synthesis Step 1: 2-(3'-fluorobiphenyl-3-yl)pyridine

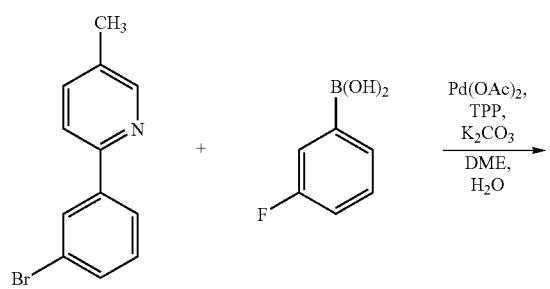

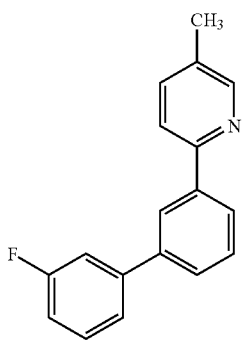

To a 500 mL. three-necked round bottom flask equipped with a stir bar, temperature probe, and a nitrogen inlet were added 2-(3-bromophenyl)-5-methylpyridine (14.7 g, 60 mmol), 3-fluorophenylboronic acid (10.0 g, 72 mmol), palladium (II) acetate (0.335 g, 1.5 mmol), triphenylphosphine (1.56 g, 6.0 mmol), sodium carbonate (17.0 g, 160 mmol), containing dimethoxyethane (120 mL.) and water (80 mL.). The solution was heated at reflux for twenty hours, cooled, and diluted with ethyl acetate. The organic layer was separated, dried over magnesium sulfate, and evaporated to dryness to give a brown liquid, which was purified by flash silica gel chromatography using a 5/95 to 10/90 ethyl acetate/hexane gradient, yielding a viscous, colorless liquid (12.5 g 80%).

Step 2: Synthesis of Dichlorobridge Dimer.

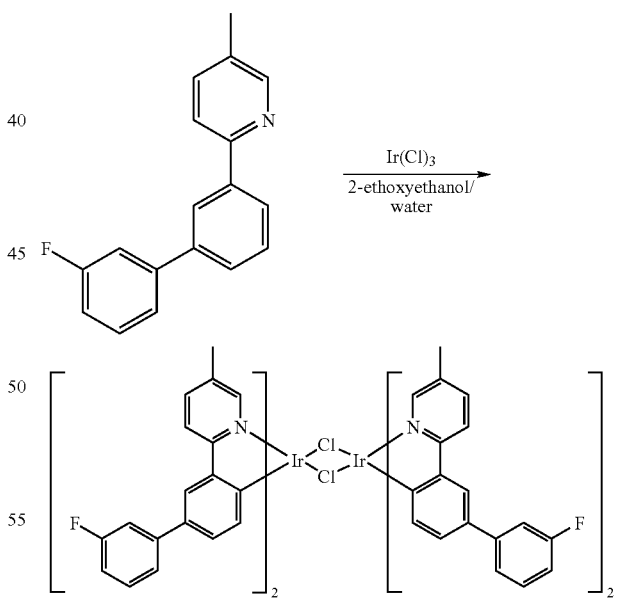

To a 250 mL. round-bottomed flask equipped with a stir bar, temperature probe, and a nitrogen inlet were combined of 2-(3'-fluorobiphenyl-3-yl)pyridine, Iridium chloride (4.4 g, 12 mmol), 2-ethoxyethanol (55 mL.), and 15 ml of water (15 mL.). The mixture was heated at reflux for two days. The resulting dimer (8.5 g, 48%) was collected by vacuum filtration and washed with methanol.

Step 3: fac tris[2-(3'-fluorobiphenyl-3-yl)pyridine] iridium(III)

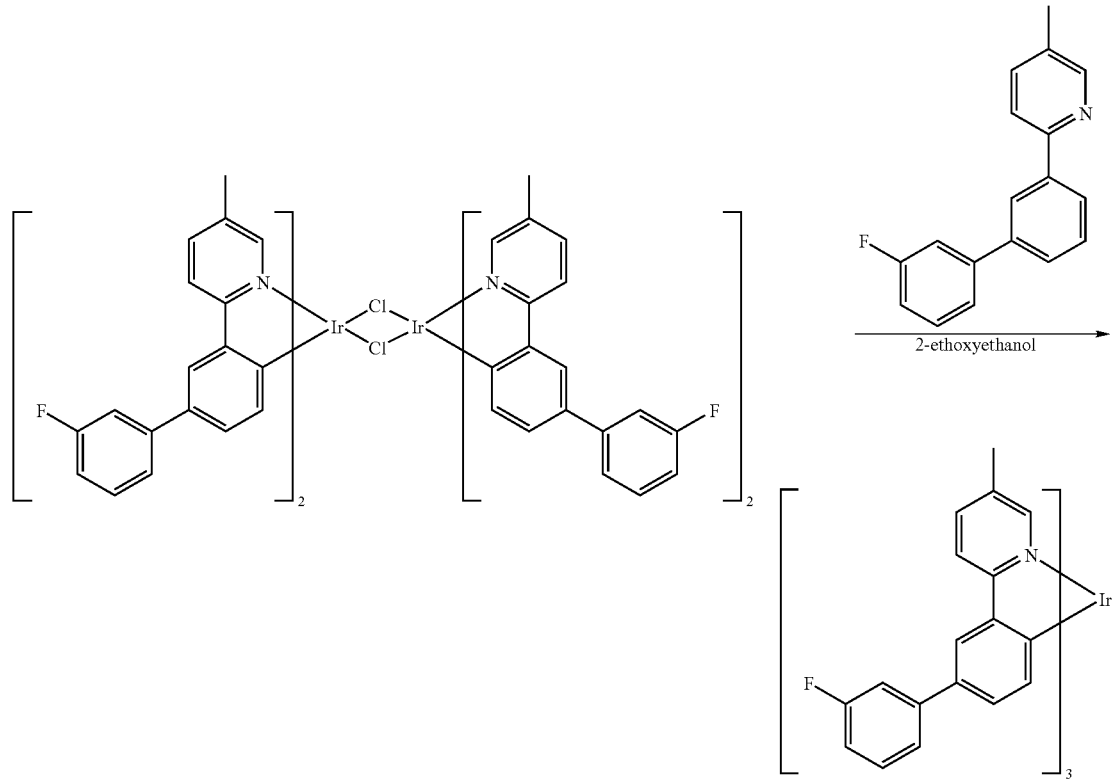

To a 500 mL, round-bottom flask equipped with a stir bar, temperature probe, and a nitrogen inlet was added dimer (8.5 g, 5.7 mmol), silver triflate (2.9 g, 11.3 mmol), 2-(3'-fluorobiphenyl-3-yl)pyridine (5.9 g, 22.5 mmol), and 2-ethoxyethanol (150 mL.). The mixture was heated at 95° C. for 6 days, resulting in a yellow green solid (12 g) that was collected by vacuum filtration and washed with methanol. Purification on a silica gel column with 70/30 methylene/chloride hexane as the eluents yielded of fac tris[2-(3'-fluorobiphenyl-3-yl)pyridine] iridium(III) 2.7 g (25%) as a yellow powder.

Compound X fac tris[2-(2'-fluorobiphenyl-3-yl)pyridine] iridium(III)

Synthesis

Step 1: 2-(2'-fluorobiphenyl-3-yl)pyridine

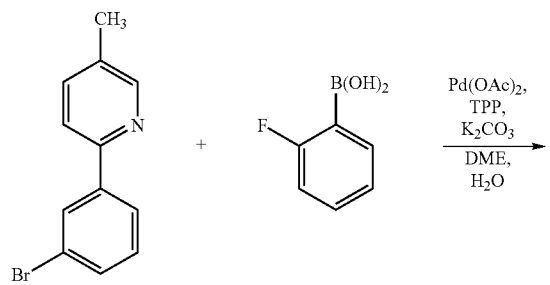

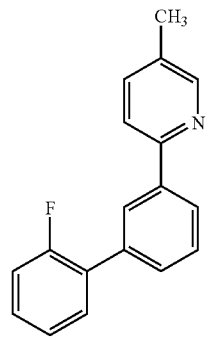

To a 500 mL, three-necked, round-bottomed flask equipped with a stir bar and a nitrogen inlet were added 2-(3-bromophenyl)-5-methylpyridine (12.0 g, 49 mmol), 2-fluorophenylboronic acid (8.2 g, 58.3 mmol), palladium (II) acetate (0.27 g, 1.2 mmol), triphenylphosphine (1.3 g, 4.8 mmol), sodium carbonate (13.0 g, 131 mmol), water (70 mL.) and dimethoxyethane (100 mL.). The reaction mixture was heated for 20 hours at reflux, cooled, and diluted with ethyl acetate. The organic layer was separated, dried over magnesium sulfate, and evaporated to dryness to give 12.0 g of a dark brown liquid that was purified by flash silica gel column chromatography using a gradient of 5-10/90-95 ethyl acetate/hexane, yielding 9.6 g of 2-(2'-fluorobiphenyl-3-yl)pyridine as a waxy white solid (75%).

Step 2: fac tris[2-(2'-fluorobiphenyl-3-yl)pyridine] iridium(III)

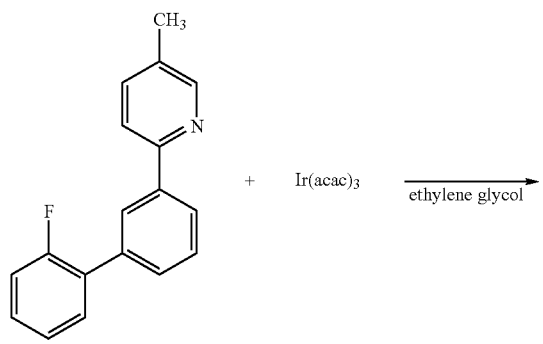

+ Ir(acac)₃ →(ethylene glycol)

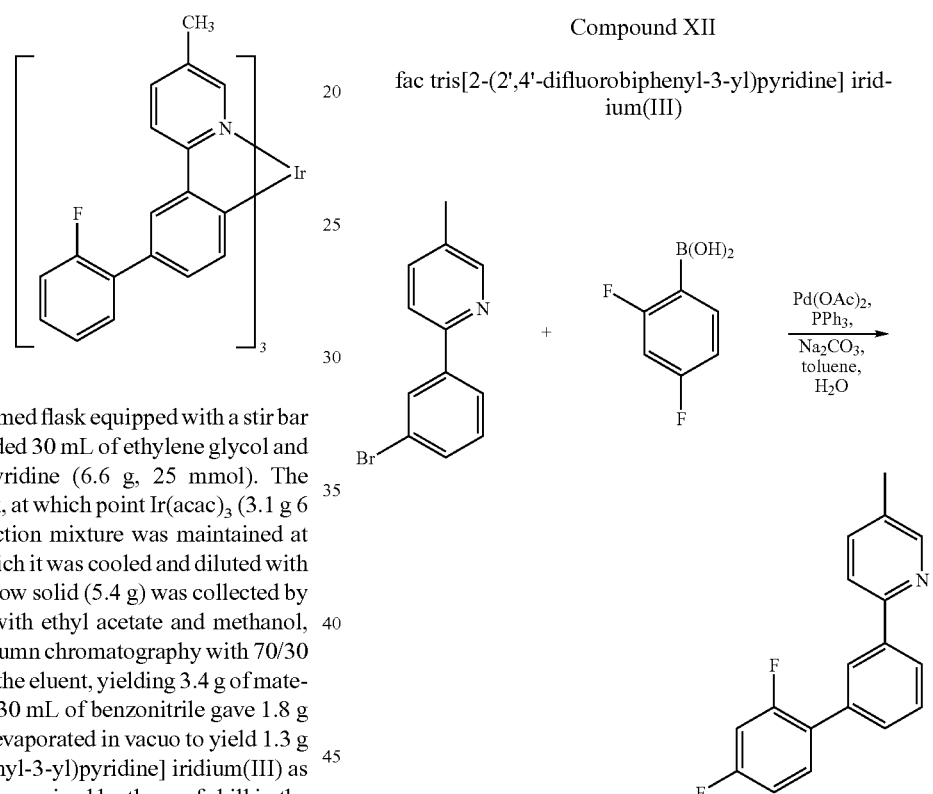

To a 100 mL, round-bottomed flask equipped with a stir bar and a nitrogen inlet were added 30 mL of ethylene glycol and 2-(2'-fluorobiphenyl-3-yl)pyridine (6.6 g, 25 mmol). The solution was heated to reflux, at which point Ir(acac)₃ (3.1 g 6 mmol) was added. The reaction mixture was maintained at reflux for two days, after which it was cooled and diluted with methanol. The resulting yellow solid (5.4 g) was collected by vacuum filtration, washed with ethyl acetate and methanol, and purified by silica gel column chromatography with 70/30 dichloromethane/hexane as the eluent, yielding 3.4 g of material. Recrystallization from 30 mL of benzonitrile gave 1.8 g of pure material which was evaporated in vacuo to yield 1.3 g of fac tris[2-(2'-fluorobiphenyl-3-yl)pyridine] iridium(III) as yellow crystals. As will be recognized by those of skill in the art, other commercially available fluoro phenylboronic or difluorophenylboronic acids can be used in step 2, to make additional fluoro substituted regioisomers, for example:

Compound XI fac tris[2-(2',3'-difluorobiphenyl-3-yl)pyridine] iridium(III)

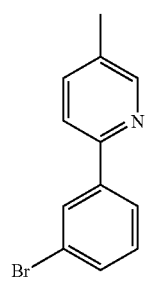 + 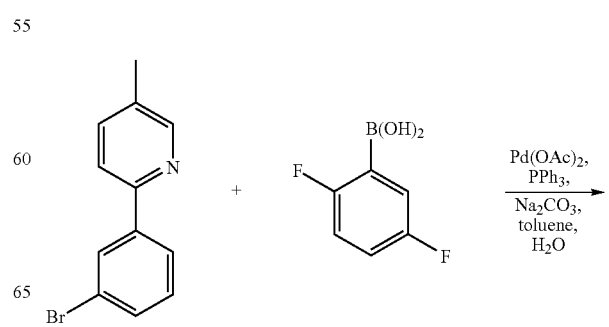

Compound XII fac tris[2-(2',4'-difluorobiphenyl-3-yl)pyridine] iridium(III)

Compound XIII fac tris[2-(2',5'-difluorobiphenyl-3-yl)pyridine] iridium(III)

-continued

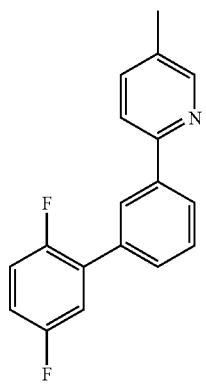

Device Fabrication and Measurement

All devices are fabricated by high vacuum (<10$^{-7}$ Torr) thermal evaporation. The anode electrode is ~1200 Å of indium tin oxide (ITO). The cathode consists of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package. Operational lifetests are performed at constant direct current at room temperature.

For Experimental Devices 1-10 and Comparative Devices 1-2, the organic stack was fabricated to consist of, sequentially from the ITO surface, CuPc as a hole injection layer (HIL) at a thickness of 100 Å, NPD as a hole transport layer (HTL) at a thickness of 300 Å; CBP doped with 6-12 wt % of the dopant emitter (invention compounds and comparative compounds) as the emissive layer at a thickness of 300 Å. Adjacent to the emissive layer was an electron transport layer (ETL2) consisting of 50 or 100 Å of HPT (Devices 2, 4, 6, 8, 10 and Comparative Example Device 2) or 100 Å of BAlq (Devices 1, 3, 5, 7, 9 and Comparative Example Device 1). Adjacent to layer ETL2 was another electron transport layer (ETL1) consisting of Alq$_3$ at a thickness of 400 or 450 Å.

The luminous efficiency and external quantum efficiency of Devices 1-10 and Comparative Example Devices 1 and 2 were measured and are summarized in Table 1.

Very high efficiencies are obtained. It is generally believed that in thin film light emitting devices, due to the optical constraints, only about 20-30% of the light generated inside the device is observed through the transparent side(s) of the device. Highest external quantum efficiencies obtained for OLEDs are of phosphorescent types which reportedly are about 19% [Adachi et al, J. Apply. Phys. 90 (2001) 5048 and Ikai et al, Appl. Phys. Lett. 79 (2001) 156]. It can be seen that examples 6, 8 and 10 have maximum external quantum efficiencies of 20-23%. They represent the highest efficiency OLEDs thus far reported. At 1000 cd/m$^2$, the efficiencies of Ir(5-Phppy)$_3$-doped devices (Comparative Devices 1 and 2) are 6.9% and 9.9% respectively, whereas those of Ir(5'-Me-5-Phppy)$_3$-doped Experimental Devices 4 and 5 are 12.8% and 12% respectively. Since they are based on the same device structure and similar emitting dopant concentration, the results indicate that the addition of the 5'-methyl group plays a role in the efficiency enhancement. Without being limited to any particular theory of how the invention works, it is believed that this efficiency improvement may be due to the improved charge trapping, particularly hole trapping behavior of the invention compounds. It is further believed that alkyl groups other than methyl group will have the same effect in efficiency enhancement. Higher efficiencies are demonstrated by Ir(5'-Me-5-Phppy)$_3$-doped Devices 6 and 8 which utilize HPT as the ETL2 compared to Ir(5'-Me-5-Phppy)$_3$-doped Devices 5 and 7 respectively which utilize BAlq as the ETL2. Again, without being limited to a particular theory, it is believed that the enhanced electron injection and/or hole blocking properties of HPT as the ETL2 results in the improvement of efficiency compared to devices with BAlq as the ETL2.

Table 2 shows the operational stability of the devices using the 5'-alkyl substituted invention compounds compared to the devices using Ir(5-Phppy)$_3$ which has no 5'-alkyl group (Comparative Example Device 1). Device stability was characterized by measuring device luminance as a function of time under constant current drive of 40 mA/cm$^2$ at room temperature. While Comparative Example Device 1 exhibited the longest operational half life [T$_{(0.5)}$=300 hours], it operated at lower initial luminance (L$_0$) than the Examples of the present invention, of about 9000 cd/m$^2$ for Comparative Example Device 1 vs. L$_0$ of about 12,700 cd/m$^2$ for experi-

TABLE 1

| Device | Dopant Compound | Compound No. | % doping | ETL2 (thickness) | ETL1 (thickness) | Luminous efficiency at 1000 cd/m$^2$ (cd/A) | External quantum efficiency at 1000 cd/m$^2$ (%) |
|---|---|---|---|---|---|---|---|
| 1 | Ir(5'-Meppy)$_3$ | I | 6 | BAlq (100 Å) | Alq$_3$ (400 Å) | 42.4 | 12 |
| 2 | Ir(5'-Meppy)$_3$ | I | 6 | HPT (100 Å) | Alq$_3$ (400 Å) | 40.5 | 11.3 |
| 3 | Ir(5'-Me-5-Phppy)$_3$ | II | 6 | BAlq (100 Å) | Alq$_3$ (400 Å) | 50.3 | 13.6 |
| 4 | Ir(5'-Me-5-Phppy)$_3$ | II | 6 | HPT (50 Å) | Alq$_3$ (450 Å) | 47.5 | 12.8 |
| 5 | Ir(5'-Me-5-Phppy)$_3$ | II | 8 | BAlq (100 Å) | Alq$_3$ (400 Å) | 44.4 | 12 |
| 6 | Ir(5'-Me-5-Phppy)$_3$ | II | 8 | HPT (50 Å) | Alq$_3$ (450 Å) | 66.3 | 17.9 |
| 7 | Ir(5'-Me-5-Phppy)$_3$ | II | 10 | BAlq (100 Å) | Alq$_3$ (400 Å) | 32.5 | 8.8 |
| 8 | Ir(5'-Me-5-Phppy)$_3$ | II | 10 | HPT (50 Å) | Alq$_3$ (450 Å) | 80.1 | 21.5 |
| 9 | Ir(5'-Me-5-Phppy)$_3$ | II | 12 | BAlq (100 Å) | Alq$_3$ (400 Å) | 24.2 | 6.5 |
| 10 | Ir(5'-Me-5-Phppy)$_3$ | II | 12 | HPT (50 Å) | Alq$_3$ (450 Å) | 81.7 | 22 |
| Comparative Example Device 1 | Ir(5-Phppy)$_3$ | III | 7 | BAlq (100 Å) | Alq$_3$ (400 Å) | 26 | 6.9 |
| Comparative Example Device 2 | Ir(5-Phppy)$_3$ | III | 6 | HPT (50 Å) | Alq$_3$ (450 Å) | 36.6 | 9.9 | mental Device 1; 10,700 cd/m² for Experimental Device 2; 17,000 cd/m² for Experimental Device 5 and 16000 cd/m² for Example 6.

When scaled to display operation brightness ($L_0$~300 cd/m² for red emitting devices and 600 cd/m² for green emitting devices) the operational half life of Comparative Example Device 1 (a green emitting device) is at least 10,000 hours (as disclosed in U.S. Application Publication No. 2004/0086743 which is incorporated by reference herein in its entirety). Example 5, having a $T_{(0.5)}$ of 190 hours with an initial luminance of about 17000 cd/m², may appear to be shorter-lived than Comparative Example Device 1. Nonetheless, it operates at a much higher brightness ($L_0$=17000 vs 9000 cd/m²). The $T_{(0.5)}$-$L_0$ product is therefore 300×9000=2.7×10⁶ nit.hours and 200×17000=3.23×10⁶ nit.hours, respectively for Comparative Example Device 1 and example 5. It can be seen that example 6 (3.2×10⁶ nit.hours) also has a higher $T_{(0.5)}$-$L_0$ product than Comparative Example Device 1. When scaled to display operation brightness ($L_0$~300 cd/m² and 600 cd/m² for the red and green emitting devices respectively), the devices in accordance with embodiments of the present invention can advantageously have an operational half-life in excess of about 10,000 hours. It is believed, therefore, the invention compounds have advantageously very high device efficiency and long operational lifetimes. Such properties render them extremely suitable for display and lighting applications.

known devices. While those devices exemplified in Experimental Devices 1-10 herein are green emitting devices comprising phenylpyridine type ligands, devices of the present invention can emit at any color. For example, phenylisoquinoline ligands can be coordinated to a metal atom for use in red-emitting devices as disclosed in U.S. Publication No. 2003/0072964 and U.S. application Ser. No. 10/829,011, now U.S. Pat. No. 7,087,321, by reference in their entireties. When the substituents taught herein are incorporated into the emissive material of these devices, it is expected they will similarly exhibit high external quantum and luminous efficiencies and long lifetimes. Accordingly, the present invention encompasses methods of increasing device efficiency, such as can be measured for a device comprising a compound of the present invention, relative to that from a device comprising a reference compound having the same structure, but without the substituents at the substitution site(s) disclosed herein.

In further experiments, Experimental Devices 11-26, and 29-40 were fabricated similarly to the Experimental Devices 1-10. Experimental Devices 27 and 28 and Comparative Example Devices 3 and 4 were also similarly fabricated except their emissive layers consisted of a neat layer of emissive material Ir[5'-Me-5-(2-MePh)ppy]₃ for Experimental Devices 27 and 28 and Ir(3'-Meppy)₃ for Comparative Example Devices Device 3 and 4. The luminous efficiency and external quantum efficiency of Experimental Devices 11-40 and Comparative Example Devices 3 and 4 were measured and are summarized in Table 3.

TABLE 2

| Device | Dopant Compound | Compound No. | $L_0$(cd/m²) at J = 40 mA/cm² | $T_{(0.5)}$ (hr) | $T_{(0.5)}$ × $L_0$ (nit · hour) |
|---|---|---|---|---|---|
| 1 | Ir(5'-Meppy)₃ | I | 12000 | 70 | 8.4 × 10⁵ |
| 2 | Ir(5'-Meppy)₃ | I | 10700 | 100 | 1.07 × 10⁶ |
| 5 | Ir(5'-Me-5-Phppy)₃ | II | 17000 | 190 | 3.23 × 10⁶ |
| 6 | Ir(5'-Me-5-Phppy)₃ | II | 16000 | 200 | 3.20 × 10⁶ |
| Comparative Example Device 1 | Ir(5-Phppy)₃ | III | 9000 | 300 | 1.07 × 10⁶ |

As demonstrated, devices comprising the present invention compounds have superior properties as compared with

TABLE 3

| Device | Dopant | Compound No. | % doping | ETL2 (thickness) | ETL1 (thickness) | Luminous efficiency at 1000 cd/m² (cd/A) | External quantum efficiency at 1000 cd/m² (%) |
|---|---|---|---|---|---|---|---|
| 11 | Ir(3-Me-dhbq)₃ | V | 6 | BAlq (100 Å) | Alq₃ (400 Å) | 43.4 | 12 |
| 12 | Ir(3-Me-dhbq)₃ | V | 6 | HPT (50 Å) | Alq₃ (450 Å) | 34.8 | 9.6 |
| 13 | Ir(3-Me-dhbq)₃ | V | 8 | BAlq (100 Å) | Alq₃ (400 Å) | 48.3 | 13.3 |
| 14 | Ir(3-Me-dhbq)₃ | V | 8 | HPT (50 Å) | Alq₃ (450 Å) | 43.2 | 11.9 |
| 15 | Ir(3-Me-dhbq)₃ | V | 10 | BAlq (100 Å) | Alq₃ (400 Å) | 40.4 | 11.1 |
| 16 | Ir(3-Me-dhbq)₃ | V | 10 | HPT (50 Å) | Alq₃ (450 Å) | 46 | 12.6 |
| 17 | Ir[5'-Me-5-(2-MePh)ppy]₃ | VI | 6 | BAlq (100 Å) | Alq₃ (400 Å) | 47.3 | 13 |
| 18 | Ir[5'-Me-5-(2-MePh)ppy]₃ | VI | 6 | HPT (50 Å) | Alq₃ (450 Å) | 42.5 | 11.7 |
| 19 | Ir[5'-Me-5-(2-MePh)ppy]₃ | VI | 8 | BAlq (100 Å) | Alq₃ (400 Å) | 45.6 | 12.5 |
| 20 | Ir[5'-Me-5-(2-MePh)ppy]₃ | VI | 8 | HPT (50 Å) | Alq₃ (450 Å) | 50 | 13.7 |
| 21 | Ir[5'-Me-5-(2-MePh)ppy]₃ | VI | 12 | BAlq (100 Å) | Alq₃ (400 Å) | 30.3 | 8.3 |
| 22 | Ir[5'-Me-5-(2-MePh)ppy]₃ | VI | 12 | HPT (50 Å) | Alq₃ (450 Å) | 62 | 17.1 |
| 23 | Hexadentate Ligand Complex | VII | 6 | BAlq (100 Å) | Alq₃ (400 Å) | 43 | 11.9 |
| 24 | Hexadentate Ligand Complex | VII | 6 | HPT (50 Å) | Alq₃ (450 Å) | 38.5 | 10.7 |
| 25 | Hexadentate Ligand Complex | VII | 10 | BAlq (100 Å) | Alq₃ (400 Å) | 36.4 | 10 |
| 26 | Hexadentate Ligand Complex | VII | 10 | HPT (50 Å) | Alq₃ (450 Å) | 56 | 15.4 |
| 27 | Ir[5'-Me-5-(2-MePh)ppy]₃ | VI | 100 | BAlq (100 Å) | Alq₃ (400 Å) | 2.7 | 0.9 |
| 28 | Ir[5'-Me-5-(2-MePh)ppy]₃ | VI | 100 | HPT (50 Å) | Alq₃ (450 Å) | 23.3 | 6.6 |
| Comp. | Ir(3'-Meppy)₃ | | 100 | BAlq (100 Å) | Alq₃ (400 Å) | 1.8 | 0.6 |

TABLE 3-continued

| Device | Dopant | Compound No. | % doping | ETL2 (thickness) | ETL1 (thickness) | Luminous efficiency at 1000 cd/m² (cd/A) | External quantum efficiency at 1000 cd/m² (%) |
|---|---|---|---|---|---|---|---|
| Example Device3 | | | | | | | |
| Comp. Example Device4 | Ir(3'-Meppy)₃ | | 100 | HPT (50 Å) | Alq₃ (450 Å) | 8.8 | 2.5 |
| 29 | Ir[5'-Me-5-(4-FPh)ppy]₃ | VIII | 6 | BAlq (100 Å) | Alq₃ (400 Å) | 42 | 11.6 |
| 30 | Ir[5'-Me-5-(4-FPh)ppy]₃ | VIII | 6 | HPT (50 Å) | Alq₃ (450 Å) | 42 | 11.6 |
| 31 | Ir[5'-Me-5-(4-FPh)ppy]₃ | VIII | 8 | BAlq (100 Å) | Alq₃ (400 Å) | 45 | 12.4 |
| 32 | Ir[5'-Me-5-(4-FPh)ppy]₃ | VIII | 8 | HPT (50 Å) | Alq₃ (450 Å) | 53 | 14.6 |
| 33 | Ir[5'-Me-5-(4-FPh)ppy]₃ | VIII | 10 | BAlq (100 Å) | Alq₃ (400 Å) | 42 | 11.6 |
| 34 | Ir[5'-Me-5-(4-FPh)ppy]₃ | VIII | 10 | HPT (50 Å) | Alq₃ (450 Å) | 60 | 16.6 |
| 35 | Ir[5'-Me-5-(3-FPh)ppy]₃ | IX | 6 | BAlq (100 Å) | Alq₃ (400 Å) | 39 | 10.7 |
| 36 | Ir[5'-Me-5-(3-FPh)ppy]₃ | IX | 6 | HPT (50 Å) | Alq₃ (450 Å) | 42 | 11.5 |
| 37 | Ir[5'-Me-5-(3-FPh)ppy]₃ | IX | 8 | BAlq (100 Å) | Alq₃ (400 Å) | 39 | 10.7 |
| 38 | Ir[5'-Me-5-(3-FPh)ppy]₃ | IX | 8 | HPT (50 Å) | Alq₃ (450 Å) | 48 | 13.2 |
| 39 | Ir[5'-Me-5-(3-FPh)ppy]₃ | IX | 10 | BAlq (100 Å) | Alq₃ (400 Å) | 37 | 10.1 |
| 40 | Ir[5'-Me-5-(3-FPh)ppy]₃ | IX | 10 | HPT (50 Å) | Alq₃ (450 Å) | 47 | 15.7 |

Again, the phosphorescent light emitting devices fabricated according to the present invention showed very high external quantum efficiency.

The voltage is also low (typically <9 V at 10 mA/cm2) for devices having HPT ETL2. For the Ir(5-Phppy)₃ which has no 5'-alkyl group device the voltage is about 9.5-10 V for the same device architecture (Comparative Example Device 2). The driving voltages of the devices with the invention compounds are about 1 to 1.5 V lower than the devices with previously known analogs having no alkyl substitution at the 5' position. These low driving voltages further increase the power efficiency of the devices In addition to the high efficiency, the invention compounds also evaporate at mild temperatures. Lower evaporation temperatures can reduce damage due to thermal degradation under prolonged heating during OLED manufacturing by thermal vacuum deposition or other deposition processes that require vapor transport of the materials. The evaporated temperature of organic materials used in OLEDs is an important aspect in OLED manufacturing. The evaporation temperature is the deposition temperature at a deposition rate of ~0.2 Å/s at the substrate under a vacuum of <$10^{-7}$ torr where the source and the substrate distance is about 50 cm. Under these conditions, Ir(3-Me-dhbq)₃ (Compound Example V), Ir[5'-Me-5-(2-MePh)ppy]₃ (Compound Example VI), and the hexadentate ligand complex (Compound Example VII) evaporate at ~235° C., ~265° C. and ~270° C. respectively. These temperatures are lower than that of Ir(5-Phppy)₃ (Comparative Example Compound III) which evaporates at ~300° C. under the same conditions.

Modifications to the 5'alkyl substituted ligands of the present invention including further substitutions with certain substituents may further lower the evaporation temperature of the complexes. For example, as shown in the Table 4 (where the phenyl substituent at the 5 position is designated ring "C"), invention compounds Ir(5'-Me-5-Phppy)₃ (Compound Example No. II), Ir[5'-Me-5-(2-MePh)ppy]₃ (Compound Example No. VII), Ir[5'-Me-5-(4-FPh)ppy]₃ (Compound Example No. VIII) and Ir[5'-Me-5-(3-FPh)ppy]₃ (Compound Example No. IX) have evaporation temperatures ($T_{evp}$) of 315° C., 270° C., 280° C. and 280° C. respectively. As also shown in Table 4, Compound Nos. II, VII and VIII and 1× have dihedral angles between rings B and C of 48°, 87°, 48° and 48° respectively.

TABLE 4

| Compound No. | Name | Structure | Dihedral angle | $T_{evp}$ (° C.) |
|---|---|---|---|---|
| II | [Ir(5'-Me-5-Phppy)₃] | 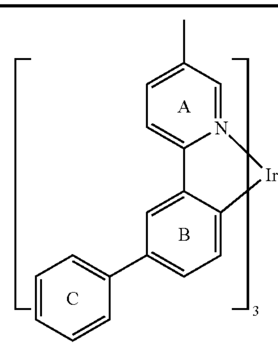 | 48° | 315 |

TABLE 4-continued

| Compound No. | Name | Structure | Dihedral angle | $T_{evp}$ (° C.) |
|---|---|---|---|---|
| VII | Ir[5'-Me-5-(2-MePh) | 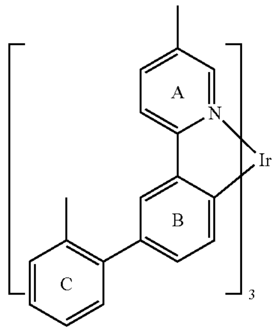 | 87° | 270 |
| VIII | Ir[5'-Me-5-(4-FPh)ppy]₃ | 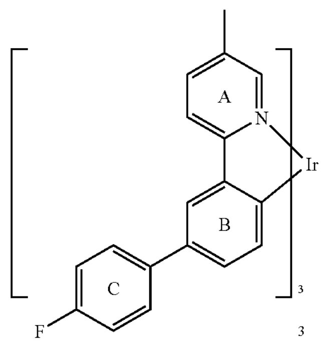 | 48° | 280 |
| IX | Ir[5'-Me-5-(3-FPh)ppy]₃ | 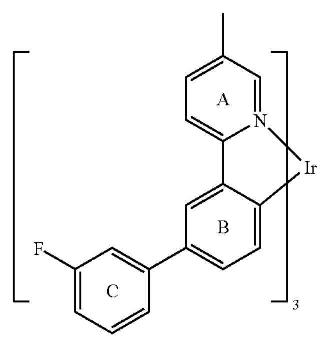 | 48° | 280 |

It is believed that the lower evaporation temperature exhibited by Compound Example No. VII is due to the twisting between rings B and C exerted by the steric hindrance from the presence of a bulky methyl substituent at the 5 position on Ring B. The increased non-coplanarity exerted by such substituent groups reduces intermolecular packing in the solid state. It is well known that a high degree of intermolecular packing in organic materials increases the evaporation temperature and reduces the solubility. Therefore, in preferred embodiments, phenyl ring C may have substituents that cause ring C to be equally or less co-planar with respect to ring B than when ring C is un-substituted. Substituents on ring C that cause rings B and C to be more co-planar, especially substituents resulting in dihedral angles less than 20° may be less desirable. It is expected that compounds where ring C has bridging substituents such as

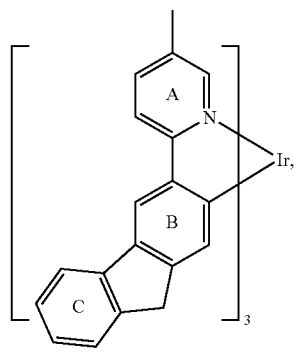

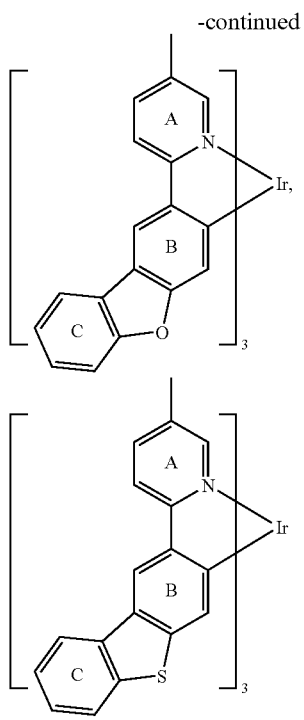

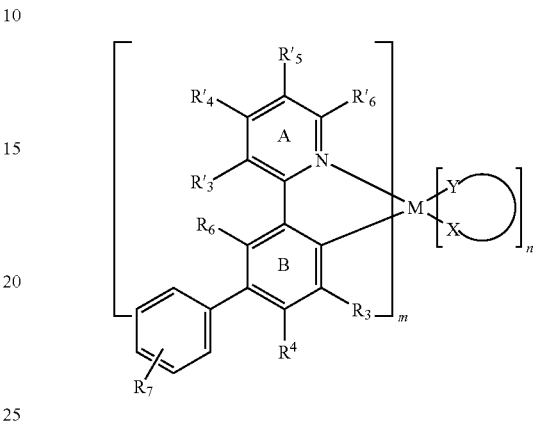

(which have dihedral angles between rings B and C of about 0°) would not lower evaporation temperatures over the compounds where ring C is unsubstituted due to increased molecular packing when the phenyl rings are coplanar. Thus, preferred substituents are those that result in a dihedral angle between Rings B and C of at least 20°, more preferably at least 45° and most preferably greater than 45°. As also shown in Table 4, Examples VIII and IX exhibit evaporation temperatures that are 35° C. lower than that of Example II. While the dihedral angles between Rings B and C are similar for Examples II, VIII and IV (48°), it is believed that fluorine-containing substituents such as those in Examples VIII and IX can lower the degree of molecular packing in the solid state, hence lowering evaporation temperature in organic materials because fluoro groups have weak van der Waals interactions with regular organic groups. Therefore, fluorine containing substituents are desirable groups to lower the evaporation temperature.

When the compounds of the present invention are designed to phosphoresce as green, conjugated substituents on Ring C may not be desirable. Conjugated substituents, such as a fused benzene or other fused aromatic ring, tend to delocalize the electrons in the ligand and lead to a lower triplet energy for the organometallic complex (resulting in a red-shift in the phosphorescence). Fused benzene or other aromatic ring substituent on ring C is also believed to increase the evaporation temperature as the fused rings may induce additional molecular packing of the compounds in the solid state. Thus, particularly preferred substituents on Ring C are non-conjugated substituents that do not cause electron delocalization and those that result in increased non-coplanarity between Rings B and C relative to the degree of coplanarity when Ring C (for example, phenyl) is unsubstituted.

While the present invention is described with respect to particular examples and preferred embodiments, it is understood that the present invention is not limited to these examples and embodiments. For example, the phosphorescent materials may contain stereo and/or structural isomers. The present invention as claimed therefore includes variations from the particular examples and preferred embodiments described herein and set forth below, as will be apparent to one of skill in the art.

What is claimed is:
1. A compound having the formula:

wherein M is a metal selected from Ir, Pt, Rh or Pd;
(X-Y) is an ancillary ligand;
m is a value from 1 to the maximum number of ligands that may be attached to the metal; and m+n is the maximum number of ligands that may be attached to the metal;
ring A is an aromatic heterocyclic or a fused aromatic heterocyclic having an unsubstituted alkyl substituent at the $R'_5$ position and having at least one nitrogen atom, N, that is coordinated to the metal M,
wherein the ring A can be optionally substituted with one or more substituents at the $R'_3$, $R'_4$ and $R'_6$ positions; $R'_3$, $R'_4$, and $R'_6$ are each independently H, alkyl, alkenyl, alkynyl, heteroalkyl, aryl, heteroaryl, aralkyl,; and wherein $R'_3$, $R'_4$, and, $R'_6$ are optionally substituted by one or more substituents Z;
additionally or alternatively the $R'_3$ and $R'_4$ substituted positions on ring A together form a fused ring, wherein the fused ring may be optionally substituted;
ring B is an aromatic ring with at least one carbon atom coordinated to metal M, wherein ring B can be optionally substituted with one or more substituents at the $R_3$, $R_4$, and $R_6$ positions;
$R_3$, $R_4$, and $R_6$ is each independently selected from the group consisting of H, alkyl, alkenyl, alkynyl, alkylaryl, CN, $CO_2R$, $C(O)R$, $NR_2$, OR, halo, aryl, heteroaryl, substituted aryl, substituted heteroaryl or a heterocyclic group;
alternatively, $R'_3$ and $R_6$ may be bridged by a group selected from, —CR=CR—, —CR$_2$—, —O—, —NR—, —O—CR$_2$—, —NR—CR$_2$—, and —N=CR—;
each R is independently H, alkyl, alkenyl, alkynyl, heteroalkyl, aryl, heteroaryl, or aralkyl;
wherein R is optionally substituted by one or more substituents Z;
each Z is independently a halogen, R', OR', N(R')$_2$, SR', C(O)R', C(O)OR', C(O)N(R')$_2$, CN, SO$_2$, SOR', SO$_2$R', or SO$_3$R';
each R' is independently H, alkyl, alkenyl, alkynyl, heteroalkyl, aryl, or heteroaryl; and wherein R$_7$ represents one or more optional substitutions located on any position of the phenyl ring attached to ring B, wherein the optional R$_7$ substitutions are all fluoro or all alkyl.
2. The compound of claim 1 wherein m=3.
3. The compound of claim 1 having the formula:
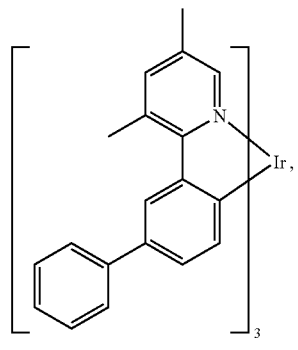
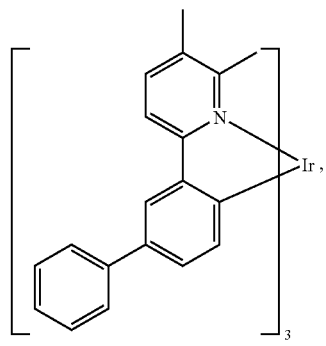
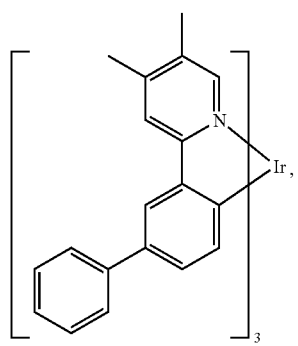
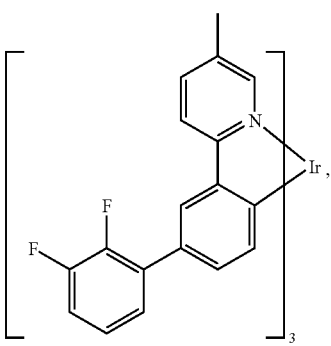
-continued
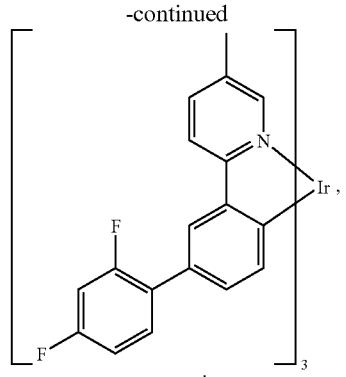
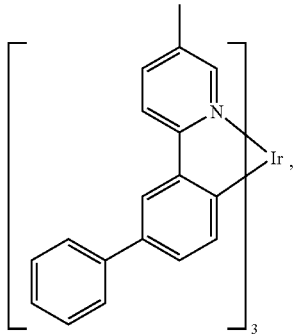
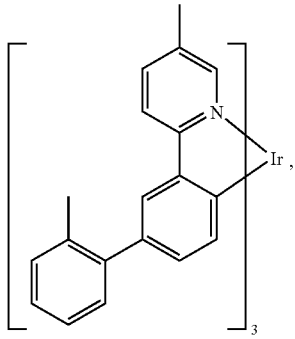
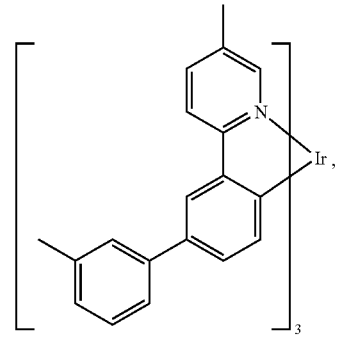
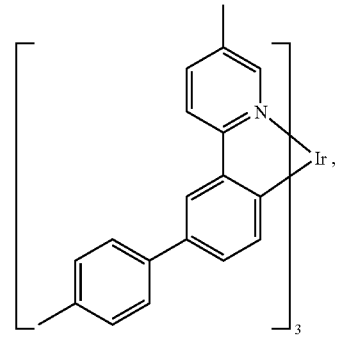

-continued

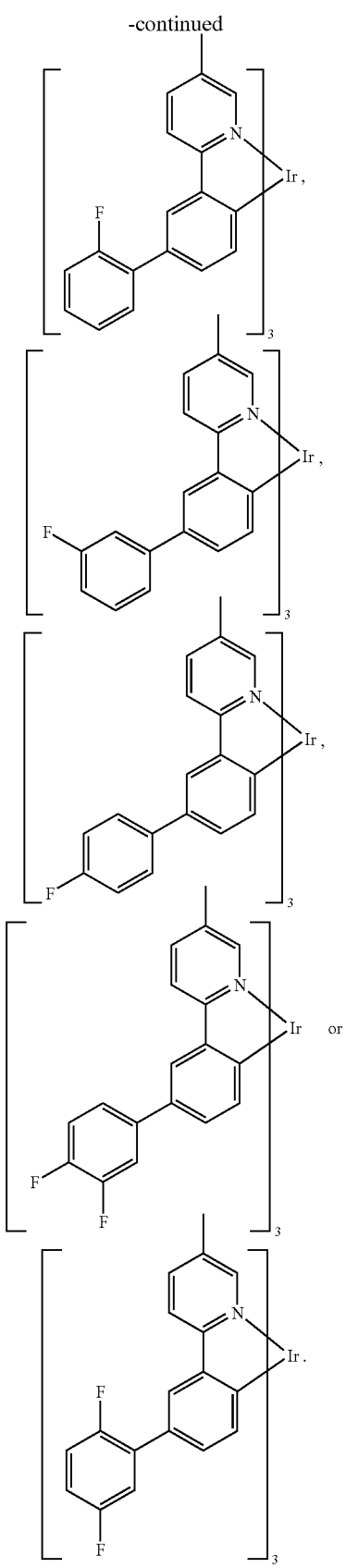

4. The compound of claim 1 wherein at least one of R'$_3$, R'$_4$, and R'$_6$ is not H.

5. The compound of claim 4 wherein at least one of R'$_3$, R'$_4$, and R'$_6$ is alkyl or phenyl.

6. The compound of claim 1 wherein R'$_3$, R'$_4$, R'$_6$, R$_3$, R$_4$, and R$_6$ are all H.

7. A device comprising:
   an anode;
   a cathode;
   a first organic layer including an emissive material disposed between the anode and the cathode, the emissive material comprising a compound as set forth in claim 1.

8. The device of claim 7 further comprising a second organic layer disposed between the first organic layer and the cathode, wherein the second organic layer is in direct contact with the first organic layer, and wherein the second organic layer comprises a non-heterocyclic aromatic hydrocarbon material.

9. The device of claim 7 wherein the device produces phosphorescent emission and has an unmodified external quantum efficiency in the range of 10% to 23% at current densities between about 0.1 to about 1000 mA/cm$^2$.

10. The device of claim 8, wherein the aromatic hydrocarbon material has a molecular dipole moment less than about 2.0 debyes.

11. The device of claim 7, wherein the device has a T$_{(0.5)}$-L$_0$ product that is at least 3×10$^6$ nit-hours.

12. The device of claim 7, wherein the emissive material has the structure:

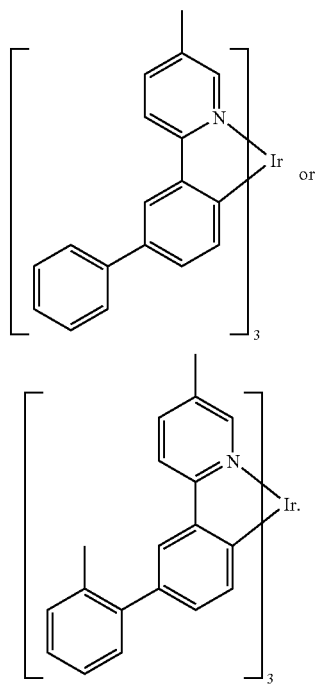

* * * * *